US008173697B2

(12) United States Patent
Fischer et al.

(10) Patent No.: US 8,173,697 B2
(45) Date of Patent: May 8, 2012

(54) ALKOXYALKYL-SUBSTITUTED CYCLIC KETO-ENOLS

(75) Inventors: Reiner Fischer, Monheim (DE); Stefan Lehr, Liederbach (DE); Dieter Feucht, Eschborn (DE); Olga Malsam, Rösrath (DE); Christian Arnold, Langenfeld (DE); Martin Jeffrey Hills, Idstein (DE); Heinz Kehne, Hofheim (DE); Christopher Hugh Rosinger, Hofheim (DE); Rolf Pontzen, Leichlingen (DE); Ulrich Görgens, Ratingen (DE); Jan Dittgen, Frankfurt (DE)

(73) Assignee: Bayer CropScience AG, Monheim (DE)

( * ) Notice: Subject to any disclaimer, the term of this patent is extended or adjusted under 35 U.S.C. 154(b) by 125 days.

(21) Appl. No.: 12/303,206

(22) PCT Filed: May 23, 2007

(86) PCT No.: PCT/EP2007/004551
§ 371 (c)(1),
(2), (4) Date: Apr. 27, 2009

(87) PCT Pub. No.: WO2007/140881
PCT Pub. Date: Dec. 13, 2007

(65) Prior Publication Data
US 2009/0298828 A1 Dec. 3, 2009

(30) Foreign Application Priority Data
Jun. 2, 2006 (DE) .................. 10 2006 025 874

(51) Int. Cl.
A61K 31/40 (2006.01)
C07D 207/00 (2006.01)
(52) U.S. Cl. ........................ 514/449; 548/544
(58) Field of Classification Search .................. 548/544
See application file for complete search history.

(56) References Cited

U.S. PATENT DOCUMENTS

| 2,842,476 | A |   | 7/1958  | Schreiber et al. |
|-----------|---|---|---------|------------------|
| 4,021,224 | A |   | 5/1977  | Pallos et al. |
| 4,186,130 | A |   | 1/1980  | Teach |
| 4,623,727 | A |   | 11/1986 | Hübele |
| 4,639,266 | A |   | 1/1987  | Heubach et al. |
| 4,844,734 | A |   | 7/1989  | Iwasaki et al. |
| 4,881,966 | A |   | 11/1989 | Nyffeler et al. |
| 4,888,049 | A |   | 12/1989 | Iwasaki et al. |
| 4,891,057 | A |   | 1/1990  | Sohn et al. |
| 4,902,340 | A |   | 2/1990  | Hubele |
| 4,925,868 | A |   | 5/1990  | Terao et al. |
| 4,985,063 | A |   | 1/1991  | Fischer et al. |
| 5,045,560 | A |   | 9/1991  | Fischer et al. |
| 5,116,836 | A |   | 5/1992  | Fischer et al. |
| 5,164,179 | A |   | 11/1992 | Hioki et al. |
| 5,225,434 | A |   | 7/1993  | Bertram et al. |
| 5,258,527 | A | * | 11/1993 | Krauskopf et al. ........... 548/543 |
| 5,298,501 | A |   | 3/1994  | Cummings |
| 5,314,863 | A |   | 5/1994  | Löher et al. |
| 5,380,852 | A |   | 1/1995  | Schütze et al. |
| 5,401,700 | A |   | 3/1995  | Sohn et al. |
| 5,407,897 | A |   | 4/1995  | Cary et al. |
| 5,462,912 | A |   | 10/1995 | Hioki et al. |
| 5,462,913 | A |   | 10/1995 | Fischer et al. |
| 5,504,057 | A |   | 4/1996  | Fischer et al. |
| 5,508,436 | A |   | 4/1996  | Fischer et al. |
| 5,516,750 | A |   | 5/1996  | Willms et al. |
| 5,538,937 | A |   | 7/1996  | Hasebe et al. |
| 5,567,671 | A |   | 10/1996 | Fischer et al. |
| 5,589,469 | A |   | 12/1996 | Fischer et al. |
| 5,622,917 | A |   | 4/1997  | Fischer et al. |
| 5,683,965 | A |   | 11/1997 | Bachmann et al. |
| 5,700,758 | A |   | 12/1997 | Rösch et al. |
| 5,705,476 | A |   | 1/1998  | Hoffarth |

(Continued)

FOREIGN PATENT DOCUMENTS

CA 1 162 071 2/1984

(Continued)

OTHER PUBLICATIONS

Mushrooms [online] retrieved on Jan. 31, 2011 from the internet (URL; http://www.american-lawns.com/problems/weeds/mushrooms.html.*

Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, SCI (1997).

Bhattacharya, B., "Isoquinoline Derivatives: Part XVIII—Formation of I-Alkyl-(or alkaryl or aryl)-3-methyl-7-chloro-(or 5-chloro)-isoquinolines," *Indian J. Chem.* 6:341-345, Council of Scientific and Industrial Research (1968).

(Continued)

*Primary Examiner* — Shawquia Young
(74) *Attorney, Agent, or Firm* — Sterne, Kessler, Goldstein & Fox P.L.L.C.

(57) ABSTRACT

The invention relates to new alkoxyalkyl-substituted cyclic ketoenols of the formula (I)

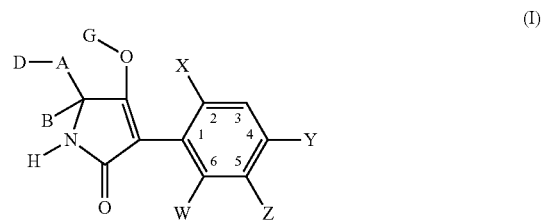

(I)

in which A, B, D, G, W, X, Y and Z have the definitions indicated above,
to a number of processes and intermediates for their preparation, and to their use as pesticides and/or herbicides and/or microbicides.
The invention further provides selectively herbicidal, compositions which comprise alkoxyalkyl-substituted cyclic ketoenols on the one hand and a crop plant tolerance promoter compound on the other.
The invention further relates to the boosting of the action of crop protection compositions comprising compounds of the formula (I) through the additions of ammonium salts or phosphonium salts and optionally penetration promoters.

17 Claims, No Drawings

U.S. PATENT DOCUMENTS

| Number | | Date | Inventor |
|---|---|---|---|
| 5,739,079 | A | 4/1998 | Holdgrün et al. |
| 5,792,755 | A | 8/1998 | Sagenmüller et al. |
| 5,811,374 | A | 9/1998 | Bertram et al. |
| 5,830,826 | A | 11/1998 | Fischer et al. |
| 5,994,274 | A | 11/1999 | Fischer et al. |
| 6,110,872 | A | 8/2000 | Lieb et al. |
| 6,114,374 | A | 9/2000 | Lieb et al. |
| 6,133,296 | A | 10/2000 | Lieb et al. |
| 6,140,358 | A | 10/2000 | Lieb et al. |
| 6,200,932 | B1 | 3/2001 | Fischer et al. |
| 6,235,680 | B1 | 5/2001 | Ziemer et al. |
| 6,251,827 | B1 | 6/2001 | Ziemer et al. |
| 6,251,830 | B1 | 6/2001 | Fischer et al. |
| 6,288,102 | B1 | 9/2001 | Hagemann et al. |
| 6,316,486 | B1 | 11/2001 | Lieb et al. |
| 6,358,887 | B1 | 3/2002 | Fischer et al. |
| 6,359,151 | B2 | 3/2002 | Lieb et al. |
| 6,417,370 | B1 | 7/2002 | Lieb et al. |
| 6,451,843 | B1 | 9/2002 | Lieb et al. |
| 6,458,965 | B1 | 10/2002 | Lieb et al. |
| 6,472,419 | B1 | 10/2002 | Fischer et al. |
| 6,511,940 | B1 | 1/2003 | Ziemer et al. |
| 6,511,942 | B1 | 1/2003 | Lieb et al. |
| 6,589,976 | B1 | 7/2003 | Fischer et al. |
| 6,602,823 | B1 | 8/2003 | Röchling et al. |
| 6,608,211 | B1 | 8/2003 | Hagemann et al. |
| 6,645,914 | B1 | 11/2003 | Woznica et al. |
| 6,861,391 | B1 | 3/2005 | Fischer et al. |
| 6,894,005 | B1 | 5/2005 | Maetzke et al. |
| 7,432,225 | B2 * | 10/2008 | Fischer et al. ............... 504/105 |
| 2003/0216260 | A1 | 11/2003 | Ruther et al. |
| 2003/0224939 | A1 | 12/2003 | Miles |
| 2005/0009880 | A1 | 1/2005 | Cottrell et al. |
| 2005/0054535 | A1 | 3/2005 | Fischer et al. |
| 2005/0090399 | A1 | 4/2005 | Friedmann et al. |
| 2005/0096386 | A1 | 5/2005 | Cottrell et al. |
| 2006/0160847 | A1 | 7/2006 | Fischer et al. |
| 2006/0166829 | A1 | 7/2006 | Fischer et al. |
| 2007/0015664 | A1 | 1/2007 | Fischer et al. |
| 2007/0032539 | A1 | 2/2007 | Himmler |
| 2007/0129252 | A1 | 6/2007 | Fischer et al. |
| 2007/0225167 | A1 | 9/2007 | Fischer et al. |
| 2007/0225170 | A1 | 9/2007 | Fischer et al. |
| 2007/0244007 | A1 | 10/2007 | Fischer et al. |
| 2007/0265266 | A1 | 11/2007 | Fisher et al. |
| 2007/0270416 | A1 | 11/2007 | Funke et al. |
| 2007/0275858 | A1 | 11/2007 | Fischer et al. |
| 2007/0276023 | A1 | 11/2007 | Fischer et al. |
| 2007/0298968 | A1 | 12/2007 | Bretschneider et al. |
| 2007/0298969 | A1 | 12/2007 | Fischer et al. |
| 2008/0220973 | A1 | 9/2008 | Fischer et al. |
| 2008/0287435 | A1 | 11/2008 | Fischer et al. |
| 2008/0305955 | A1 | 12/2008 | Bretschneider et al. |
| 2008/0318776 | A1 | 12/2008 | Fischer et al. |
| 2009/0012100 | A1 | 1/2009 | Fischer et al. |
| 2009/0012152 | A1 | 1/2009 | Fischer et al. |
| 2009/0029858 | A1 | 1/2009 | Fischer et al. |
| 2009/0239906 | A1 | 9/2009 | Fischer et al. |
| 2010/0009850 | A1 | 1/2010 | Fischer et al. |

FOREIGN PATENT DOCUMENTS

| Country | Number | | Date |
|---|---|---|---|
| CA | 2 627 240 | A1 | 5/2007 |
| DE | 2218097 | | 11/1972 |
| DE | 2350547 | | 4/1974 |
| DE | 19621522 | A1 | 12/1997 |
| DE | 10 2005 051325 | A1 | 5/2007 |
| DE | 10 2006 018828 | A1 | 10/2007 |
| EP | 0036106 | A2 | 9/1981 |
| EP | 0086750 | A2 | 8/1983 |
| EP | 0094349 | A2 | 11/1983 |
| EP | 0174562 | A2 | 3/1986 |
| EP | 0191736 | A2 | 8/1986 |
| EP | 0262399 | A2 | 4/1988 |
| EP | 0269806 | A1 | 6/1988 |
| EP | 0333131 | A1 | 9/1989 |
| EP | 0346620 | A1 | 12/1989 |
| EP | 0355599 | A1 | 2/1990 |
| EP | 0377893 | A2 | 7/1990 |
| EP | 0415211 | A2 | 3/1991 |
| EP | 0442073 | A2 | 8/1991 |
| EP | 0442077 | A2 | 8/1991 |
| EP | 0453086 | A2 | 10/1991 |
| EP | 0456063 | A2 | 11/1991 |
| EP | 0492366 | A2 | 7/1992 |
| EP | 0521334 | A1 | 1/1993 |
| EP | 0582198 | A2 | 2/1994 |
| EP | 0595130 | A1 | 5/1994 |
| EP | 0596298 | A1 | 5/1994 |
| EP | 0613618 | A1 | 9/1994 |
| EP | 0613884 | A2 | 9/1994 |
| EP | 0613885 | A2 | 9/1994 |
| EP | 0664081 | A2 | 7/1995 |
| EP | 0668267 | A1 | 8/1995 |
| EP | 0681865 | A2 | 11/1995 |
| EP | 0835243 | B1 | 4/1998 |
| EP | 0837847 | B1 | 4/1998 |
| FR | 2600494 | A1 | 12/1987 |
| GB | 2 266 888 | A | 11/1993 |
| JP | 2000-53670 | A | 2/2000 |
| JP | 2002-205984 | A | 7/2002 |
| WO | WO 91/07874 | A1 | 6/1991 |
| WO | WO 91/08202 | A1 | 6/1991 |
| WO | WO 92/16108 | A1 | 10/1992 |
| WO | WO 95/01971 | A1 | 1/1995 |
| WO | WO 95/07897 | A1 | 3/1995 |
| WO | WO 95/17817 | A1 | 7/1995 |
| WO | WO 95/20572 | A1 | 8/1995 |
| WO | WO 95/26954 | A1 | 10/1995 |
| WO | WO 96/25395 | A1 | 8/1996 |
| WO | WO 96/35664 | A1 | 11/1996 |
| WO | WO 97/01535 | A1 | 1/1997 |
| WO | WO 97/02243 | A1 | 1/1997 |
| WO | WO 97/36868 | A1 | 10/1997 |
| WO | WO 97/43275 | A2 | 11/1997 |
| WO | WO 98/05638 | A2 | 2/1998 |
| WO | WO 98/06721 | A1 | 2/1998 |
| WO | WO 98/25928 | A1 | 6/1998 |
| WO | WO 98/35553 | A1 | 8/1998 |
| WO | WO 99/16748 | A1 | 4/1999 |
| WO | WO 99/24437 | A1 | 5/1999 |
| WO | WO 99/43649 | A1 | 9/1999 |
| WO | WO 99/48869 | A1 | 9/1999 |
| WO | WO 99/55673 | A1 | 11/1999 |
| WO | WO 99/66795 | A1 | 12/1999 |
| WO | WO 00/35278 | A1 | 6/2000 |
| WO | WO 01/17972 | A2 | 3/2001 |
| WO | WO 01/23354 | A2 | 4/2001 |
| WO | WO 01/74770 | A1 | 10/2001 |
| WO | WO 02/49641 | A2 | 6/2002 |
| WO | WO 03/013249 | A1 | 2/2003 |
| WO | WO 03/059065 | A1 | 7/2003 |
| WO | WO 03/062244 | A1 | 7/2003 |
| WO | WO 2004/007448 | A1 | 1/2004 |
| WO | WO 2004/024688 | A1 | 3/2004 |
| WO | WO 2004/065366 | A1 | 8/2004 |
| WO | WO 2004/080962 | A1 | 9/2004 |
| WO | WO 2004/111042 | A1 | 12/2004 |
| WO | WO 2005/044791 | A2 | 5/2005 |
| WO | WO 2005/044796 | A1 | 5/2005 |
| WO | WO 2005/048710 | A1 | 6/2005 |
| WO | WO 2005/049569 | A1 | 6/2005 |
| WO | WO 2005/066125 | A1 | 7/2005 |
| WO | WO 2005/092897 | A2 | 10/2005 |
| WO | WO 2006/000355 | A1 | 1/2006 |
| WO | WO 2006/008111 | A1 | 1/2006 |
| WO | WO 2006/029799 | A1 | 3/2006 |
| WO | WO 2006/056281 | A1 | 6/2006 |
| WO | WO 2006/056282 | A1 | 6/2006 |
| WO | WO 2006/089633 | A2 | 8/2006 |
| WO | WO 2007/121868 | A1 | 11/2007 |

OTHER PUBLICATIONS

Compagnon, P.L. and Miocque, M., "Addition des Réactifs Nucléophiles sur la Triple Liaison Nitrile," *Ann. Chim.* 5:11-22, Masson (1970).

Edward, J.T. and Jitrangsri, C., "Stereochemistry of the Bucherer-Bergs and Strecker Reactions of 4-*tert*-Butylcyclohexanone," *Can J. Chem.* 53:3339-3350, NRC Research Press (1975).

Harrison, H.R., et al., "Use of molecular sieves in the methyl esterification of carboxylic acids," *Chem. Ind.*, p. 1568, Society of Chemical Industry (1968).

Ito, M., et al., "Synthesis and Insecticidal Activity of Novel *N*-Oxydihydropyrrole Derivatives with a Substituted Spirocyclohexyl Group," *Biosci. Biotechnol. Biochem.* 67:1230-1238, Japan Society for Bioscience, Biotechnology, and Agrochemistry (2003).

Ito, M., et al., "Synthesis and Insecticidal Activity of *N*-Oxydihydropyrroles: 4-Hydroxy-3-mesityl-1-methoxymethoxy Derivatives with Various Substituents at the 5-Position," *Bioorg. Med. Chem.* 11:761-768, Elsevier Science Ltd. (2003).

Munday, L., "Amino-acids of the Cyclohexane Series. Part I.," *J. Chem. Soc.*, pp. 4372-4379, Royal Society of Chemistry (1961).

Schmierer, R. and Mildenberger, H., "Cyclization of *N*-Acylalanine and *N*-Acylglycine Esters," *Liebigs Ann. Chem.* 1985:1095-1098, VCH Verlagsgesellschaft mbH (1985).

Sonntag, N.O.V., "The Reactions of Aliphatic Acid Chlorides," *Chem. Rev.* 52:237-416, American Chemical Society (1953).

Suzuki, S., et al., "Studies on Antiviral Agents. IV. Biological Activity of Tenuazonic Acid Derivatives," *Chem. Pharm. Bull.* 15:1120-1122, Pharmaceutical Society of Japan (1967).

Esp@cenet Database, English language abstract of EP 0346620 A1 (listed as document FP8 on accompanying form PTO/SB/08A).

Dialog File 351, Derwent WPI English language abstract for JP 2000-053670 A (listed as document FP38 on accompanying form PTO/SB/08A).

Esp@cenet Database, English language abstract of JP 2002-205984 A (listed as document FP39 on accompanying form PTO/SB/08A).

International Search Report for International Application No. PCT/EP2007/004551, European Patent Office, Netherlands, mailed on Oct. 2, 2007, Search completed on Sep. 24, 2007.

English language translation of document FP89, WO 03/059065.

Office Action mailed Jun. 26, 2001, in U.S. Appl. No. 09/623,016, Lieb et al., filed Oct. 23, 2000.

Office Action mailed Jun. 26, 2001, in U.S. Appl. No. 09/646,722, Lieb et al., filed Jan. 2, 2001.

Office Action mailed Jul. 30, 2001, in U.S. Appl. No. 09/673,907, Lieb et al., filed Jan. 2, 2001.

Office Action mailed Nov. 9, 2007, in U.S. Appl. No. 10/485,909, Fischer et al., filed Aug. 6, 2004.

Office Action mailed Aug. 6, 2010, in U.S. Appl. No. 12/297,957, Fischer et al., filed Feb. 4, 2009.

Office Action mailed Feb. 4, 2011, in U.S. Appl. No. 12/267,957, Fischer et al., filed Feb. 4, 2009.

Office Action mailed Jun. 9, 2011, in U.S. Appl. No. 12/297,957, Fischer et al., filed Feb. 4, 2009.

Notice of Allowance mailed Aug. 9, 2011, in U.S. Appl. No. 12/297,957, Fischer et al., filed Feb. 4, 2009.

Office Action mailed Jun. 23, 2011, in U.S. Appl. No. 11/572,400, Fischer et al., filed Jul. 22, 2008.

\* cited by examiner

ALKOXYALKYL-SUBSTITUTED CYCLIC KETO-ENOLS

This application is a National Stage of International Application No. PCT/EP2007/004551, filed May 23, 2007, which claims the benefit of German Patent Application No. 10 2006 025 874.6, filed Jun. 2, 2006.

The present invention relates to new alkoxyalkyl-substituted cyclic ketoenols, to a number of processes for their preparation, and to their use as pesticides and/or herbicides and/or microbicides. Also subject matter of the invention are selectively herbicidal compositions which comprise alkoxyalkyl-substituted cyclic ketoenols on the one hand and a crop plant tolerance promoter compound on the other.

The present invention further relates to the boosting of the action of crop protection compositions comprising, in particular, alkoxyalkyl-substituted cyclic ketoenols, through the addition of ammonium salts or phosphonium salts and optionally penetrants, to the corresponding compositions, to processes for producing them and to their application in crop protection as insecticides and/or acaricides and/or for preventing unwanted plant growth.

For 3-acylpyrrolidine-2,4-diones pharmaceutical properties have been previously described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). Biological activity of these compounds has not been described.

EP-A-0 262 399 and GB-A-2 266 888 disclose similarly structured compounds (3-arylpyrrolidine-2,4-diones) for which, however, no herbicidal, insecticidal or acaricidal action has been disclosed. Known compounds with herbicidal, insecticidal or acaricidal action are unsubstituted, bicyclic 3-arylpyrrolidine-2,4-dione derivatives (EP-A-355 599, EP-A-415 211 and JP-A-12-053 670) and also substituted monocyclic 3-arylpyrrolidine-2,4-dione derivatives (EP-A-377 893 and EP-A-442 077).

Additionally known are polycyclic 3-arylpyrrolidine-2,4-dione derivatives (EP-A-442 073) and also 1H-arylpyrrolidinedione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869 and WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049596, WO 05/066125, WO 05/092897, WO 06/000355, WO 06/029799, WO 06/056281, WO 06/056282, WO 06/089633 and DE-A-05051325). Moreover, ketal-substituted 1-H-arylpyrrolidine-2,4-diones are known from WO 99/16748, and (spiro)ketal-substituted N-alkoxyalkoxy-substituted arylpyrrolidinediones are known from JP-A-14 205 984 and Ito M. et al., Bioscience, Biotechnology and Biochemistry 67, 1230-1238, (2003).

The herbicidal and/or acaricidal and/or insecticidal activity and/or breadth of action and/or the plant tolerance of the known compounds, particularly with respect to crop plants, is nevertheless not always sufficient.

New compounds of the formula (I) have now been found (I)

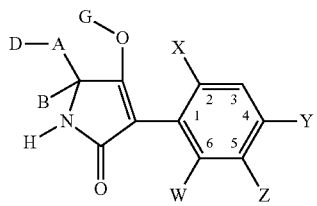

in which
W represents hydrogen, alkyl, alkenyl, alkynyl, halogen, alkoxy, alkenyloxy, haloalkyl, haloalkoxy or cyano,
X represents halogen, alkyl, alkenyl, alkynyl, alkoxy, alkenyloxy, alkylthio, alkylsulphinyl, alkylsulphonyl, haloalkyl, haloalkoxy, haloalkenyloxy, nitro or cyano,
Y and Z independently of one another represent hydrogen, alkyl, alkenyl, alkynyl, alkoxy, halogen, haloalkyl, haloalkoxy, cyano, nitro or in each case optionally substituted aryl or hetaryl,
  with the proviso that one of the radicals, Y or Z, represents in each case optionally substituted aryl or hetaryl,
A represents a $C_1$-$C_6$-alkanediyl radical,
B represents hydrogen, alkyl or alkoxyalkyl,
D represents in each case optionally substituted alkoxy, alkenyloxy, alkynyloxy, alkoxyalkoxy, phenoxy, hetaryloxy, phenylalkoxy, hetarylalkoxy and represents optionally substituted, saturated or unsaturated cycloalkyl interrupted by one or optionally two oxygen atoms
or
A represents a bond,
B represents hydrogen or alkyl,
D represents optionally substituted, saturated or unsaturated $C_5$-$C_6$-cycloalkyl interrupted by one or optionally two oxygen atoms,
G represents hydrogen (a) or represents one of the groups (b)
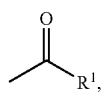

(c)
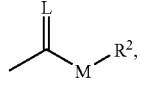

(d)
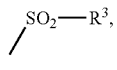

(e)
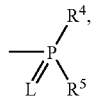

E, or (f)

(g)
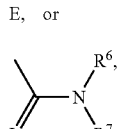

in which
E represents a metal ion or an ammonium ion,
L represents oxygen or sulphur,
M represents oxygen or sulphur, R[1] represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, R[2] represents in each case optionally halogen- or cyano-substituted alkyl, alkenyl, alkoxyalkyl or polyalkoxyalkyl or represents in each case optionally substituted cycloalkyl, phenyl or benzyl, R[3], R[4] and R[5] independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, R[6] and R[7] independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or, together with the N atom to which they are attached, form a ring system which optionally contains oxygen or sulphur and is optionally substituted.

The compounds of the formula (I), in dependence inter alia on the nature of the substituents, may be present in the form of optical isomers or isomer mixtures, in different compositions, which if desired may be separated in a conventional manner. Not only the pure isomers but also the isomer mixtures, their preparation and use, and compositions comprising them are subject matter of the present invention. In the text below, however, for the sake of simplicity, reference will always be made to compounds of the formula (I), although this covers not only the pure compounds but also, where appropriate, mixtures with different fractions of isomeric compounds.

Including the various definitions (a), (b), (c), (d), (e), (f) and (g) of the group G produces the following primary structures (I-a) to (I-g),

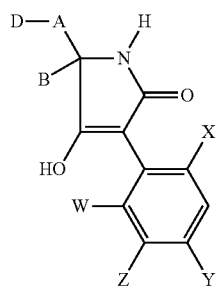
(I-a)

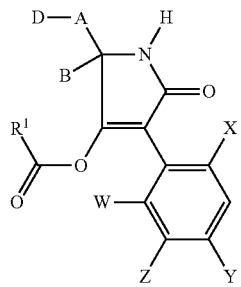
(I-b)

-continued

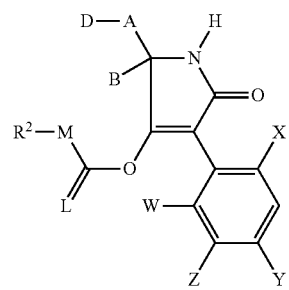
(I-c)

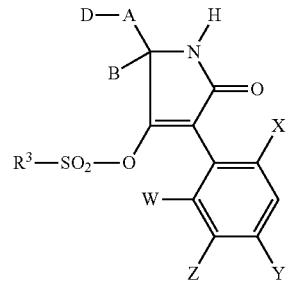
(I-d)

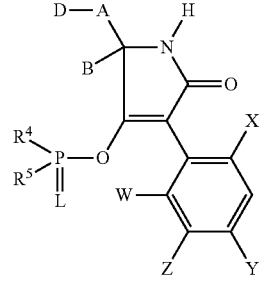
(I-e)

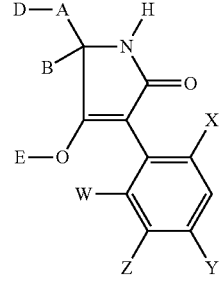
(I-f)

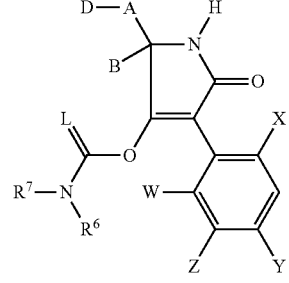
(I-g)

in which

A, B, D, E, L, M, W, X, Y, Z, R[1], R[2], R[3], R[4], R[5], R[6] and R[7] possess the definitions indicated above.

In addition it has been found that the new compounds of the formula (I) are obtained by the processes described below:

(A) compounds of the formula (I-a)

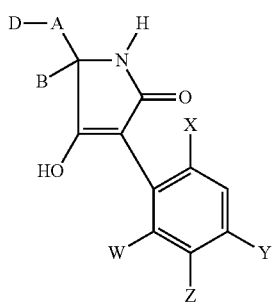

in which
A, B, D, W, X, Y and Z have the definitions indicated above
are obtained if
compounds of the formula (II)

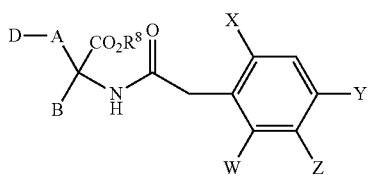

in which
A, B, D, W, X, Y and Z have the definitions indicated above
and
$R^8$ represents alkyl (preferably $C_1$-$C_6$-alkyl)
are subjected to intramolecular condensation in the presence of a diluent and in the presence of a base.

Moreover, it has been found (B) that the compounds of the above-shown formula (I-b) in which $R^1$, A, B, D, W, X, Y and Z have the definitions indicated above are obtained if compounds of the above-shown formula (I-a) in which A, B, D, W, X, Y and Z have the definitions indicated above are subjected to reaction respectively α) with compounds of the formula (III)

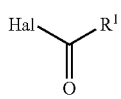

in which
$R^1$ has the definition indicated above and
Hal represents halogen (especially chlorine or bromine)
or
β) with carboxylic anhydrides of the formula (IV)

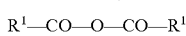 (IV)

in which
$R^1$ has the definition indicated above,
optionally in the presence of a diluent and optionally in the presence of an acid-binding agent;

(C) that the compounds of the above-shown formula (I-c) in which $R^2$, A, B, D, W, M, X, Y and Z have the definitions indicated above and L represents oxygen are obtained if compounds of the above-shown formula (I-a) in which A, B, D, W, X, Y and Z have the definitions indicated above are subjected to reaction respectively
with chloroformic esters or chloroformic thioesters of the formula (V)

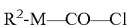 (V)

in which
$R^2$ and M have the definitions indicated above,
optionally in the presence of a diluent and optionally in the presence of an acid-binding agent;

(D) that compounds of the above-shown formula (I-c) in which $R^2$, A, B, D, W, M, X, Y and Z have the definitions indicated above and L represents sulphur are obtained if compounds of the above-shown formula (I-a) in which A, B, D, W, X, Y and Z have the definitions indicated above are subjected to reaction respectively
with chloromonothioformic esters or chlorodithioformic esters of the formula (VI)

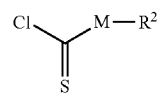

in which
M and $R^2$ have the definitions indicated above,
optionally in the presence of a diluent and optionally in the presence of an acid-binding agent;

(E) that compounds of the above-shown formula (I-d) in which $R^3$, A, B, D, W, X, Y and Z have the definitions indicated above are obtained if compounds of the above-shown formula (I-a) in which A, B, D, W, X, Y and Z have the definitions indicated above are subjected to reaction respectively
with sulphonyl chlorides of the formula (VII)

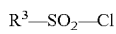 (VII)

in which
$R^3$ has the definition indicated above,
optionally in the presence of a diluent and optionally in the presence of an acid-binding agent;

(F) that compounds of the above-shown formula (I-e) in which L, $R^4$, $R^5$, A, B, D, W, X, Y and Z have the definitions indicated above are obtained if compounds of the above-shown formula (I-a) in which A, B, D, W, X, Y and Z have the definitions indicated above are subjected to reaction respectively
with phosphorus compounds of the formula (VII)

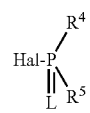

in which
L, $R^4$ and $R^5$ have the definitions indicated above and
Hal represents halogen (especially chlorine or bromine),
optionally in the presence of a diluent and optionally in the presence of an acid-binding agent;

(G) that compounds of the above-shown formula (I-f) in which E, A, B, D, W, X, Y and Z have the definitions indicated above are obtained if compounds of the formula (I-a) in which A, B, D, W, X, Y and Z have the definitions indicated above are subjected to reaction respectively with metal compounds or amines of the formulae (IX) or (X)

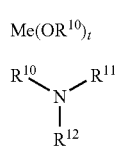

in which
Me represents a monovalent or divalent metal (preferably an alkali metal or alkaline earth metal such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl),
optionally in the presence of a diluent;
(H) that compounds of the above-shown formula (I-g) in which L, $R^6$, $R^7$, A, B, D, W, X, Y and Z have the definitions indicated above are obtained if compounds of the above-shown formula (I-a) in which A, B, D, W, X, Y and Z have the definitions indicated above are subjected to reaction respectively
α) with isocyanates or isothiocyanates of the formula (XI)

in which
$R^6$ and L have the definitions indicated above,
optionally in the presence of a diluent and optionally in the presence of a catalyst, or
β) with carbamoyl chlorides or thiocarbamoyl chlorides of the formula (XII)

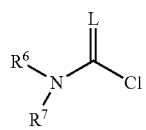

in which
L, $R^6$ and $R^7$ have the definitions indicated above,
optionally in the presence of a diluent and optionally in the presence of an acid-binding agent;
(Iα) that compounds of the above-shown formulae (I-a) to (I-g) in which A, B, D, G, W, X, Y and Z have the definition indicated above are obtained if compounds of the formulae (I-a') to (I-g') in which A, B, D, G, W, X and Y have the definition stated above and Z' preferably represents bromine or iodine

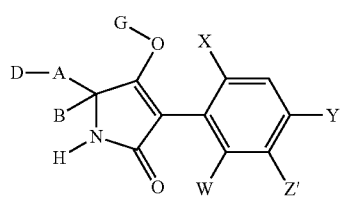

and
(Iβ) that compounds of the above-shown formulae (I-a) to (I-g) in which A, B, D, G, W, X, Y and Z have the definition indicated above are obtained if compounds of the formulae (I-a") to (I-g") in which A, B, D, G, W, X and Z have the definition stated above and Y' preferably represents bromine or iodine

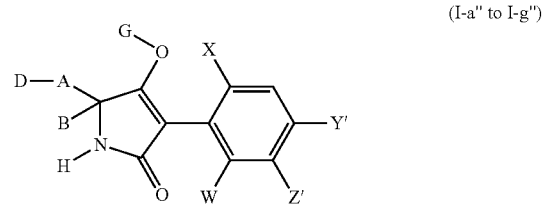

are subjected to coupling with couplable (Het)aryl derivatives, e.g. phenylboronic acids of the formulae (XIXα) and (XIXβ)

or esters thereof in the presence of a solvent, in the presence of a catalyst (e.g. Pd complexes) and in the presence of a base (e.g. sodium carbonate, potassium phosphate).

The following compounds of the formula (I-a) have been disclosed in the context of the European patent examination proceedings relating to EP-A-835 243 and EP-A-837 847.

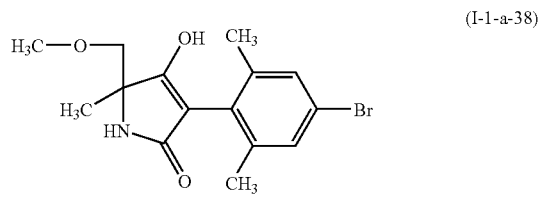

EP-A-835 243

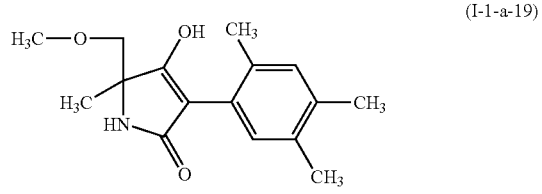

EP-A-837 847

In addition it has been found that the new compounds of the formula (I) exhibit good activity as pesticides, preferably as insecticides and/or acaricides and/or fungicides and/or herbicides, and, furthermore, are frequently very well tolerated by plants, in particular by crop plants.

Surprisingly it has now also been found that certain substituted cyclic ketoenols, when employed together with the crop plant tolerance promoter compounds (safeners/antidotes) described later on, are extremely good at preventing damage to the crop plants and can be used with particular advantage as broad-spectrum combination products for the selective control of unwanted plants in crops of utility plants, such as in cereals but also in maize, soya and rice, for example.

The invention also provides selective-herbicidal compositions comprising an effective amount of an active-compound combination comprising as components (a') at least one compound of the formula (I), in which A, B, D, G, W, X, Y and Z have the definition indicated above and (b') at least one crop plant tolerance promoter compound from the following group of compounds:

4-dichloroacetyl-1-oxa-4-azaspiro[4.5]decane (AD-67, MON-4660), 1-dichloroacetyl-hexa-hydro-3,3,8a-trimethylpyrrolo[1,2-a]pyrimidin-6(2H)one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoxyimino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenyl-acetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoxyimino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)-butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxy-acetate, 4-allyloxybutyl 5-chloroquinoline-8-oxyacetate, 1-allyl-oxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloro-quinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)-phenyl]-3-methylurea (also known as N-(2-methoxybenzoyl)-4-[(methylaminocarbonyl)-amino]benzenesulphonamide), 1-[4-(N-2-methoxybenzoylsulphamoyl)phenyl]-3,3-di-methylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclo-propylaminocarbonyl)benzenesulphonamide, and/or one of the following compounds, defined by general formulae, of the general formula (IIa)

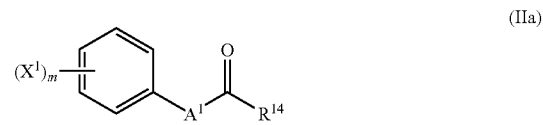

(IIa)

or of the general formula (IIb)

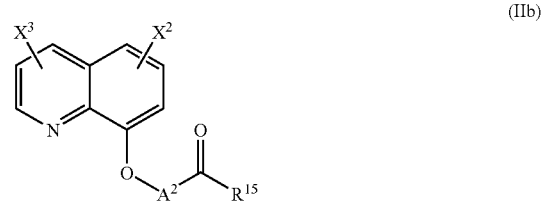

(IIb)

or of the formula (IIc)

(IIc)

where m represents a number 0, 1, 2, 3, 4 or 5, $A^1$ represents one of the divalent heterocyclic groupings shown below

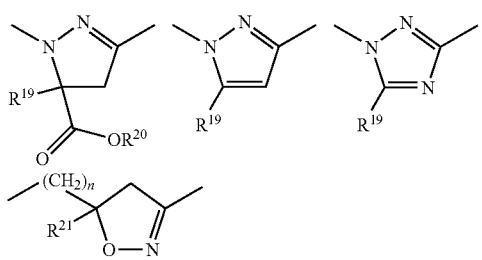

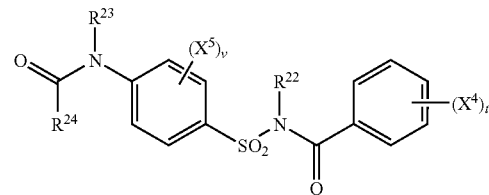

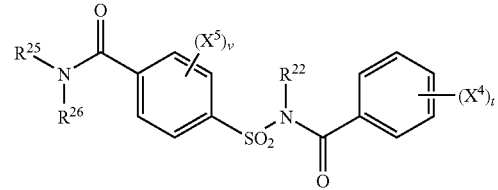

n represents a number 0, 1, 2, 3, 4 or 5, $A^2$ represents optionally $C_1$-$C_4$-alkyl- and/or $C_1$-$C_4$-alkoxycarbonyl- and/or $C_1$-$C_4$-alkenyloxycarbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkyl-amino or di($C_1$-$C_4$-alkyl)amino, $R^{15}$ represents hydroxyl, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)amino, $R^{16}$ represents optionally fluorine-, chlorine- and/or bromine-substituted $C_1$-$C_4$-alkyl, $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, di-oxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ together also represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxy-, cyano-, halogen- or $C_1$-$C_4$-alkoxy-substituted $C_1$-$C_6$-alkyl, $C_3$-$C_6$-cycloalkyl or tri($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

or of the general formula (IIe)

where t represents a number 0, 1, 2, 3, 4 or 5, v represents a number 0, 1, 2, 3, 4 or 5, $R^{22}$ represents hydrogen or $C_2$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy.

A general definition of the compounds of the invention is given by the formula (I). Preferred substituents and ranges of the radicals listed in the formulae mentioned above and below are elucidated in the following text:

W preferably represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano, X preferably represents halogen, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro or cyano, Y and Z independently of one another preferably represent hydrogen, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or represent one of the (Het)aryl radicals

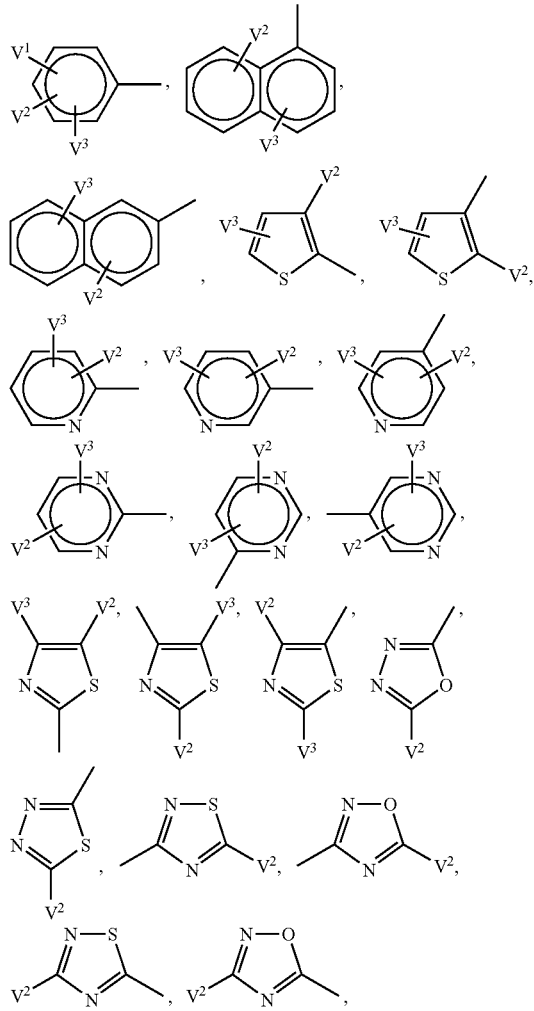

$V^1$ preferably represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, cyano or in each case optionally mono- or poly-halogen-, —$C_1$-$C_6$-alkyl-, —$C_1$-$C_6$-alkoxy-, —$C_1$-$C_4$-haloalkyl-, —$C_1$-$C_4$-haloalkoxy-, -nitro- or -cyano-substituted phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, $V^2$ and $V^3$ independently of one another preferably represent hydrogen, halogen, $C_1$-$C_6$-alkyl, $C_1$-$C_6$-alkoxy, $C_1$-$C_4$-haloalkyl or $C_1$-$C_4$-haloalkoxy, with the proviso that one of the radicals, Y or Z, represents one of the (Het)aryl radicals listed, A preferably represents a $C_1$-$C_6$-alkanediyl radical, B preferably represents hydrogen, $C_1$-$C_6$-alkyl or $C_1$-$C_4$-alkoxy-$C_1$-$C_4$-alkyl, D preferably represents in each case optionally mono- to poly-halogen- or -cyano-substituted $C_1$-$C_6$-alkoxy, $C_3$-$C_6$-alkenyloxy, $C_3$-$C_6$-alkynyloxy, $C_1$-$C_4$-alkoxy-$C_2$-$C_4$-alkoxy, represents in each case optionally mono- to tri-halogen-, —$C_1$-$C_6$-alkyl-, —$C_1$-$C_6$-alkoxy-, —$C_1$-$C_4$-haloalkyl-, —$C_1$-$C_4$-haloalkoxy-, -cyano- or -nitro-substituted phenoxy, pyridyloxy, pyrimidyloxy, pyrazolyloxy, thiazolyloxy, thienyloxy, phenyl-$C_1$-$C_4$-alkoxy, pyridyl-$C_1$-$C_4$-alkoxy, pyrimidyl-$C_1$-$C_4$-alkoxy, pyrazolyl-$C_1$-$C_4$-alkoxy, thienyl-$C_1$-$C_4$-alkoxy or represents optionally mono- to tri-halogen-, —$C_1$-$C_4$-alkyl-, —$C_1$-$C_4$-alkoxy-, —$C_1$-$C_4$-haloalkyl-substituted, saturated or unsaturated $C_3$-$C_8$-cycloalkyl interrupted by one or, optionally, two oxygen atoms, or A preferably represents a bond, B preferably represents hydrogen or $C_1$-$C_4$-alkyl, D preferably represents optionally mono- to tri-$C_1$-$C_2$-alkyl- or —$C_1$-$C_2$-alkoxy-substituted, saturated or unsaturated $C_3$-$C_8$-cycloalkyl interrupted by one or, optionally, two oxygen atoms, G preferably represents hydrogen (a) or represents one of the groups (b)
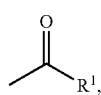

(c)
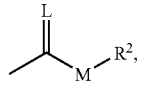

(d)
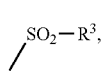

(e)

(f)
E, or (g)
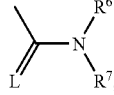

in which

E represents a metal ion or an ammonium ion,

L represents oxygen or sulphur and

M represents oxygen or sulphur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl, in which optionally one or two methylene groups not directly adjacent are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the series of oxygen, sulphur and nitrogen, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the series of oxygen, sulphur and nitrogen, $R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally a methylene group is replaced by oxygen or sulphur.

In the radical definitions stated as being preferable, halogen or halo represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X particularly preferably represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-haloalkyl, $C_1$-$C_4$-haloalkoxy or cyano, Y and Z independently of one another particularly preferably represent hydrogen, fluorine, chlorine, bromine, $C_1$-$C_4$-alkyl, $C_2$-$C_4$-alkenyl, $C_2$-$C_4$-alkynyl, $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or represent one of the (Het)aryl radicals

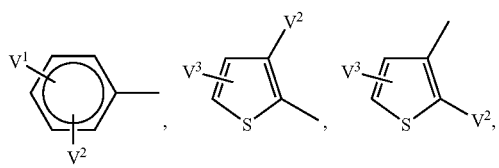

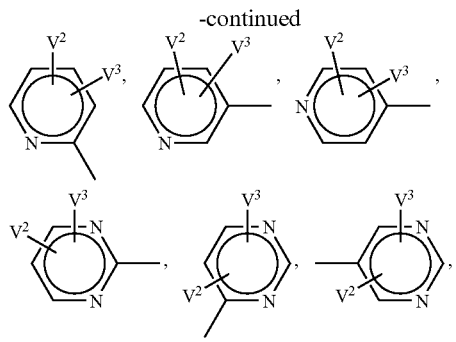

$V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or in each case optionally mono- to di-fluorine-, -chlorine-, -bromine-, —$C_1$-$C_4$-alkyl-, —$C_1$-$C_4$-alkoxy-, —$C_1$-$C_2$-haloalkyl-, —$C_1$-$C_2$-haloalkoxy-, -nitro- or -cyano-substituted phenyl, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, with the proviso that one of the radicals, Y or Z, represents one of the (Het)aryl radicals listed, A particularly preferably represents a $C_1$-$C_4$-alkanediyl radical, B particularly preferably represents hydrogen, $C_1$-$C_4$-alkyl or $C_1$-$C_4$-alkoxy-$C_1$-$C_2$-alkyl, D particularly preferably represents in each case optionally mono- to penta-fluorine-, -chlorine- or -cyano-substituted $C_1$-$C_4$-alkoxy, $C_3$-$C_6$-alkenyloxy, $C_3$-$C_6$-alkynyloxy, $C_1$-$C_3$-alkoxy-$C_2$-$C_3$-alkoxy, represents optionally mono- to di-fluorine-, -chlorine-, -bromine-, —$C_1$-$C_4$-alkyl-, —$C_1$-$C_4$-alkoxy-, -trifluoromethyl- or -trifluoromethoxy-substituted phenoxy or represents optionally mono- to di-fluorine-, -chlorine-, -methyl-, -ethyl-, -methoxy- or -trifluoromethyl-substituted, saturated $C_4$-$C_7$-cycloalkyl interrupted by one or, optionally, two oxygen atoms, or A particularly preferably represents a bond, B particularly preferably represents hydrogen or $C_1$-$C_2$-alkyl, D particularly preferably represents optionally mono- to di-methyl- or -ethyl-substituted, saturated $C_5$-$C_6$-cycloalkyl interrupted by one or, optionally, two oxygen atoms, G particularly preferably represents hydrogen (a) or represents one of the groups (b)

(c)

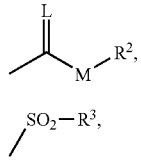

(d)

-continued

E, or

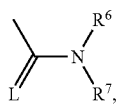

in which
E represents a metal ion or an ammonium ion,
L represents oxygen or sulphur and
M represents oxygen or sulphur, $R^1$ particularly preferably represents in each case optionally mono- to tri-fluorine- or -chlorine-substituted $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl or represents optionally mono- to di-fluorine-, -chlorine-, —$C_1$-$C_5$-alkyl- or —$C_1$-$C_5$-alkoxy-substituted $C_3$-$C_7$-cycloalkyl in which optionally one or two methylene groups not directly adjacent are replaced by oxygen and/or sulphur, represents optionally mono- to tri-fluorine-, -chlorine-, -bromine-, -cyano-, -nitro-, —$C_1$-$C_4$-alkyl-, —$C_1$-$C_4$-alkoxy-, —$C_1$-$C_3$-haloalkyl-, —$C_1$-$C_3$-haloalkoxy-, —$C_1$-$C_4$-alkylthio- or —$C_1$-$C_4$-alkylsulphonyl-substituted phenyl, represents optionally mono- to di-fluorine-, -chlorine-, -bromine-, —$C_1$-$C_4$-alkyl-, —$C_1$-$C_4$-alkoxy-, —$C_1$-$C_3$-haloalkyl- or —$C_1$-$C_3$-haloalkoxy-substituted phenyl-$C_1$-$C_4$-alkyl, represents in each case optionally mono- to di-fluorine-, -chlorine-, -bromine- or —$C_1$-$C_4$-alkyl-substituted pyrazolyl, thiazolyl, pyridyl, pyrimidyl, furanyl or thienyl, represents optionally mono- to di-fluorine-, -chlorine-, -bromine- or —$C_1$-$C_4$-alkyl-substituted phenoxy-$C_1$-$C_5$-alkyl or represents in each case optionally mono- to di-fluorine-, -chlorine-, -bromine-, -amino- or —$C_1$-$C_4$-alkyl-substituted pyridyloxy-$C_1$-$C_5$-alkyl, pyrimidyloxy-$C_1$-$C_5$-alkyl or thiazolyloxy-$C_1$-$C_5$-alkyl, $R^2$ particularly preferably represents in each case optionally mono- to tri-fluorine- or -chlorine-substituted $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, represents optionally mono- to di-fluorine-, -chlorine-, —$C_1$-$C_4$-alkyl- or —$C_1$-$C_4$-alkoxy-substituted $C_3$-$C_7$-cycloalkyl or represents in each case optionally mono- to tri-fluorine-, -chlorine-, -bromine-, -cyano-, -nitro-, —$C_1$-$C_4$-alkyl-, —$C_1$-$C_3$-alkoxy-, —$C_1$-$C_3$-haloalkyl- or —$C_1$-$C_3$-haloalkoxy-substituted phenyl or benzyl, $R^3$ particularly preferably represents optionally mono- to tri-fluorine- or -chlorine-substituted $C_1$-$C_6$-alkyl or in each case optionally mono- to di-fluorine-, -chlorine-, -bromine-, —$C_1$-$C_4$-alkyl-, —$C_1$-$C_4$-alkoxy-, —$C_1$-$C_2$-haloalkoxy-, —$C_1$-$C_2$-haloalkyl-, -cyano- or -nitro-substituted phenyl or benzyl, $R^4$ and $R^5$ independently of one another particularly preferably represent in each case optionally mono- to tri-fluorine- or -chlorine-substituted $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio or represent in each case optionally mono- to di-fluorine-, -chlorine-, -bromine-, -nitro-, -cyano-, —$C_1$-$C_3$-alkoxy-, —$C_1$-$C_3$-haloalkoxy-, —$C_1$-$C_3$-alkylthio-, —$C_1$-$C_3$-haloalkylthio-, —$C_1$-$C_3$-alkyl- or —$C_1$-$C_3$-haloalkyl-substituted phenyl, phenoxy or phenylthio, $R^6$ and $R^7$ independently of one another particularly preferably represent hydrogen, represent in each case optionally mono- to tri-fluorine- or -chlorine-substituted $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, represent in each case optionally mono- to tri-fluorine-, -chlorine-, -bromine-, —$C_1$-$C_5$-haloalkyl-, —$C_1$-$C_5$-alkyl- or —$C_1$-$C_5$-alkoxy-substituted phenyl or benzyl, or together represent an optionally $C_1$-$C_4$-alkyl-substituted $C_3$-$C_6$-alkylene radical in which optionally a methylene group is replaced by oxygen or sulphur.

In the radical definitions stated as being particularly preferable, halogen or halo represents fluorine, chlorine and bromine, in particular fluorine and chlorine.

W very preferably represents hydrogen, chlorine, bromine, methyl, ethyl, methoxy, ethoxy or trifluoromethyl, X very preferably represents chlorine, bromine, methyl, ethyl, propyl, methoxy, ethoxy, trifluoromethyl, difluoromethoxy, trifluoromethoxy or cyano, Y and Z independently of one another very preferably represent hydrogen, fluorine, chlorine, bromine, methyl, ethyl, methoxy, trifluoromethyl, trifluoromethoxy, cyano or a phenyl radical,

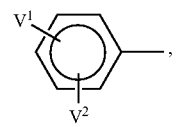

$V^1$ very preferably represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ very preferably represents hydrogen, fluorine, chlorine, methyl, ethyl, n-propyl, isopropyl, methoxy, ethoxy or trifluoromethyl,
with the proviso that one of the radicals, Y or Z, represents an optionally substituted phenyl radical, A very preferably represents
—CH$_2$—, —CH$_2$—CH$_2$—, —CH$_2$—CH$_2$—CH$_2$—, —CH$_2$—CHCH$_3$—, —CHCH$_3$—CH$_2$—, —CH$_2$—C(CH$_3$)$_2$—, —C(CH$_3$)$_2$—CH$_2$—, B very preferably represents hydrogen, methyl or ethyl, D very preferably represents methoxy, ethoxy, propoxy, isopropoxy, butoxy, isobutoxy, allyloxy, methallyloxy, isoprenyloxy, propargyloxy, butenyloxy, methoxyethoxy, ethoxyethoxy, represents phenoxy optionally monosubstituted by fluorine, chlorine, bromine, methyl, methoxy, trifluoromethyl or trifluoromethoxy, or represents in each case optionally mono- to di-methyl-substituted tetrahydrofuranyl, tetrahydropyranyl, dioxolanyl or dioxanyl, or A very preferably represents a bond, B very preferably represents hydrogen, methyl or ethyl, D very preferably represents tetrahydrofuranyl, tetrahydropyranyl, dioxolanyl or dioxanyl, G very preferably represents hydrogen (a) or represents one of the groups (b)

$$\underset{R^1}{\overset{O}{\bigwedge}}$$

(c)

$$\underset{M}{\overset{L}{\bigwedge}}R^2,$$

(d)

$$/SO_2-R^3,$$

(e)

$$-\overset{R^4}{\underset{L}{\overset{P}{\bigwedge}}}R^5$$

E, or (f)

(g)

$$\underset{L}{\overset{R^6}{\bigwedge}}\underset{R^7}{\overset{N}{\bigwedge}},$$

in which

E represents a metal ion or an ammonium ion,
L represents oxygen or sulphur and
M represents oxygen or sulphur, $R^1$ very preferably represents in each case optionally mono- to tri-fluorine- or -chlorine-substituted $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl or represents $C_3$-$C_6$-cycloalkyl optionally monosubstituted by fluorine, chlorine, methyl, ethyl or methoxy, represents optionally mono- to di-fluorine-, -chlorine-, -bromine-, -cyano-, -nitro-, -methyl-, -ethyl-, -n-propyl-, -isopropyl-, -methoxy-, -ethoxy-, -trifluoromethyl- or -trifluoromethoxy-substituted phenyl, represents furanyl, thienyl or pyridyl in each case optionally monosubstituted by chlorine, bromine or methyl, $R^2$ very preferably represents in each case optionally mono- to tri-fluorine- or -chlorine-substituted $C_1$-$C_{10}$-alkyl, $C_2$-$C_{10}$-alkenyl or $C_1$-$C_4$-alkoxy-$C_2$-$C_4$-alkyl, represents cyclopentyl or cyclohexyl or represents in each case optionally mono- to di-fluorine-, -chlorine-, -cyano-, -nitro-, -methyl-, -ethyl-, -methoxy-, -trifluoromethyl- or -trifluoromethoxy-substituted phenyl or benzyl, $R^3$ very preferably represents in each case optionally mono- to tri-fluorine- or -chlorine-substituted methyl, ethyl, propyl or isopropyl, or phenyl in each case optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another very preferably represent $C_1$-$C_4$-alkoxy or $C_1$-$C_4$-alkyl-thio or represent phenyl, phenoxy or phenylthio in each case optionally monosubstituted by fluorine, chlorine, bromine, nitro, cyano, methyl, methoxy, trifluoromethyl or trifluoromethoxy, $R^6$ and $R^7$ independently of one another very preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent in each case optionally mono- to di-fluorine-, -chlorine-, -bromine-, -methyl-, -methoxy- or -trifluoromethyl-substituted phenyl, or together represent a $C_5$-$C_6$-alkylene radical in which optionally a methylene group is replaced by oxygen or sulphur.

W notably represents hydrogen, methyl or ethyl,
X notably represents chlorine, methyl or ethyl,
Y and Z independently of one another notably represent hydrogen or one of the following phenyl radicals with the proviso that one of the radicals, Y or Z, represents an optionally substituted phenyl radical, A notably represents
—$CH_2$— or —$CH_2$—$CH_2$—, B notably represents methyl,
D notably represents methoxy or tetrahydrofuranyl,
or
A notably represents a bond,
B notably represents methyl or ethyl,
D notably represents tetrahydrofuranyl,
G notably represents hydrogen (a) or represents one of the groups (b)

$$\underset{R^1}{\overset{O}{\bigwedge}},$$

(c)

$$\underset{O}{\overset{O}{\bigwedge}}R^2$$

in which $R^1$ notably represents $C_1$-$C_{10}$-alkyl, $C_1$-$C_4$-alkoxy-$C_1$-$C_2$-alkyl, cyclopropyl or
represents phenyl optionally monosubstituted by chlorine, $R^2$ notably represents $C_1$-$C_{10}$-alkyl or benzyl.

The general radical definitions and/or elucidations set out above, or those set out in ranges of preference, can be combined with one another arbitrarily, i.e. including combinations between the respective ranges and ranges of preference. They apply to the end products and also to the precursors and intermediates correspondingly.

Preference in accordance with the invention is given to the compounds of the formula (I) in which there is a combination of the definitions set out above as being preferred (preferable).

Particular preference in accordance with the invention is given to the compounds of the formula (I) in which there is a combination of the definitions set out above as being particularly preferred.

Very particular preference is given in accordance with the invention to the compounds of the formula (I) in which there is a combination of the definitions set out above as being very preferred.

Noteworthiness in accordance with the invention is accorded to the compounds of the formula (I) in which there is a combination of the definitions set out above as being notable.

Compounds of the formula (I) in which G represents hydrogen are notable.

Saturated or unsaturated hydrocarbon radicals such as alkyl, alkanediyl or alkenyl, both alone and in conjunction with heteroatoms, such as in alkoxy, for example, can as far as possible be straight-chain or branched in each case.

Optionally substituted radicals can be substituted one or more times unless indicated otherwise, and in the case of multiple substitutions the substituents can be identical or different.

Specifically, as well as the compounds specified in the Preparation Examples, mention may be made of the following compounds of the formula (I-1-a):

TABLE 1

(I-a)

| A | B | D | X | W | Y | Z |
|---|---|---|---|---|---|---|
| —CH$_2$— | CH$_3$ | OCH$_3$ | CH$_3$ | CH$_3$ | 4-Cl—C$_6$H$_4$ | H |
| —CH$_2$— | CH$_3$ | OCH$_3$ | C$_2$H$_5$ | CH$_3$ | 4-Cl—C$_6$H$_4$ | H |
| —CH$_2$— | CH$_3$ | OCH$_3$ | C$_2$H$_5$ | C$_2$H$_5$ | 4-Cl—C$_6$H$_4$ | H |
| —CH$_2$— | CH$_3$ | OCH$_3$ | Cl | CH$_3$ | 4-Cl—C$_6$H$_4$ | H |
| —CH$_2$— | CH$_3$ | OCH$_3$ | Cl | C$_2$H$_5$ | 4-Cl—C$_6$H$_4$ | H |
| —CH$_2$— | CH$_3$ | OCH$_3$ | CH$_3$ | H | H | 4-Cl—C$_6$H$_4$ |
| —CH$_2$— | CH$_3$ | OCH$_3$ | CH$_3$ | CH$_3$ | H | 4-Cl—C$_6$H$_4$ |
| —CH$_2$— | CH$_3$ | OCH$_3$ | CH$_3$ | H | CH$_3$ | 4-Cl—C$_6$H$_4$ |
| —CH$_2$— | CH$_3$ | OCH$_3$ | CH$_3$ | CH$_3$ | CH$_3$ | 4-Cl—C$_6$H$_4$ |
| —CH$_2$— | CH$_3$ | OCH$_3$ | Cl | H | H | 4-Cl—C$_6$H$_4$ |
| —CH$_2$— | CH$_3$ | OCH$_3$ | CH$_3$ | H | H | 4-F—C$_6$H$_4$ |
| —CH$_2$— | CH$_3$ | OCH$_3$ | CH$_3$ | H | H | 4-CH$_3$—C$_6$H$_4$ |
| —CH$_2$— | CH$_3$ | OCH$_3$ | CH$_3$ | H | H | 4-OCH$_3$—C$_6$H$_4$ |
| —CH$_2$— | CH$_3$ | OCH$_3$ | CH$_3$ | H | H | 4-OCF$_3$—C$_6$H$_4$ |
| —CH$_2$— | CH$_3$ | OCH$_3$ | CH$_3$ | H | H | 4-CF$_3$—C$_6$H$_4$ |
| —CH$_2$— | CH$_3$ | OCH$_3$ | CH$_3$ | H | H | 3-Cl—C$_6$H$_4$ |
| —CH$_2$— | CH$_3$ | OCH$_3$ | CH$_3$ | H | H | 3-F—C$_6$H$_4$ |
| —CH$_2$— | CH$_3$ | OCH$_3$ | CH$_3$ | H | H | 3-OCH$_3$—C$_6$H$_4$ |
| —CH$_2$— | CH$_3$ | OCH$_3$ | CH$_3$ | H | H | 3-CF$_3$—C$_6$H$_4$ |
| —CH$_2$— | CH$_3$ | OCH$_3$ | CH$_3$ | H | H | 3,4-F$_2$—C$_6$H$_3$ |
| —CH$_2$— | CH$_3$ | OCH$_3$ | CH$_3$ | H | H | 3,4-Cl$_2$—C$_6$H$_3$ |
| —CH$_2$— | CH$_3$ | OCH$_3$ | CH$_3$ | H | H | 3-F,4-Cl—C$_6$H$_3$ |
| —CH$_2$— | CH$_3$ | OCH$_3$ | CH$_3$ | H | H | 4-Cl,3-F—C$_6$H$_3$ |
| —CH$_2$— | CH$_3$ | OCH$_3$ | CH$_3$ | H | H | 4-CF$_3$-3-F—C$_6$H$_3$ |
| —CH$_2$— | CH$_3$ | OCH$_3$ | CH$_3$ | H | H | 2,4-F$_2$—C$_6$H$_3$ |
| —CH$_2$— | CH$_3$ | OCH$_3$ | CH$_3$ | H | H | 3,5-F$_2$—C$_6$H$_3$ |
| —CH$_2$— | CH$_3$ | OCH$_3$ | CH$_3$ | H | H | 2,5-F$_2$—C$_6$H$_3$ |
| —CH$_2$— | CH$_3$ | OCH$_3$ | CH$_3$ | H | H | 3,4,5-F$_3$—C$_6$H$_2$ |
| —CH$_2$— | CH$_3$ | OCH$_3$ | CH$_3$ | CH$_3$ | H | 4-F—C$_6$H$_4$ |
| —CH$_2$— | CH$_3$ | OCH$_3$ | CH$_3$ | CH$_3$ | H | 4-CH$_3$—C$_6$H$_4$ |
| —CH$_2$— | CH$_3$ | OCH$_3$ | CH$_3$ | CH$_3$ | H | 4-OCH$_3$—C$_6$H$_4$ |
| —CH$_2$— | CH$_3$ | OCH$_3$ | CH$_3$ | H | H | 4-OCF$_3$—C$_6$H$_4$ |
| —CH$_2$— | CH$_3$ | OCH$_3$ | CH$_3$ | CH$_3$ | H | 4-CF$_3$—C$_6$H$_4$ |
| —CH$_2$— | CH$_3$ | OCH$_3$ | CH$_3$ | CH$_3$ | H | 3-Cl—C$_6$H$_4$ |
| —CH$_2$— | CH$_3$ | OCH$_3$ | CH$_3$ | CH$_3$ | H | 3-F—C$_6$H$_4$ |
| —CH$_2$— | CH$_3$ | OCH$_3$ | CH$_3$ | CH$_3$ | H | 3-OCH$_3$—C$_6$H$_4$ |
| —CH$_2$— | CH$_3$ | OCH$_3$ | CH$_3$ | CH$_3$ | H | 3-CF$_3$—C$_6$H$_2$ |
| —CH$_2$— | CH$_3$ | OCH$_3$ | CH$_3$ | CH$_3$ | H | 3,4-F$_2$—C$_6$H$_3$ |
| —CH$_2$— | CH$_3$ | OCH$_3$ | CH$_3$ | CH$_3$ | H | 3,4-Cl$_2$—C$_6$H$_3$ |
| —CH$_2$— | CH$_3$ | OCH$_3$ | CH$_3$ | CH$_3$ | H | 3-F,4-Cl—C$_6$H$_3$ |
| —CH$_2$— | CH$_3$ | OCH$_3$ | CH$_3$ | CH$_3$ | H | 4-Cl,3-F—C$_6$H$_3$ |
| —CH$_2$— | CH$_3$ | OCH$_3$ | CH$_3$ | CH$_3$ | H | 4-CF$_3$-3-F—C$_6$H$_3$ |
| —CH$_2$— | CH$_3$ | OCH$_3$ | CH$_3$ | CH$_3$ | H | 2,4-F$_2$—C$_6$H$_3$ |
| —CH$_2$— | CH$_3$ | OCH$_3$ | CH$_3$ | CH$_3$ | H | 3,5-F$_2$—C$_6$H$_3$ |
| —CH$_2$— | CH$_3$ | OCH$_3$ | CH$_3$ | CH$_3$ | H | 2,5-F$_2$—C$_6$H$_3$ |
| —CH$_2$— | CH$_3$ | OCH$_3$ | CH$_3$ | CH$_3$ | H | 3,4,5-F$_3$—C$_6$H$_2$ |
| —CH$_2$— | CH$_3$ | OCH$_3$ | Cl | H | H | 4-F—C$_6$H$_4$ |
| —CH$_2$— | CH$_3$ | OCH$_3$ | Cl | H | H | 4-CH$_3$—C$_6$H$_4$ |
| —CH$_2$— | CH$_3$ | OCH$_3$ | Cl | H | H | 4-OCH$_3$—C$_6$H$_4$ |
| —CH$_2$— | CH$_3$ | OCH$_3$ | Cl | H | H | 4-OCF$_3$—C$_6$H$_4$ |
| —CH$_2$— | CH$_3$ | OCH$_3$ | Cl | H | H | 4-CF$_3$—C$_6$H$_2$ |
| —CH$_2$— | CH$_3$ | OCH$_3$ | Cl | H | H | 3-Cl—C$_6$H$_4$ |
| —CH$_2$— | CH$_3$ | OCH$_3$ | Cl | H | H | 3-F—C$_6$H$_4$ |
| —CH$_2$— | CH$_3$ | OCH$_3$ | Cl | H | H | 3-OCH$_3$—C$_6$H$_4$ |

TABLE 1-continued

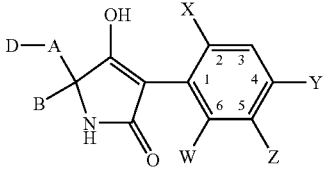

(I-a)

| A | B | D | X | W | Y | Z |
|---|---|---|---|---|---|---|
| —CH$_2$— | CH$_3$ | OCH$_3$ | Cl | H | H | 3-CF$_3$—C$_6$H$_4$ |
| —CH$_2$— | CH$_3$ | OCH$_3$ | Cl | H | H | 3,4-F$_2$—C$_6$H$_3$ |
| —CH$_2$— | CH$_3$ | OCH$_3$ | Cl | H | H | 3,4-Cl$_2$—C$_6$H$_3$ |
| —CH$_2$— | CH$_3$ | OCH$_3$ | Cl | H | H | 3-F,4-Cl—C$_6$H$_3$ |
| —CH$_2$— | CH$_3$ | OCH$_3$ | Cl | H | H | 4-Cl,3-F—C$_6$H$_3$ |
| —CH$_2$— | CH$_3$ | OCH$_3$ | Cl | H | H | 4-CF$_3$-3-F—C$_6$H$_3$ |
| —CH$_2$— | CH$_3$ | OCH$_3$ | Cl | H | H | 2,4-F$_2$—C$_6$H$_3$ |
| —CH$_2$— | CH$_3$ | OCH$_3$ | Cl | H | H | 3,5-F$_2$—C$_6$H$_3$ |
| —CH$_2$— | CH$_3$ | OCH$_3$ | Cl | H | H | 2,5-F$_2$—C$_6$H$_3$ |
| —CH$_2$— | CH$_3$ | OCH$_3$ | Cl | H | H | 3,4,5-F$_3$—C$_6$H$_2$ |
| —CH$_2$— | CH$_3$ | OCH$_3$ | CH$_3$ | H | 4-F—C$_6$H$_4$ | H |
| —CH$_2$— | CH$_3$ | OCH$_3$ | CH$_3$ | H | 4-CH$_3$—C$_6$H$_4$ | H |
| —CH$_2$— | CH$_3$ | OCH$_3$ | CH$_3$ | H | 4-OCH$_3$—C$_6$H$_4$ | H |
| —CH$_2$— | CH$_3$ | OCH$_3$ | CH$_3$ | H | 4-OCF$_3$—C$_6$H$_4$ | H |
| —CH$_2$— | CH$_3$ | OCH$_3$ | CH$_3$ | H | 4-CF$_3$—C$_6$H$_4$ | H |
| —CH$_2$— | CH$_3$ | OCH$_3$ | CH$_3$ | H | 3-Cl—C$_6$H$_4$ | H |
| —CH$_2$— | CH$_3$ | OCH$_3$ | CH$_3$ | H | 3-F—C$_6$H$_4$ | H |
| —CH$_2$— | CH$_3$ | OCH$_3$ | CH$_3$ | H | 3-OCH$_3$—C$_6$H$_4$ | H |
| —CH$_2$— | CH$_3$ | OCH$_3$ | CH$_3$ | H | 3-CF$_3$—C$_6$H$_4$ | H |
| —CH$_2$— | CH$_3$ | OCH$_3$ | CH$_3$ | H | 3,4-F$_2$—C$_6$H$_3$ | H |
| —CH$_2$— | CH$_3$ | OCH$_3$ | CH$_3$ | H | 3,4-Cl$_2$—C$_6$H$_3$ | H |
| —CH$_2$— | CH$_3$ | OCH$_3$ | CH$_3$ | H | 3-F,4-Cl—C$_6$H$_3$ | H |
| —CH$_2$— | CH$_3$ | OCH$_3$ | CH$_3$ | H | 4-Cl,3-F—C$_6$H$_3$ | H |
| —CH$_2$— | CH$_3$ | OCH$_3$ | CH$_3$ | H | 4-CF$_3$-3-F—C$_6$H$_3$ | H |
| —CH$_2$— | CH$_3$ | OCH$_3$ | CH$_3$ | H | 2,4-F$_2$—C$_6$H$_3$ | H |
| —CH$_2$— | CH$_3$ | OCH$_3$ | CH$_3$ | H | 3,5-F$_2$—C$_6$H$_3$ | H |
| —CH$_2$— | CH$_3$ | OCH$_3$ | CH$_3$ | H | 2,5-F$_2$—C$_6$H$_3$ | H |
| —CH$_2$— | CH$_3$ | OCH$_3$ | CH$_3$ | H | 3,4,5-F$_3$—C$_6$H$_2$ | H |
| —CH$_2$— | CH$_3$ | OCH$_3$ | CH$_3$ | CH$_3$ | 4-F—C$_6$H$_4$ | H |
| —CH$_2$— | CH$_3$ | OCH$_3$ | CH$_3$ | CH$_3$ | 4-CH$_3$—C$_6$H$_4$ | H |
| —CH$_2$— | CH$_3$ | OCH$_3$ | CH$_3$ | CH$_3$ | 4-OCH$_3$—C$_6$H$_4$ | H |
| —CH$_2$— | CH$_3$ | OCH$_3$ | CH$_3$ | CH$_3$ | 4-OCF$_3$—C$_6$H$_4$ | H |
| —CH$_2$— | CH$_3$ | OCH$_3$ | CH$_3$ | CH$_3$ | 4-CF$_3$—C$_6$H$_4$ | H |
| —CH$_2$— | CH$_3$ | OCH$_3$ | CH$_3$ | CH$_3$ | 3-Cl—C$_6$H$_4$ | H |
| —CH$_2$— | CH$_3$ | OCH$_3$ | CH$_3$ | CH$_3$ | 3-F—C$_6$H$_4$ | H |
| —CH$_2$— | CH$_3$ | OCH$_3$ | CH$_3$ | CH$_3$ | 3-OCH$_3$—C$_6$H$_4$ | H |
| —CH$_2$— | CH$_3$ | OCH$_3$ | CH$_3$ | CH$_3$ | 3-CF$_3$—C$_6$H$_4$ | H |
| —CH$_2$— | CH$_3$ | OCH$_3$ | CH$_3$ | CH$_3$ | 3,4-F$_2$—C$_6$H$_3$ | H |
| —CH$_2$— | CH$_3$ | OCH$_3$ | CH$_3$ | CH$_3$ | 3,4-Cl$_2$—C$_6$H$_3$ | H |
| —CH$_2$— | CH$_3$ | OCH$_3$ | CH$_3$ | CH$_3$ | 3-F,4-Cl—C$_6$H$_3$ | H |
| —CH$_2$— | CH$_3$ | OCH$_3$ | CH$_3$ | CH$_3$ | 4-Cl,3-F—C$_6$H$_3$ | H |
| —CH$_2$— | CH$_3$ | OCH$_3$ | CH$_3$ | CH$_3$ | 4-CF$_3$-3-F—C$_6$H$_3$ | H |
| —CH$_2$— | CH$_3$ | OCH$_3$ | CH$_3$ | CH$_3$ | 2,4-F$_2$—C$_6$H$_3$ | H |
| —CH$_2$— | CH$_3$ | OCH$_3$ | CH$_3$ | CH$_3$ | 3,5-F$_2$—C$_6$H$_3$ | H |
| —CH$_2$— | CH$_3$ | OCH$_3$ | CH$_3$ | CH$_3$ | 2,5-F$_2$—C$_6$H$_3$ | H |
| —CH$_2$— | CH$_3$ | OCH$_3$ | CH$_3$ | CH$_3$ | 3,4,5-F$_3$—C$_6$H$_2$ | H |
| —CH$_2$— | CH$_3$ | OCH$_3$ | Cl | H | 4-F—C$_6$H$_4$ | H |
| —CH$_2$— | CH$_3$ | OCH$_3$ | Cl | H | 4-CH$_3$—C$_6$H$_4$ | H |
| —CH$_2$— | CH$_3$ | OCH$_3$ | Cl | H | 4-OCH$_3$—C$_6$H$_4$ | H |
| —CH$_2$— | CH$_3$ | OCH$_3$ | Cl | H | 4-OCF$_3$—C$_6$H$_4$ | H |
| —CH$_2$— | CH$_3$ | OCH$_3$ | Cl | H | 4-CF$_3$—C$_6$H$_4$ | H |
| —CH$_2$— | CH$_3$ | OCH$_3$ | Cl | H | 3-Cl—C$_6$H$_4$ | H |
| —CH$_2$— | CH$_3$ | OCH$_3$ | Cl | H | 3-F—C$_6$H$_4$ | H |
| —CH$_2$— | CH$_3$ | OCH$_3$ | Cl | H | 3-OCH$_3$—C$_6$H$_4$ | H |
| —CH$_2$— | CH$_3$ | OCH$_3$ | Cl | H | 3-CF$_3$—C$_6$H$_4$ | H |
| —CH$_2$— | CH$_3$ | OCH$_3$ | Cl | H | 3,4-F$_2$—C$_6$H$_3$ | H |
| —CH$_2$— | CH$_3$ | OCH$_3$ | Cl | H | 3,4-Cl$_2$—C$_6$H$_3$ | H |
| —CH$_2$— | CH$_3$ | OCH$_3$ | Cl | H | 3-F,4-Cl—C$_6$H$_3$ | H |
| —CH$_2$— | CH$_3$ | OCH$_3$ | Cl | H | 4-Cl,3-F—C$_6$H$_3$ | H |
| —CH$_2$— | CH$_3$ | OCH$_3$ | Cl | H | 4-CF$_3$-3-F—C$_6$H$_3$ | H |
| —CH$_2$— | CH$_3$ | OCH$_3$ | Cl | H | 2,4-F$_2$—C$_6$H$_3$ | H |
| —CH$_2$— | CH$_3$ | OCH$_3$ | Cl | H | 3,5-F$_2$—C$_6$H$_3$ | H |
| —CH$_2$— | CH$_3$ | OCH$_3$ | Cl | H | 2,5-F$_2$—C$_6$H$_3$ | H |
| —CH$_2$— | CH$_3$ | OCH$_3$ | Cl | H | 3,4,5-F$_3$—C$_6$H$_2$ | H |

TABLE 2

| W, X, Y and Z as indicated in Table 1 |
|---|
| A = —CH$_2$—; B = CH$_3$, D = OC$_2$H$_5$ |

TABLE 3

| W, X, Y and Z as indicated in Table 1 |
|---|
| A = —CH$_2$—CH$_2$—; B = CH$_3$, D = O$_2$CH$_5$ |

TABLE 4

| W, X, Y and Z as indicated in Table 1 |
|---|
| A = —CH$_2$—CH$_2$—; B = CH$_3$, D = OC$_2$H$_5$ |

TABLE 5

| W, X, Y and Z as indicated in Table 1 |
|---|
| A = bond; B = CH$_3$, D = 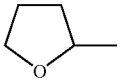 |

TABLE 6

| W, X, Y and Z as indicated in Table 1 |
|---|
| A = bond; B = CH$_3$, D = 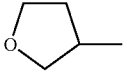 |

TABLE 7

| W, X, Y and Z as indicated in Table 1 |
|---|
| A = CH$_2$; B = CH$_3$, D = 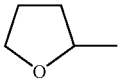 |

TABLE 8

| W, X, Y and Z as indicated in Table 1 |
|---|
| A = CH$_2$; B = CH$_3$, D = 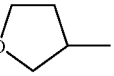 |

Preferred definitions of the groups listed above in connection with the crop plant tolerance promoter compounds (herbicide safeners) of the formulae (IIa), (IIb), (IIc), (IId) and (IIe) are defined below.

m preferably represents the numbers 0, 1, 2, 3 or 4.

A$^1$ preferably represents one of the divalent heterocyclic groupings shown below

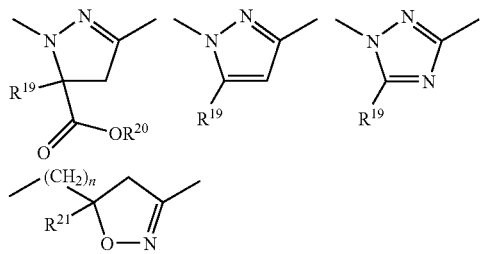

n preferably represents the numbers 0, 1, 2, 3 or 4.

A$^2$ preferably represents in each case optionally methyl-, ethyl-, methoxycarbonyl- or ethoxycarbonyl- or allyloxycarbonyl-substituted methylene or ethylene.

R$^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

R$^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

R$^{16}$ preferably represents in each case optionally fluorine-, chlorine- and/or bromine-substituted methyl, ethyl, n- or i-propyl.

R$^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl.

R$^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl, or together with R$^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

R$^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

R$^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

R$^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

X$^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2 or 3.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl (trimethylene), pentane-1,5-diyl, 1-oxabutane-1,4-diyl or 3-oxapentane-1,5-diyl.

$X^4$ preferably represents nitro, cyano, carboxy, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

(IIa)

| Example No. | (positions) $(X^1)_m$ | $A^1$ | $R^{14}$ |
|---|---|---|---|
| IIa-1 | (2) Cl, (4) Cl | | $OCH_3$ |
| IIa-2 | (2) Cl, (4) Cl | | $OCH_3$ |
| IIa-3 | (2) Cl, (4) Cl | | $OC_2H_5$ |
| IIa-4 | (2) Cl, (4) Cl | | $OC_2H_5$ |
| IIa-5 | (2) Cl | | $OCH_3$ |
| IIa-6 | (2) Cl, (4) Cl | | $OCH_3$ |

TABLE-continued

Examples of the compounds of the formula (IIa)

| Example No. | (positions) $(X^1)_m$ | $A^1$ | $R^{14}$ |
|---|---|---|---|
| IIa-7 | (2) F | 1,3-dimethyl-5-phenyl-pyrazol-yl | $OCH_3$ |
| IIa-8 | (2) F | 1,3-dimethyl-5-(2-chlorophenyl)-pyrazol-yl | $OCH_3$ |
| IIa-9 | (2) Cl, (4) Cl | 1-methyl-3-methyl-5-trichloromethyl-triazol-yl | $OC_2H_5$ |
| IIa-10 | (2) Cl, (4) $CF_3$ | 1-methyl-3-methyl-5-phenyl-triazol-yl | $OCH_3$ |
| IIa-11 | (2)Cl | 1,3-dimethyl-5-(2-fluorophenyl)-pyrazol-yl | $OCH_3$ |
| IIa-12 | — | 3-methyl-5-phenyl-isoxazoline-yl | $OC_2H_5$ |
| IIa-13 | (2) Cl, (4) Cl | 1,3-dimethyl-5-methyl-pyrazol-yl | $OC_2H_5$ |
| IIa-14 | (2) Cl, (4) Cl | 1,3-dimethyl-5-isopropyl-pyrazol-yl | $OC_2H_5$ |
| IIa-15 | (2) Cl, (4) Cl | 1,3-dimethyl-5-tert-butyl-pyrazol-yl | $OC_2H_5$ |
| IIa-16 | (2) Cl, (4) Cl | 3-methyl-isoxazoline-CH$_2$- | $OC_2H_5$ |
| IIa-17 | (2) Cl, (4) Cl | 3,5-dimethyl-isoxazoline-yl | $OC_2H_5$ |
| IIa-18 | — | 3-methyl-5-phenyl-isoxazoline-yl | OH |

Examples of the compounds of the formula (IIb) which are very particularly preferred as herbicide safeners according to the invention are listed in the table below.

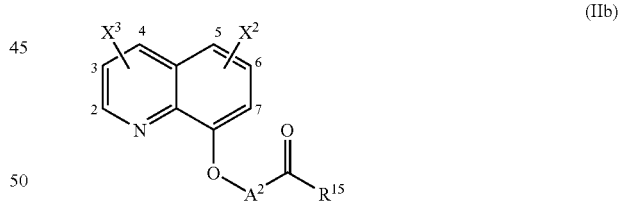

(IIb)

TABLE

Examples of the compounds of the formula (IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |

TABLE-continued

Examples of the compounds of the formula (IIb)

| Example No. | (Position) $X^2$ | (Position) $X^3$ | $A^2$ | $R^{15}$ |
|---|---|---|---|---|
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | (structure with $CH_2=CH-CH_2-O-CH_2-CH(CH_3)-O-$) |
| IIb-13 | (5) Cl | — | (ester structure) | $OCH_2CH=CH_2$ |
| IIb-14 | (5) Cl | — | (ester structure, $C_2H_5$) | $OC_2H_5$ |
| IIb-15 | (5) Cl | — | (ester structure, $CH_3$) | $OCH_3$ |

Examples of the compounds of the formula (IIc) which are very particularly preferred as herbicide safeners according to the invention are listed in the table below.

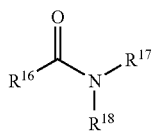

(IIc)

TABLE

Examples of the compounds of the formula (IIc)

| Example No. | $R^{16}$ | $N(R^{17}, R^{18})$ |
|---|---|---|
| IIc-1 | $CHCl_2$ | $N(CH_2CH=CH_2)_2$ |
| IIc-2 | $CHCl_2$ | 3-methyl-2,2-dimethyloxazolidine |
| IIc-3 | $CHCl_2$ | 3,4-dimethyl-2,2-dimethyloxazolidine |
| IIc-4 | $CHCl_2$ | 1-methyl-1-aza-4-oxa-spiro[4.5]decane (cyclohexane-spiro-oxazolidine) |
| IIc-5 | $CHCl_2$ | 3-methyl-2,2-dimethyl-5-phenyloxazolidine |
| IIc-6 | $CHCl_2$ | 3-methyl-4-methyl-benzoxazine |
| IIc-7 | $CHCl_2$ | 3-methyl-2,2-dimethyl-5-(2-furyl)oxazolidine |

Examples of the compounds of the formula (IId) which are very particularly preferred as herbicide safeners according to the invention are listed in the table below.

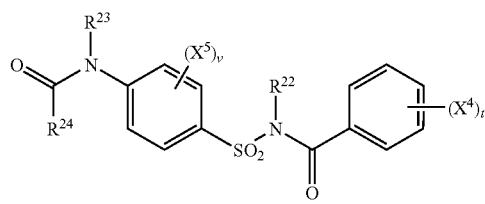

(IId)

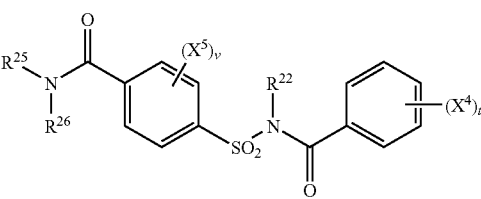

(IIe)

TABLE

Examples of the compounds of the formula (IId)

| Example No. | R²² | R²³ | R²⁴ | (positions) (X⁴)_t | (positions) (X⁵)_v |
|---|---|---|---|---|---|
| IId-1 | H | H | CH₃ | (2) OCH₃ | — |
| IId-2 | H | H | C₂H₅ | (2) OCH₃ | — |
| IId-3 | H | H | C₃H₇-n | (2) OCH₃ | — |
| IId-4 | H | H | C₃H₇-i | (2) OCH₃ | — |
| IId-5 | H | H | cyclopropyl | (2) OCH₃ | — |
| IId-6 | H | H | CH₃ | (2) OCH₃ (5) CH₃ | — |
| IId-7 | H | H | C₂H₅ | (2) OCH₃ (5) CH₃ | — |
| IId-8 | H | H | C₃H₇-n | (2) OCH₃ (5) CH₃ | — |
| IId-9 | H | H | C₃H₇-i | (2) OCH₃ (5) CH₃ | — |
| IId-10 | H | H | cyclopropyl | (2) OCH₃ (5) CH₃ | — |
| IId-11 | H | H | OCH₃ | (2) OCH₃ (5) CH₃ | — |
| IId-12 | H | H | OC₂H₅ | (2) OCH₃ (5) CH₃ | — |
| IId-13 | H | H | OC₃H₇-i | (2) OCH₃ (5) CH₃ | — |
| IId-14 | H | H | SCH₃ | (2) OCH₃ (5) CH₃ | — |
| IId-15 | H | H | SC₂H₅ | (2) OCH₃ (5) CH₃ | — |
| IId-16 | H | H | SC₃H₇-i | (2) OCH₃ (5) CH₃ | — |
| IId-17 | H | H | NHCH₃ | (2) OCH₃ (5) CH₃ | — |
| IId-18 | H | H | NHC₂H₅ | (2) OCH₃ (5) CH₃ | — |
| IId-19 | H | H | NHC₃H₇-i | (2) OCH₃ (5) CH₃ | — |
| IId-20 | H | H | NH-cyclopropyl | (2) OCH₃ (5) CH₃ | — |
| IId-21 | H | H | NHCH₃ | (2) OCH₃ | — |
| IId-22 | H | H | NHC₃H₇-i | (2) OCH₃ | — |
| IId-23 | H | H | N(CH₃)₂ | (2) OCH₃ | — |
| IId-24 | H | H | N(CH₃)₂ | (3) CH₃ (4) CH₃ | — |
| IId-25 | H | H | CH₂—O—CH₃ | (2) OCH₃ | — |

Examples of the compounds of the formula (IIe) which are very particularly preferred as herbicide safeners according to the invention are listed in the table below.

TABLE

Examples of the compounds of the formula (IIe)

| Example No. | R²² | R²⁵ | R²⁶ | (positions) (X⁴)_t | (positions) (X⁵)_v |
|---|---|---|---|---|---|
| IIe-1 | H | H | CH₃ | (2) OCH₃ | — |
| IIe-2 | H | H | C₂H₅ | (2) OCH₃ | — |
| IIe-3 | H | H | C₃H₇-n | (2) OCH₃ | — |
| IIe-4 | H | H | C₃H₇-i | (2) OCH₃ | — |
| IIe-5 | H | H | cyclopropyl | (2) OCH₃ | — |
| IIe-6 | H | CH₃ | CH₃ | (2) OCH₃ | — |
| IIe-7 | H | H | CH₃ | (2) OCH₃ (5) CH₃ | — |
| IIe-8 | H | H | C₂H₅ | (2) OCH₃ (5) CH₃ | — |
| IIe-9 | H | H | C₃H₇-n | (2) OCH₃ (5) CH₃ | — |
| IIe-10 | H | H | C₃H₇-i | (2) OCH₃ (5) CH₃ | — |
| IIe-11 | H | H | cyclopropyl | (2) OCH₃ (5) CH₃ | — |
| IIe-12 | H | CH₃ | CH₃ | (2) OCH₃ (5) CH₃ | — |

Most preferred as the crop plant tolerance promoter compound [component (b')] are cloquintocetmexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selectively herbicidal combinations according to the invention comprising in each case one active compound of the formula (I) and one of the safeners defined above are listed in the table below.

TABLE

Examples of the combinations according to the invention

| Active compounds of the formula (I) | Safener |
|---|---|
| I-a | cloquintocet-mexyl |
| I-a | fenchlorazole-ethyl |
| I-a | isoxadifen-ethyl |
| I-a | mefenpyr-diethyl |
| I-a | furilazole |
| I-a | fenclorim |
| I-a | cumyluron |
| I-a | daimuron/dymron |
| I-a | dimepiperate |
| I-a | IIe-11 |
| I-a | IIe-5 |
| I-b | cloquintocet-mexyl |
| I-b | fenchlorazole-ethyl |
| I-b | isoxadifen-ethyl |
| I-b | mefenpyr-diethyl |
| I-b | furilazole |
| I-b | fenclorim |
| I-b | cumyluron |
| I-b | daimuron/dymron |
| I-b | dimepiperate |
| I-b | IIe-11 |
| I-b | IIe-5 |
| I-c | cloquintocet-mexyl |
| I-c | fenchlorazole-ethyl |
| I-c | isoxadifen-ethyl |
| I-c | mefenpyr-diethyl |
| I-c | furilazole |
| I-c | fenclorim |
| I-c | cumyluron |
| I-c | daimuron/dymron |
| I-c | dimepiperate |
| I-c | IIe-5 |
| I-c | IIe-11 |
| I-d | cloquintocet-mexyl |
| I-d | fenchlorazole-ethyl |
| I-d | isoxadifen-ethyl |
| I-d | mefenpyr-diethyl |
| I-d | furilazole |
| I-d | fenclorim |
| I-d | cumyluron |
| I-d | daimuron/dymron |
| I-d | dimepiperate |
| I-d | IIe-11 |
| I-d | IIe-5 |
| I-e | cloquintocet-mexyl |
| I-e | fenchlorazole-ethyl |
| I-e | isoxadifen-ethyl |
| I-e | mefenpyr-diethyl |
| I-e | furilazole |
| I-e | fenclorim |
| I-e | cumyluron |
| I-e | daimuron/dymron |
| I-e | dimepiperate |
| I-e | IIe-5 |
| I-e | IIe-11 |
| I-f | cloquintocet-mexyl |
| I-f | fenchlorazole-ethyl |
| I-f | isoxadifen-ethyl |
| I-f | mefenpyr-diethyl |
| I-f | furilazole |
| I-f | fenclorim |
| I-f | cumyluron |
| I-f | daimuron/dymron |
| I-f | dimepiperate |
| I-f | IIe-5 |
| I-f | IIe-11 |
| I-g | cloquintocet-mexyl |
| I-g | fenchlorazole-ethyl |
| I-g | isoxadifen-ethyl |
| I-g | mefenpyr-diethyl |
| I-g | furilazole |
| I-g | fenclorim |
| I-g | cumyluron |
| I-g | daimuron/dymron |
| I-g | dimepiperate |
| I-g | IIe-5 |
| I-g | IIe-11 |

Surprisingly, it has now been found that the active compound combinations defined above of compounds of the general formula (I) and safeners (antidotes) from the group (b') set out above combine very good utility plant tolerance with a particularly high herbicidal activity and can be used in various crops, in particular in cereals (especially wheat), but also in soya, potatoes, maize and rice, for the selective control of weeds.

In this context it is to be considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of substituted cyclic ketoenols on the crop plants, without at the same time having any critical adverse effect on the herbicidal activity against the weeds.

Emphasis may be given here to the particularly advantageous effect of the particularly preferred and most preferred combination partners from group (b'), in particular with regard to the gentle treatment of cereal plants, such as wheat, barley and rye, for example, but also maize and rice, as crop plants.

In the literature it has already been described how the action of various active compounds can be boosted by addition of ammonium salts. The salts in question, however, are detersive salts (e.g. WO 95/017817) or salts which have relatively long alkyl substituents and/or aryl substituents and which have a permeabilizing action or which increase the active compound's solubility (e.g. EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842,476). A boost to action by ammonium sulphate, for example, is described by way of example for the herbicides glyphosate and phosphinothricin (U.S. Pat. No. 6,645,914, EP-A2 0 036 106). A corresponding action in the case of insecticides is neither disclosed nor suggested by this prior art.

The use of ammonium sulphate as a formulating assistant has also been described for certain active compounds and applications (WO 92/16108), but its purpose therein is to stabilize the formulation, not to boost the action.

It has now been found, entirely surprisingly, that the action of insecticides and/or acaricides and/or herbicides from the class of the alkoxyalkyl-substituted cyclic ketoenols can be boosted significantly through the addition of ammonium salts or phosphonium salts to the application solution or through the incorporation of these salts into a formulation comprising alkoxyalkyl-substituted cyclic ketoenols. The present invention therefore provides for the use of ammonium salts or phosphonium salts for boosting the action of crop protection compositions which comprise as their active compound herbicidal and/or insecticidal and/or acaricidal alkoxyalkyl-substituted cyclic ketoenols. The invention likewise provides compositions which comprise herbicidal and/or acaricidal and/or insecticidal alkoxyalkyl-substituted cyclic ketoenols and action-boosting ammonium salts or phosphonium salts, including not only formulated active compounds but also ready-to-use compositions (spray liquors). The invention further provides, finally, for the use of these compositions for controlling insect pests and/or spider mites and/or unwanted plant growth.

The compounds of the formula (I) possess a broad insecticidal and/or acaricidal and/or herbicidal activity, but individually the activity and/or plant tolerance leaves something to be desired.

The active compounds can be used in the compositions of the invention in a broad concentration range. The concentration of the active compounds in the formulation is typically 0.1%-50% by weight.

Ammonium salts and phosphonium salts which inventively boost the activity of crop protection compositions comprising fatty acid biosynthesis inhibitors are defined by formula (III')

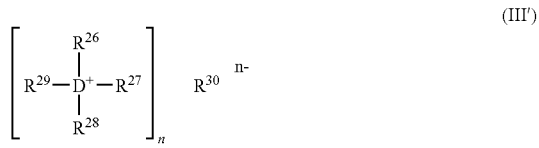

in which
D represents nitrogen or phosphorus,
D preferably represents nitrogen,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano,
$R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl,
$R^{26}$, $R^{27}$, $R^{28}$ and $R^{29}$ very particularly preferably represent hydrogen,
n represents 1, 2, 3 or 4,
n preferably represents 1 or 2,
$R^{30}$ represents an organic or inorganic anion,
$R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate,
$R^{30}$ particularly preferably represents lactate, sulphate, nitrate, thiosulphate, thiocyanate, oxalate or formate.
$R^{30}$ very particularly preferably represents sulphate.

Inventively emphasized combinations of active compound, salt and penetrant are listed in the table below. "Penetrant as per test" means here that any compound that acts as a penetrant in the cuticle penetration test (Baur et al., 1997, *Pesticide Science* 51, 131-152) is suitable.

The ammonium salts and phosphonium salts of the formula (III') can be used in a broad concentration range to boost the activity of crop protection compositions comprising ketoenols. In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active-ingredient concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal, alkoxyalkyl-substituted cyclic ketoenols as active compound. The invention likewise provides compositions which comprise herbicidal and/or acaricidal and/or insecticidal alkoxyalkyl-substituted cyclic ketoenols, penetrants and ammonium salts and/or phosphonium salts, including specifically not only formulated active compounds but also ready-to-use compositions (spray liquors). The invention additionally provides, finally, for the use of these compositions for controlling insect pests.

Suitable penetrants in the present context include all those substances which are typically used to enhance the penetration of active agrochemical compounds into plants. Penetrants are defined in this context by their ability to penetrate from the aqueous spray liquor and/or from the spray coating into the cuticle of the plant and thereby to increase the mobility of active compounds in the cuticle. The method described in the literature (Baur et al., 1997, *Pesticide Science* 51, 131-152) can be used in order to determine this property.

Examples of suitable penetrants include alkanol alkoxylates. Penetrants of the invention are alkanol alkoxylates of the formula (IV')

R—O-(-AO)$_v$—R'  (IV')

in which
R is linear or branched alkyl having 4 to 20 carbon atoms,
R' is hydrogen, methyl, ethyl, n-propyl, isopropyl, n-butyl, isobutyl, tert-butyl, n-pentyl or n-hexyl,
AO is an ethylene oxide radical, a propylene oxide radical, a butylene oxide radical or is mixtures of ethylene oxide and propylene oxide radicals or butylene oxide radicals, and
v is a number from 2 to 30.

One preferred group of penetrants are alkanol alkoxylates of the formula

R—O-(-EO—)$_n$—R'  (IV'-a)

in which
R is as defined above,
R' is as defined above,
EO is —CH$_2$—CH$_2$—O—, and
n is a number from 2 to 20.

A further preferred group of penetrants are alkanol alkoxylates of the formula

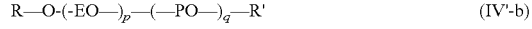
R—O-(-EO—)$_p$—(—PO—)$_q$—R'  (IV'-b)

in which
R is as defined above,
R' is as defined above,
EO is —CH$_2$—CH$_2$—O—,
PO is

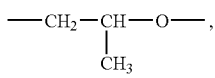

p is a number from 1 to 10, and
q is a number from 1 to 10.

A further preferred group of penetrants are alkanol alkoxylates of the formula

R—O—(—PO—)$_r$-(EO—)$_s$—R'    (IV'-c)

in which
R is as defined above,
R' is as defined above,
EO is —CH$_2$—CH$_2$—O—,
PO is

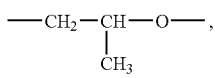

r is a number from 1 to 10, and
s is a number from 1 to 10.

A further preferred group of penetrants are alkanol alkoxylates of the formula

R—O-(-EO—)$_p$—(—BO—)$_q$—R'    (IV'-d)

in which
R and R' are as defined above,
EO is CH$_2$—CH$_2$—O—,
BO is

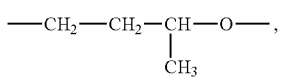

p is a number from 1 to 10 and
q is a number from 1 to 10.

A further preferred group of penetrants are alkanol alkoxylates of the formula

R—O—(—BO-)$_r$-(-EO—)$_s$—R'    (IV'-e)

in which
R and R' are as defined above,
BO is

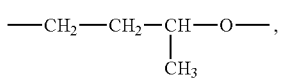

EO is CH$_2$—CH$_2$—O—,
r is a number from 1 to 10 and
s is a number from 1 to 10.

A further preferred group of penetrants are alkanol alkoxylates of the formula

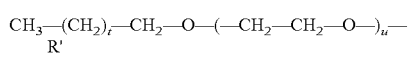

in which
R' is as defined above,
t is a number from 8 to 13,
u is a number from 6 to 17.

In the formulae indicated above,
R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

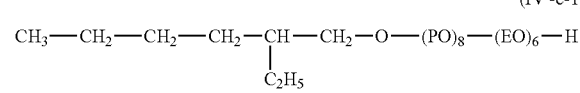

in which
EO is —CH$_2$—CH$_2$—O—,
PO is

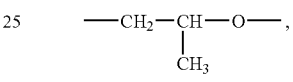

and
the numbers 8 and 6 represent average values.

As an example of an alkanol alkoxylate of the formula (IV'-d) mention may be made of the formula CH$_3$—(CH$_2$)$_{10}$—O-(-EO—)$_6$—(—BO—)$_2$—CH$_3$    (IV'-d-1)

in which
EO is CH$_2$—CH$_2$—O—,
BO is

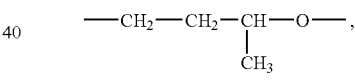

and
the numbers 10, 6 and 2 represent average values.

Particularly preferred alkanol alkoxylates of the formula (IV'-f) are compounds of this formula in which
t is a number from 9 to 12 and
u is a number from 7 to 9.

Mention may be made with very particular preference of alkanol alkoxylate of the formula (IV'-f-1)

CH$_3$—(CH$_2$)$_t$—CH$_2$—O—(—CH$_2$—CH$_2$—O—)$_u$—H    (IV'-f-1)

in which
t stands for the average value 10.5 and
u stands for the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soybean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth) acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, for example, according to process (A), ethyl N-[(4-(4-chlorophenyl)-2,6-dimethyl)-phenylacetyl]-2-amino-3-methoxy-2-methylpropionate as starting material, the course of the process of the invention can be represented by the following reaction scheme:

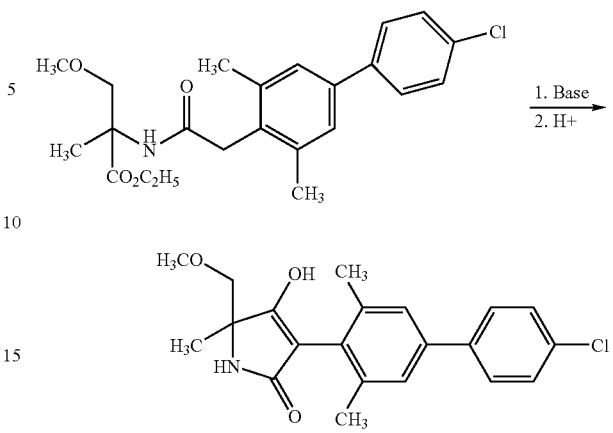

Using, for example, according to process (Bα), 3-[4-(4-chlorophenyl)-2,6-dimethylphenyl]-5-methoxymethyl-5-methylpyrrolidine-2,4-dione and pivaloyl chloride as starting materials, the course of the process of the invention can be represented by the following reaction scheme:

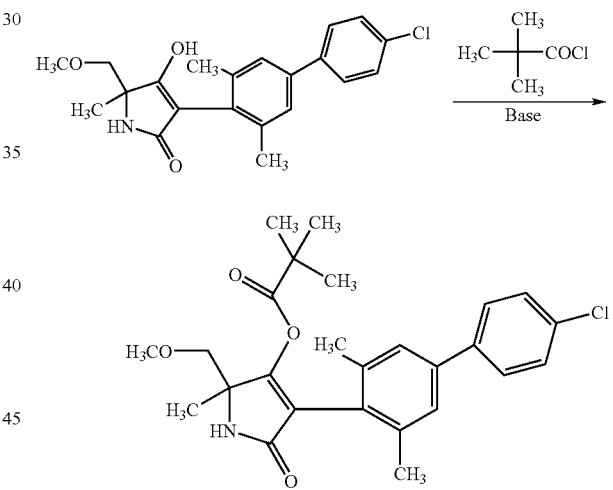

Using, for example, according to process (B) (variant β), 3-[5-(4-chlorophenyl)-2-chlorophenyl]-5-methoxymethyl-5-methylpyrrolidine-2,4-dione and acetic anhydride as starting compounds, the course of the process of the invention can be represented by the following reaction scheme:

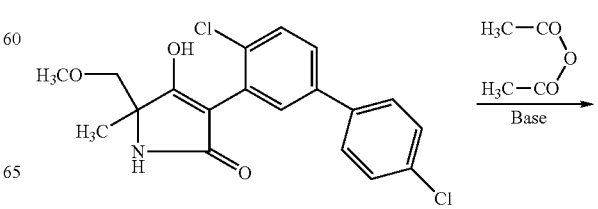

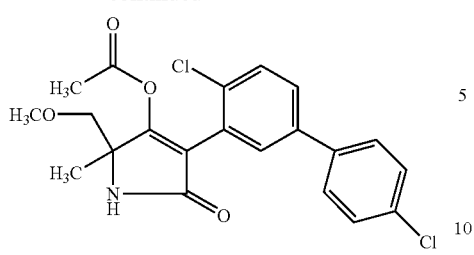

Using, for example, according to process (C), 3-[4-(4-chlorophenyl)-[(2-chloro-6-methylphenyl]]-5-methoxyethyl-5-methylpyrrolidine-2,4-dione and ethyl chloroformate as starting compounds, the course of the process of the invention can be represented by the following reaction scheme:

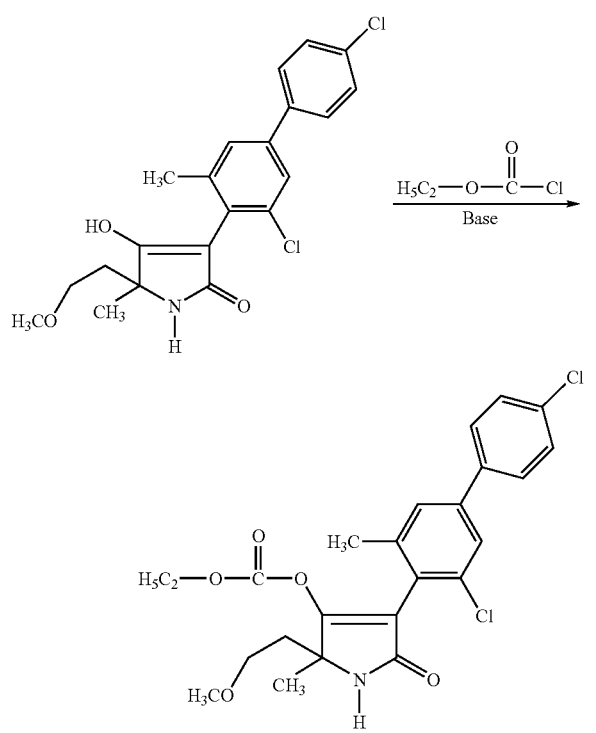

Using, for example, according to process (D), 3-[4-(4-chlorophenyl)-2,6-dimethylphenyl]-1-oxa-spiro[4.5]decane-2,4-dione and methyl chloromonothioformate as starting products, the course of the reaction can be represented as follows:

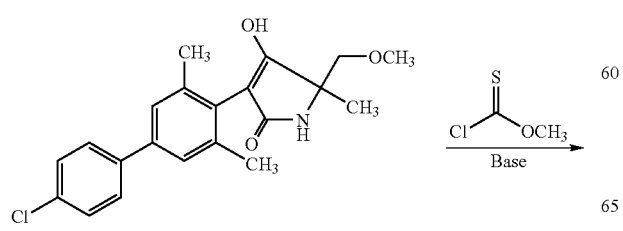

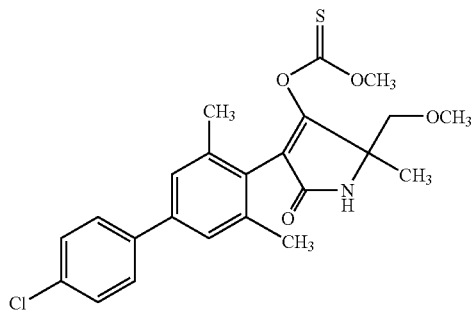

Using, for example, according to process (E), 3-[3-(4-chlorophenyl)-2,6-dimethylphenyl]-5-methoxymethyl-5-methylpyrrolidine-2,4-dione and methanesulphonyl chloride as starting product, the course of the reaction can be represented by the following reaction scheme:

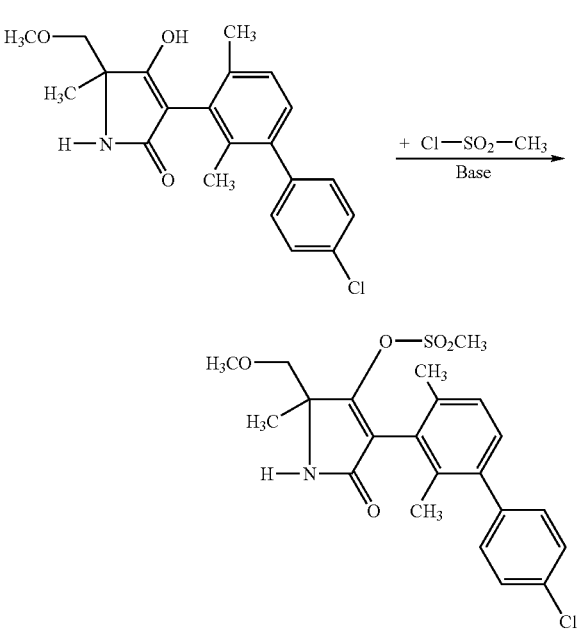

Using, for example, according to process (F), 3-[3-(4-chlorophenyl)-2,6-dimethylphenyl]-5-methoxymethyl-5-methylpyrrolidine-2,4-dione and methanethiophosphonyl chloride 2,2,2-trifluoroethyl ester as starting products, the course of the reaction can be represented by the following reaction scheme:

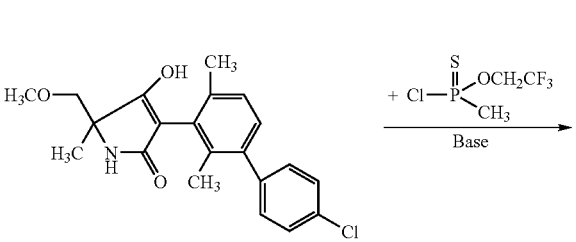

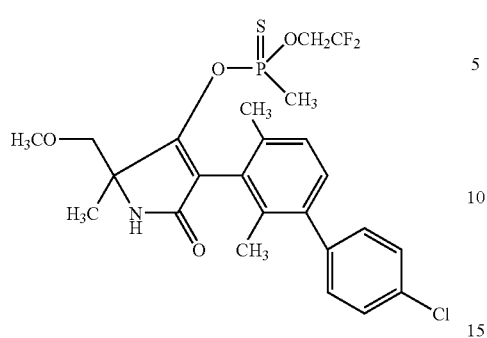

Using, for example, according to process (G), 3-[3-(4-chlorophenyl)-2,6-dimethylphenyl]-5-methoxyethyl-5-methylpyrrolidine-2,4-dione and NaOH as components, the course of the process of the invention can be represented by the following reaction scheme:

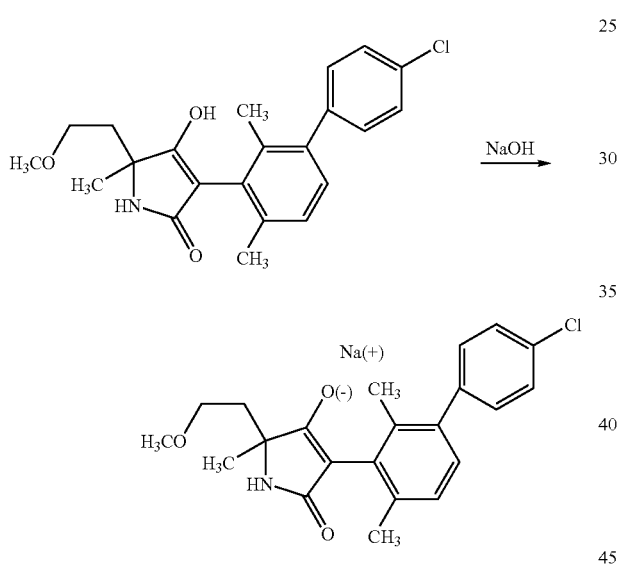

Using, for example, according to process (H) (variant α), 3-[5-(4-chlorophenyl)-2-methylphenyl]-5-methoxymethyl-5-methylpyrrolidine-2,4-dione and ethyl isocyanate as starting products, the course of the reaction can be represented by the following reaction scheme:

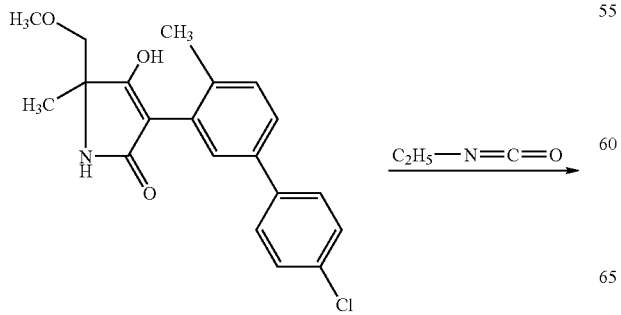

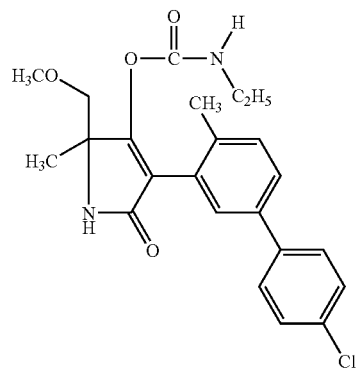

Using, for example, according to process (H) (variant β), 3-[3-(4-chlorophenyl)-2,6-dimethylphenyl]-5-methoxymethyl-5-methylpyrrolidine-2,4-dione and dimethylcarbamoyl chloride as starting products, the course of the reaction can be represented by the following scheme:

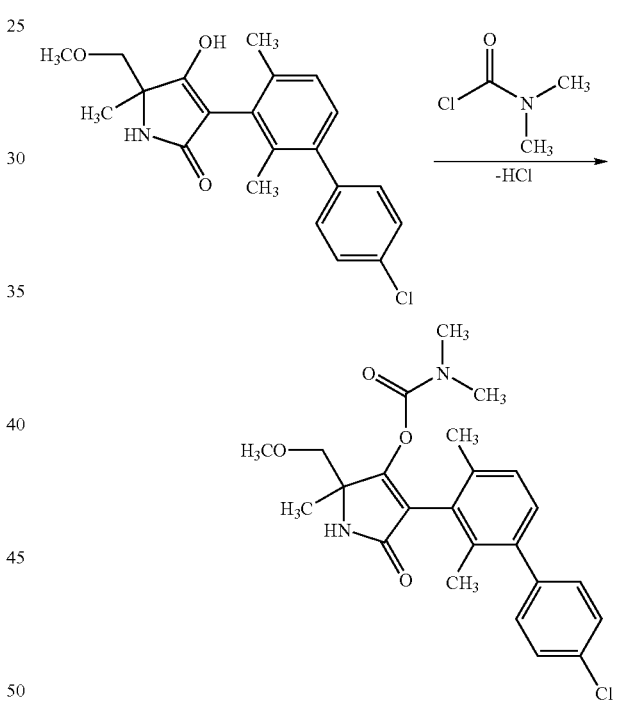

Using, for example, according to process (Iβ), 3-(4-bromo-2,6-dimethylphenyl)-5-methoxymethyl-5-methylpyrrolidine-2,4-dione and 4-chlorophenylboronic acid as starting materials, the course of the reaction can be represented by the following scheme:

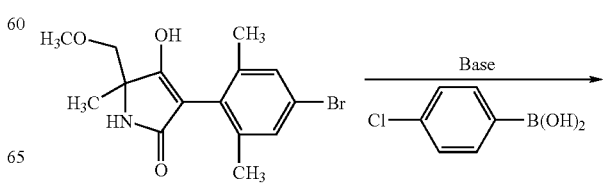

-continued

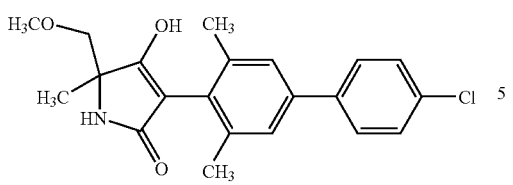

The compounds of the formula (II)

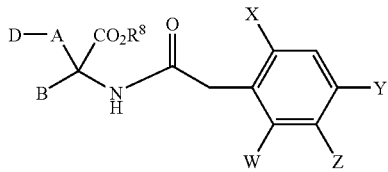
(II)

in which
A, B, D, W, X, Y, Z and $R^8$ have the definitions indicated above,
needed as starting materials for process (A) of the invention, are new.

The acylamino acid esters of the formula (II) are obtained, for example, if amino acid derivatives of the formula (XIII)

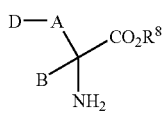
(XIII)

in which
A, B, D and $R^8$ have the definition indicated above,
are acylated with substituted phenylacetic acid derivatives of the formula (XIV)

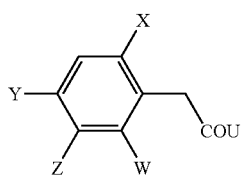
(XIV)

in which
W, X, Y and Z have the definitions indicated above and
U is a leaving group introduced by carboxylic acid activating reagents such as carbonyldiimidazole, carbonyldiimides (such as, for example, dicyclohexylcarbodiimide), phosphorylating reagents (such as, for example, $POCl_3$, BOP-Cl), halogenating agents such as, for example, thionyl chloride, oxalyl chloride, phosgene or chloroformic esters, (Chem. Reviews 52, 237416 (1953); Bhattacharya, Indian J. Chem. 6, 341-5, 1968)

or if acylamino acids of the formula (XV)

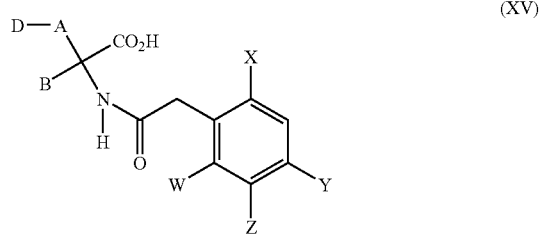
(XV)

in which
A, B, D, W, X, Y and Z have the definitions indicated above are esterified (Chem. Ind. (London) 1568 (1968)).
The compounds of the formula (XV)

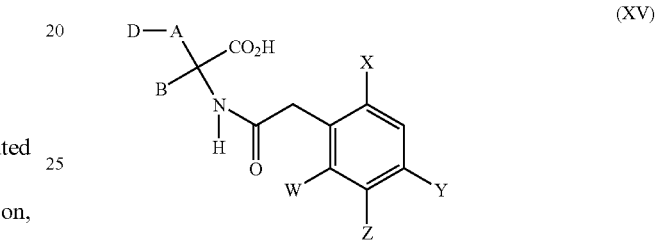
(XV)

in which
A, B, D, W, X, Y and Z have the definitions indicated above are new.

The compounds of the formula (XV) are obtained, for example, if 1-aminocarboxylic acids of the formula (XVI)

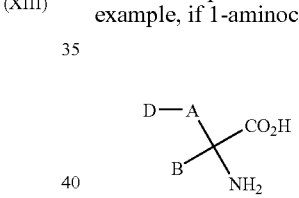
(XVI)

in which
A, B and D have the definitions indicated above
are acylated with substituted phenylacetic acid derivatives of the formula (XIV)

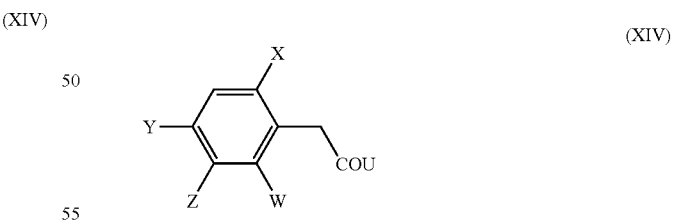
(XIV)

in which
U, W, X, Y and Z have the definitions indicated above
in accordance for example with Schotten-Baumann (Organikum, VEB Deutscher Verlag der Wissenschaften, Berlin 1977, p. 505).

The compounds of the formula (XIV) are in some cases known and/or can be prepared by the known processes in the laid-open specifications cited at the outset.

The compounds of the formula (XIII) and (XVI) are in some cases new and can be prepared by known processes (see, for example, Compagnon, Ann. Chim. (Paris) [14] 5, pp.

11-22, 23-27 (1970), L. Munday, J. Chem. Soc. 4372 (1961); J. T. Eward, C. Jitrangeri, Can. J. Chem. 53, 3339 (1975)).

Furthermore, the starting materials of the formula (II)

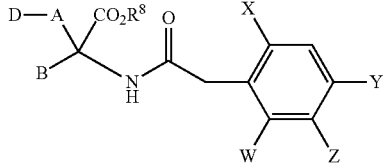
(II)

in which

A, B, D, W, X, Y, Z and $R^8$ have the definitions indicated above, used in process (A) above, can be prepared if 1-aminocarbonitriles of the formula (XVII)

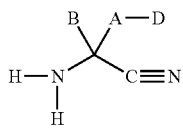
(XVII)

in which

A, B and D have the definitions indicated above, are reacted with substituted phenylacetic acid derivatives of the formula (XIV)

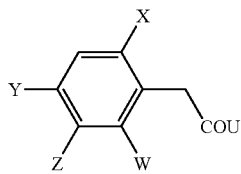
(XIV)

in which

U, W, X, Y and Z have the definitions indicated above to give compounds of the formula (XVIII)

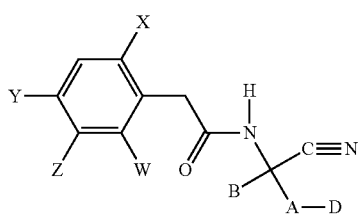
(XVIII)

in which

A, B, D, W, X, Y and Z have the definitions indicated above, and these compounds are then subjected to acidic alcoholysis.

The compounds of the formula (XVI) are obtained, for example, by reacting hydantoins of the formula (XX)

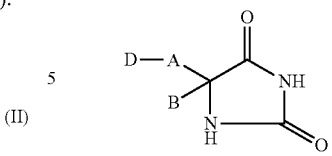
(XX)

in which A, B and D have the definitions indicated above.

The compounds of the formula (XX) are in some cases new and can be prepared by known processes.

The compounds of the formula (XVIII) are likewise new. The compounds of the formula (XVII) are in some cases new and can be prepared for example as described in EP-A-595 130.

The compounds I-a' to I-g' and I-a" to I-g" are in some cases described in DE-A-06018828 or can be prepared by the processes described therein.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formula (IX) and (X) and isocyanates of the formula (XI) and carbamoyl chlorides of the formula (XII) and boronic acids of the formula (XIX), which are needed additionally as starting materials for carrying out processes (B), (C), (D), (E), (F), (G), (H) and (I) of the invention, are compounds which are general knowledge within organic or inorganic chemistry.

Process (A) is characterized in that compounds of the formula (II), in which A, B, D, W, X, Y, Z and $R^8$ have the definitions indicated above, are subjected to intramolecular condensation in the presence of a diluent and in the presence of a base.

Diluents which can be used in process (A) of the invention include all organic solvents that are inert towards the reactants. With preference it is possible to use hydrocarbons, such as toluene and xylene, and ethers, such as dibutyl ether, tetrahydrofuran, dioxane, glycol dimethyl ether and diglycol dimethyl ether, additionally, polar solvents, such as dimethyl sulphoxide, sulpholane, dimethylformamide and N-methylpyrrolidone, and also alcohols such as methanol, ethanol, propanol, isopropanol, butanol, isobutanol and tert-butanol.

Bases (deprotonating agents) which can be used when carrying out process (A) of the invention include all typical proton acceptors. With preference it is possible to use alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts such as triethylbenzylammonium chloride, tetrabutylammonium bromide, Adogen 464 (i.e. methyltrialkyl($C_8$-$C_{10}$)ammonium chloride) or TDA 1 (i.e. tris(methoxyethoxyethyl)amine). In addition it is possible to use alkali metals such as sodium or potassium. Others which may be employed are alkali metal and alkaline earth metal amides and hydrides, such as sodium amide, sodium hydride and calcium hydride, and also alkali metal alkoxides, such as sodium methoxide, sodium ethoxide and potassium tert-butoxide.

The reaction temperature when carrying out process (A) of the invention may be varied within a relatively wide range. Generally it is operated at temperatures between −75° C. and 200° C., preferably between −50° C. and 150° C.

Process (A) of the invention is generally carried out under atmospheric pressure.

When process (A) of the invention is being carried out, the reaction component of the formula (II) and the deprotonating base are generally used in equimolar to approximately twice-equimolar amounts. It is also possible, however, to use one or the other component in a larger excess (up to 3 mol).

Process ($B_\alpha$) is characterized in that compounds of the formula (I-a) are reacted in each case with carbonyl halides of the formula (III), optionally in the presence of a diluent and optionally in the presence of an acid-binding agent.

Diluents which can be used in process ($B_\alpha$) of the invention include all solvents that are inert towards the acid halides. With preference it is possible to use hydrocarbons, such as benzine, benzene, toluene, xylene and tetralin, and halogenated hydrocarbons, such as methylene chloride, chloroform, carbon tetrachloride, chlorobenzene and o-dichlorobenzene, and ketones, such as acetone and methyl isopropyl ketone, and ethers, such as diethyl ether, tetrahydrofuran and dioxane, and carboxylic esters, such as ethyl acetate, and also strongly polar solvents, such as dimethylformamide, dimethyl sulphoxide and sulpholane. If the stability of the acid halide to hydrolysis permits it, the reaction can also be carried out in the presence of water.

Suitable acid-binding agents in the context of the reaction according to process ($B_\alpha$) of the invention include all typical acid acceptors. With preference it is possible to use tertiary amines, such as triethylamine, pyridine, diazabicyclooctane (DABCO), diazabicycloundecene (DBU), diazabicyclononene (DBN), Hünig base and N,N-dimethylaniline, and alkaline earth metal oxides, such as magnesium oxide and calcium oxide, and alkali metal and alkaline earth metal carbonates, such as sodium carbonate, potassium carbonate and calcium carbonate, and also alkali metal hydroxides such as sodium hydroxide and potassium hydroxide.

The reaction temperature for process ($B_\alpha$) of the invention may be varied within a relatively wide range. It is operated generally at temperatures between $-20°$ C. and $+150°$ C., preferably between $0°$ C. and $100°$ C.

When process ($B_\alpha$) of the invention is being carried out, the starting materials of the formula (I-a) and the carbonyl halide of the formula (III) are used generally in each case in approximately equivalent amounts. It is also possible, however, to use the carbonyl halide in a larger excess (up to 5 mol). Working up takes place in accordance with typical methods.

Process ($B_\beta$) is characterized in that compounds of the formula (I-a) are reacted in each case with carboxylic anhydrides of the formula (IV), optionally in the presence of a diluent and optionally in the presence of an acid-binding agent.

Diluents which can be used in process ($B_\beta$) of the invention are preferably those diluents also contemplated with preference when using acid halides. Moreover, it is also possible for a carboxylic anhydride employed in excess to function simultaneously as diluent.

Suitable acid-binding agents added optionally in process ($B_\beta$) are preferably those acid-binding agents which are also suitable with preference when using acid halides.

The reaction temperature in process ($B_\beta$) of the invention can be varied within a relatively wide range. In general it is operated at temperatures between $-20°$ C. and $+150°$ C., preferably between $0°$ C. and $100°$ C.

When process ($B_\beta$) of the invention is being carried out, the starting materials of the formulae (I-a) and the carboxylic anhydride of the formula (IV) are generally used in amounts which in each case are approximately equivalent. It is also possible, however, to use the carboxylic anhydride in a larger excess (up to 5 mol). Working up takes place in accordance with typical methods.

A general procedure is to remove diluents and carboxylic anhydride present in excess, and also the resultant carboxylic acid, by distillation or by washing with an organic solvent or with water.

Process (C) is characterized in that compounds of the formula (I-a) are reacted in each case with chloroformic esters or chloroformic thioesters of the formula (V), optionally in the presence of a diluent and optionally in the presence of an acid-binding agent.

Suitable acid-binding agents for process (C) of the invention include all typical acid acceptors. With preference it is possible to use tertiary amines, such as triethylamine, pyridine, DABCO, DBU, DBN, Hünig base and N,N-dimethylaniline, and alkaline earth metal oxides, such as magnesium oxide and calcium oxide, and alkali metal and alkaline earth metal carbonates, such as sodium carbonate, potassium carbonate and calcium carbonate, and also alkali metal hydroxides such as sodium hydroxide and potassium hydroxide.

Diluents which can be used in process (C) of the invention include all solvents that are inert towards the chloroformic esters and/or chloroformic thioesters. With preference it is possible to use hydrocarbons, such as benzine, benzene, toluene, xylene and tetralin, and halogenated hydrocarbons, such as methylene chloride, chloroform, carbon tetrachloride, chlorobenzene and o-dichlorobenzene, and ketones, such as acetone and methyl isopropyl ketone, and ethers, such as diethyl ether, tetrahydrofuran and dioxane, and carboxylic esters, such as ethyl acetate, and nitriles such as acetonitrile, and also strongly polar solvents, such as dimethylformamide, dimethyl sulphoxide and sulpholane.

The reaction temperature when carrying out process (C) of the invention can be varied within a relatively wide range. The reaction temperature is generally between $-20°$ C. and $+100°$ C., preferably between $0°$ C. and $50°$ C.

Process (C) of the invention is generally carried out under atmospheric pressure.

When process (C) of the invention is being carried out, the starting materials of the formula (I-a) and the corresponding chloroformic ester and/or chloroformic thioester of the formula (V) are used generally in each case in approximately equivalent amounts. It is also possible, however, to use one or the other component in a larger excess (up to 2 mol). Working up takes place in accordance with typical methods. The general procedure is to remove salts that have precipitated and to concentrate the remaining reaction mixture by stripping off the diluent.

Process (D) of the invention is characterized in that compounds of the formula (I-a) are reacted in each case with compounds of the formula (VI) in the presence of a diluent and optionally in the presence of an acid-binding agent.

In preparation process (D) about 1 mol of chloromonothioformic ester and/or chlorodithioformic ester of the formula (VI) per mole of starting compound of the formula (I-a) is reacted at 0 to $120°$ C., preferably at 20 to $60°$ C.

Suitable diluents added optionally include all inert polar organic solvents, such as ethers, amides, sulphones, sulphoxides, but also haloalkanes.

Preference is given to using dimethyl sulphoxide, tetrahydrofuran, dimethylformamide, ethyl acetate or methylene chloride.

If, in one preferred embodiment, the enolate salt of the compounds (I-a) is prepared, by the addition of strong deprotonating agents such as sodium hydride or potassium tert-butoxide for example, it is possible to forego the further addition of acid-binding agents.

Bases which can be used in process (D) are all typical proton acceptors. With preference it is possible to use alkali metal hydrides, alkali metal alkoxides, alkali metal or alkaline earth metal carbonates or hydrogen carbonates or nitrogen bases. By way of example mention may be made of sodium hydride, sodium methoxide, sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

The reaction can be carried out at atmospheric pressure or at an elevated pressure, but preferably at atmospheric pressure. Working up takes place in accordance with typical methods.

Process (E) of the invention is characterized in that compounds of the formula (I-a) are reacted in each case with sulphonyl chlorides of the formula (VII), optionally in the presence of a diluent and optionally in the presence of an acid-binding agent.

In preparation process (E) about 1 mol of sulphonyl chloride of the formula (VII) per mole of starting compound of the formula (I-a) is reacted at −20 to 150° C., preferably at 0 to 70° C.

Process (E) is carried out preferably in the presence of a diluent.

Suitable diluents include all inert polar organic solvents, such as ethers, amides, ketones, carboxylic esters, nitrites, sulphones, sulphoxides or halogenated hydrocarbons such as methylene chloride.

Preference is given to using dimethyl sulphoxide, tetrahydrofuran, dimethylformamide, ethyl acetate or methylene chloride.

If, in one preferred embodiment, the enolate salt of the compound (I-a) is prepared, as a result of the addition of strong deprotonating agents (such as sodium hydride or potassium tert-butoxide, for example), then it is possible to forego the further addition of acid-binding agents.

Where acid-binding agents are used, those suitable include typical organic or inorganic bases; by way of example, mention may be made of sodium hydroxide, sodium carbonate, potassium carbonate, pyridine and triethylamine.

The reaction can be carried out at atmospheric pressure or at an elevated pressure, but preferably at atmospheric pressure. Working up takes place in accordance with typical methods.

Process (F) of the invention is characterized in that compounds of the formula (I-a) are reacted in each case with phosphorus compounds of the formula (VIII), optionally in the presence of a diluent and optionally in the presence of an acid-binding agent.

In preparation process (F) compounds of the formula (I-e) are obtained by reacting 1 to 2, preferably 1 to 1.3 mol of the phosphorus compound of the formula (VIII) per mole of the compounds (I-a) at temperatures between −40° C. and 150° C., preferably between −10 and 110° C.

Process (F) is carried out preferably in the presence of a diluent.

Suitable diluents include all inert, polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide or methylene chloride.

Acid-binding agents, added optionally, suitably include typical organic or inorganic bases, such as hydroxides, carbonates or amines. Those which may be recited by way of example include sodium hydroxide, sodium carbonate, potassium carbonate, pyridine and triethylamine.

The reaction can be carried out at atmospheric pressure or at an elevated pressure, but preferably at atmospheric pressure. Working up takes place in accordance with typical methods of organic chemistry. The end products are preferably purified by crystallization, by chromatographic purification or by partial distillation, i.e. removal of the volatile constituents in vacuo.

Process (G) is characterized in that compounds of the formula (I-a) are reacted in each case with metal hydroxides and/or metal alkoxides of the formula (IX) or amines of the formula (X), optionally in the presence of a diluent.

Diluents which can be used in process (G) of the invention are preferably ethers such as tetrahydrofuran, dioxane or diethyl ether or else alcohols such as methanol, ethanol or isopropanol, but also water. Process (G) of the invention is carried out generally under atmospheric pressure. The reaction temperature is generally between −20° C. and 100° C., preferably between 0° C. and 50° C.

Process (H) of the invention is characterized in that compounds of the formula (I-a) are reacted in each case with (Hα) compounds of the formula (XI), optionally in the presence of a diluent and optionally in the presence of a catalyst, or (Hβ) with compounds of the formula (XII), optionally in the presence of a diluent and optionally in the presence of an acid-binding agent.

In preparation process (Hα) about 1 mol of isocyanate of the formula (XI) per mole of starting compound of the formula (I-a) is reacted at 0 to 100° C., preferably at 20 to 50° C.

Process (Hα) is carried out preferably in the presence of a diluent.

Suitable diluents include all inert organic solvents, such as aromatic hydrocarbons, halogenated hydrocarbons, ethers, amides, nitrites, sulphones or sulphoxides.

Optionally it is possible to add catalysts in order to accelerate the reaction. Catalysts which can be used to good advantage include organotin compounds, such as dibutyltin dilaurate, for example.

Operation takes place preferably under atmospheric pressure.

In preparation process (Hβ) about 1 mol of carbamoyl chloride of the formula (XII) per mole of starting compound of the formula (I-a) is reacted at 0 to 150° C., preferably at 20 to 70° C.

Suitable diluents, added optionally, include all inert polar organic solvents, such as ethers, carboxylic esters, nitrites, ketones, amides, sulphones, sulphoxides or halogenated hydrocarbons.

Preference is given to using dimethyl sulphoxide, tetrahydrofuran, dimethylformamide or methylene chloride.

If, in one preferred embodiment, the enolate salt of the compound (I-a) is prepared, by the addition of strong deprotonating agents (such as sodium hydride or potassium tert-butoxide, for example), it is possible to forego the further addition of acid-binding agents.

If acid-binding agents are used, they suitably include typical organic or inorganic bases. By way of example, mention may be made of sodium hydroxide, sodium carbonate, potassium carbonate, triethylamine or pyridine.

The reaction can be carried out at atmospheric pressure or at an elevated pressure, preferably at atmospheric pressure. Working up takes place in accordance with typical methods.

For the implementation of process (Iα) and (Iβ) of the invention, palladium(0) complexes are suitable catalysts. Preference is given, for example, to tetrakis(triphenylphosphine)palladium. Optionally it is also possible to use palladium(II) compounds, examples being $PdCl_2$, $Pd(OAc)_2$. When palladium(II) compounds are used, phosphines, such as tricyclohexylphosphine, for example, are generally employed as complexing agents.

Suitable acid acceptors for the implementation of process (Iα) and (Iβ) of the invention are organic or inorganic bases. These include, preferably, alkaline earth metal or alkali metal hydroxides, acetates, carbonates or hydrogen carbonates, such as sodium, potassium, barium or ammonium hydroxide, sodium, potassium, calcium or ammonium acetate, sodium, potassium, caesium or ammonium carbonate, sodium hydrogen carbonate or potassium hydrogen carbonate, for example, alkali metal fluorides, such as caesium fluoride, alkali metal phosphates such as potassium dihydrogen phosphate, potassium phosphate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for implementing process (Iα) and (Iβ) of the invention include water, organic solvents and any desired mixtures thereof. By way of example mention may be made of the following: aliphatic, alicyclic or aromatic hydrocarbons, such as petroleum ether, hexane, heptane, cyclohexane, methylcyclohexane, benzene, toluene, xylene or decalin, for example; halogenated hydrocarbons, such as chlorobenzene, dichlorobenzene, methylene chloride, chloroform, tetrachloromethane, dichloroethane, trichloroethane or tetrachloroethylene, for example; ethers, such as diethyl ether, diisopropyl ether, methyl tert-butyl ether, methyl tert-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethyl glycol monomethyl ether; water.

The reaction temperature in process (Iα) and (Iβ) of the invention can be varied within a relatively wide range. Operation takes place in general at temperatures between 0° C. and +140° C., preferably between 50° C. and +100° C.

When process (Iα) and (Iβ) of the invention is being carried out, the boronic acids of the formulae (XIXα) and (XIXβ) in which Y and Z are as defined above, and compounds of the formulae (I-a') to (I-g') in which A, B, D, G, W, X, Y, and Z', and (I-a") to (I-g") in which A, B, D, G, W, X, Z and Y', are as defined above, are used in a molar ratio of 1:1 to 3:1, preferably 1:1 to 2:1. The amount of catalyst used is generally 0.005 to 0.5 mol, preferably 0.01 mol to 0.1 mol, per mole of the compounds of the formulae (I-a') to (I-g') or (I-a") to (I-g"). The base is generally employed in an excess.

The inventive active compounds/active compound combinations, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Aftagenus* spp., *Bruchidius obtectus, Bruchus* spp., *Ceuthorhynchus* spp., *Cleonus mendicus, Conoderus* spp., *Cosmopolites* spp., *Costelytra zea-landica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chryso-cephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa*.

From the class of the Gastropoda, for example, *Arion* spp., *Biomphalaria* spp., *Bulinus* spp., *Deroceras* spp., *Galba* spp., *Lyrnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocu-*

*laris, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control Protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kaehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Ermeothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus dipsaci, Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds/active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seeds, and also roots, tubers and rhizomes. The plant parts also include harvested material, and vegetative and generative propagation material, for example cuttings, tubers, rhizomes, offshoots and seeds.

Treatment according to the invention of the plants and plant parts with the active compounds/active compound combinations is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds/active compound combinations can be converted to the customary formulations, such as solutions, emulsions, wettable powders, water- and oil-based suspensions, powders, dusting agents, pastes, soluble powders, soluble granules, granules for broadcasting, suspoemulsion concentrates, natural materials impregnated with active compound, synthetic materials impregnated with active compound, fertilizers and microencapsulations in polymeric substances.

These formulations are produced in a known manner, for example by mixing the active compounds/active compound combinations with extenders, that is liquid solvents and/or solid carriers, optionally with the use of surface-active agents, that is emulsifiers and/or dispersants and/or foam formers.

If the extender used is water, it is also possible to use organic solvents, for example, as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, as well as their ethers and esters, ketones, such as acetone, methyl ethyl ketone, methyl isobutyl ketone or cyclohexanone, strongly polar solvents, such as dimethyl sulphoxide, and also water.

Suitable solid carriers are:
for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound/active compound combinations according to the invention can be present in their commercially available formulations, as well as in the use forms prepared from these formulations, in a mixture with other active compounds such as insecticides, attractants, sterilizers, bactericides, acaricides, nematicides, fungicides, growth-regulating substances, herbicides, safeners, fertilizers or semiochemicals.

Compounds which are particularly favourable as mixing partners are, for example, the following:
Fungicides:
2-phenylphenol; 8-hydroxyquinoline sulphate; acibenzolar-5-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]-butanamide; 1-(1-naphthalenyl)-1H-pyrrole-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3- trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro-[4.5]decane-3-amine; sodium tetrathiocarbonate; and copper salts and preparations, such as Bordeaux mixture; copper hydroxide; copper naphthenate; copper oxychloride; copper sulphate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
Acetylcholine Esterase (AChE) Inhibitors
1.1 Carbamates,
   for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
1.2 Organophosphates,
   for example acephate, azamethiphos, azinphos (-methyl, -ethyl), bromophos-ethyl, brom-fenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methyl sulphone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-Gated Sodium Channel Blockers
2.1 Pyrethroids,
   for example acrinathrin, allethrin (d-cis-trans, d-trans), beta-cyfluthrin, bifenthrin, bioallethrin, bioallethrin-S cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
   DDT
2.2 Oxadiazines,
   for example indoxacarb
2.3 Semicarbazones
   for example metaflumizone (BAS 3201)

Acetylcholine Receptor Agonists/Antagonists
3.1 Chloronicotinyls,
   for example acetamiprid, clothianidin, dinotefuran, imidacloprid, nitenpyram, nithiazine, thiacloprid, thiamethoxam
3.2 Nicotine, bensultap, cartap Acetylcholine Receptor Modulators
4.1 Spinosyns,
   for example spinosad GABA-Gated Chloride Channel Antagonists
5.1 Organochlorines,
   for example camphechlor, chlordane, endosulfan, gamma-HCH, HCH, heptachlor, lindane, methoxychlor
5.2 Fiproles,
   for example acetoprole, ethiprole, fipronil, pyrafluprole, pyripole, vaniliprole Chloride Channel Activators
6.1 Mectins,
   for example avermectin, emamectin, emamectin benzoate, ivermectin, milbemycin Juvenile Hormone Mimetics,
   for example diofenolan, epofenonane, fenoxycarb, hydroprene, kinoprene, methoprene, pyriproxifen, triprene Ecdyson Agonists/Disruptors
8.1 Diacylhydrazines,
   for example chromafenozide, halofenozide, methoxyfenozide, tebufenozide Chitin Biosynthesis Inhibitors
9.1 Benzoylureas,
   for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
9.2 Buprofezin
9.3 Cyromazine Oxidative Phosphorylation Inhibitors, ATP Disruptors
10.1 Diafenthiuron
10.2 Organotins,
   for example azocyclotin, cyhexatin, fenbutatin oxide Oxidative Phosphorylation Decouplers Acting by Interrupting the H-Proton Gradient
11.1 Pyrroles,
   for example chlorfenapyr
11.2 Dinitrophenols,
   for example binapacyrl, dinobuton, dinocap, DNOC Electron Transport Inhibitors
12.1 Site-I electron transport inhibitors
   from the group of
   METIs,
   for example fenazaquin, fenpyroximate, pyrimidifen, pyridaben, tebufenpyrad, tolfenpyrad and also
   hydramethylnon
   dicofol
12.2 Site-II electron transport inhibitors
   rotenone, cyflumetofen, cyenopyrafen 12.3 Site-III electron transport inhibitors
acequinocyl, fluacrypyrim
Microbial Disruptors of the Insect Gut Membrane
*Bacillus thuringiensis* strains
Fatty Acid Biosynthesis Inhibitors
14.1 Tetronic acids,
for example spirodiclofen, spiromesifen
14.2 Tetramic acids,
for example spirotetramat, cis-3-(2,5-dimethylphenyl)-4-hydroxy-8-methoxy-1-aza-spiro[4.5]dec-3-en-2-one
Carboxamides,
for example flonicamid
Octopaminergic Agonists,
for example amitraz
Inhibitors of Magnesium-Stimulated ATPase,
propargite
Ryanodin Receptor Effectors
18.1 benzodicarboxamides,
for example flubendiamide
18.2 anthranilamides, for example rynaxapyr, HGW86
Nereistoxin Analogues,
for example thiocyclam hydrogen oxalate, thiosultap-sodium
Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.
Active Compounds with Unknown or Unspecific Mechanisms of Action
21.1 Fumigants,
for example aluminium phosphide, methyl bromide, sulphuryl fluoride
21.2 Antifeedants,
for example cryolite, flonicamid, pymetrozine
21.3 Mite growth inhibitors,
for example clofentezine, etoxazole, hexythiazox
21.4 Amidoflumet, benclothiaz, benzoximate, bifenazate, bromopropylate, buprofezin, chino-methionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents which improve plant properties is also possible.

When used as insecticides in their commercially available formulations and in the use forms prepared from these formulations, the active compounds/active compound combinations according to the invention can furthermore be present in the form of a mixture with synergists. Synergists are compounds by which the activity of the active compounds is increased without it being necessary for the synergist added to be active itself.

When used as insecticides in their commercially available formulations and in the use forms prepared from these formulations, the active compounds/active compound combinations according to the invention can furthermore be present in the form of mixtures with inhibitors which reduce the degradation of the active compound after application in the surroundings of the plant, on the surface of parts of plants or in plant tissues.

The active compound content of the use forms prepared from the commercially available formulations can vary within wide ranges. The active compound concentration of the use forms can be from 0.00000001 up to 95% by weight of active compound and is preferably between 0.00001 and 1% by weight.

Application is in a customary manner adapted to suit the use forms.

As already mentioned above, it is possible to treat all plants and their parts in accordance with the invention. In a preferred embodiment, wild plant species and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The terms "parts" or "parts of plants" or "plant parts" have been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher harvest yields, higher quality and/or higher nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher harvest yields, higher quality and/or higher nutritional value of the harvested products, better storage characteristics and/or processability of the harvested products. Further examples of such traits, examples which must be particularly emphasized, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potatoes, sugar beet, tomatoes, peas and other vegetable varieties, cotton, tobacco, oilseed rape and fruit plants (with the fruits apples, pears, citrus fruits and grapes), with particular emphasis on maize, soybeans, potatoes, cotton, tobacco and oilseed rape. Traits which are especially emphasized are the increased defense of the plants against insects, arachnids, nematodes and slugs and snails, owing to toxins being formed in the plants, in particular toxins which are generated in the plants by the genetic material of *Bacillus thuringiensis* (for example by the genes CryIA(a), CryIA(b), CryIA(c), CryIIA, CryIIA, CryIIIB2, Cry9c Cry2Ab, Cry3Bb and CryIF and their combinations) (hereinbelow "Bt plants"). Other traits which are particularly emphasized are the increased defense of plants against fungi, bacteria and viruses by systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulphonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybeans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula I or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds/active compound combinations according to the invention are not only active against plant, hygiene and stored-product pests, but also, in the veterinary medicine sector, against animal parasites (ectoparasites and endoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the sub-class of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds/active compound combinations of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector and in the case of animal keeping, the active compounds/active compound combinations according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds/active compound combinations according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flash point of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flash point of above 30° C., preferably above 45° C., can be partially replaced by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di(2-ethylhexyl) adipate, the stearates, such as butyl stearate or amyl stearate, the oleates, such as butyl oleate, the glycerol ethers or relatively high molecular weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid, triflumuron, chlothianidin, spinosad, tefluthrin, and fungicides, such as epoxyconazole, hexaconazole, azaconazole, propiconazole, tebuconazole, cyproconazole, metconazole, imazalil, dichlorfluanid, tolylfluanid, 3-iodo-2-propynyl butylcarbamate, N-octyl-isothiazolin-3-one and 4,5-dichloro-N-octylisothiazolin-3-one.

The compounds according to the invention can at the same time be employed for protecting objects which come into contact with saltwater or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling in particular by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb, Fe chelates;
or conventional antifouling active compounds such as
4,5-dichloro-2-octyl-4-isothiazolin-3-one, diiodomethylparatryl sulphone, 2-(N,N-dimethyl-thiocarbamoylthio)-5-nitrothiazyl, potassium, copper, sodium and zinc salts of 2-pyridinethiol 1-oxide, pyridinetriphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in saltwater. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus*

*sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used in the household insecticides sector alone or in combination with other suitable active compounds such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds/active compound combinations according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds/active compound combinations according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds/active compound combinations according to the invention is in no way restricted to these genera, but also extends in the same manner to other plants.

Depending on the concentration, the active compounds/active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantations and hop fields, on lawns, turf and pastureland, and for the selective control of weeds in annual crops.

The compounds of the formula (I)/active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds/active compound combinations according to the invention can also be employed for controlling animal pests and fungal or bacterial plant diseases. If appropriate, they can also be used as intermediates or precursors for the synthesis of other active compounds.

The active compounds/active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian blue, and organic colorants, such as alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds/active compound combinations according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example
acetochlor, acifluorfen (-sodium), aclonifen, alachlor, alloxydim (-sodium), ametryne, amicarbazone, amidochlor, amidosulfuron, aminopyralid, anilofos, asulam, atrazine, azafenidin, azimsulfuron, beflubutamid, benazolin (-ethyl), benfuresate, bensulfuron (-methyl), bentazone, bencarbazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfuron, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrimisulfan, pyrithiobac (-sodium), pyroxsulam, pyroxasulfone, quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thiencarbazone-methyl thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron and

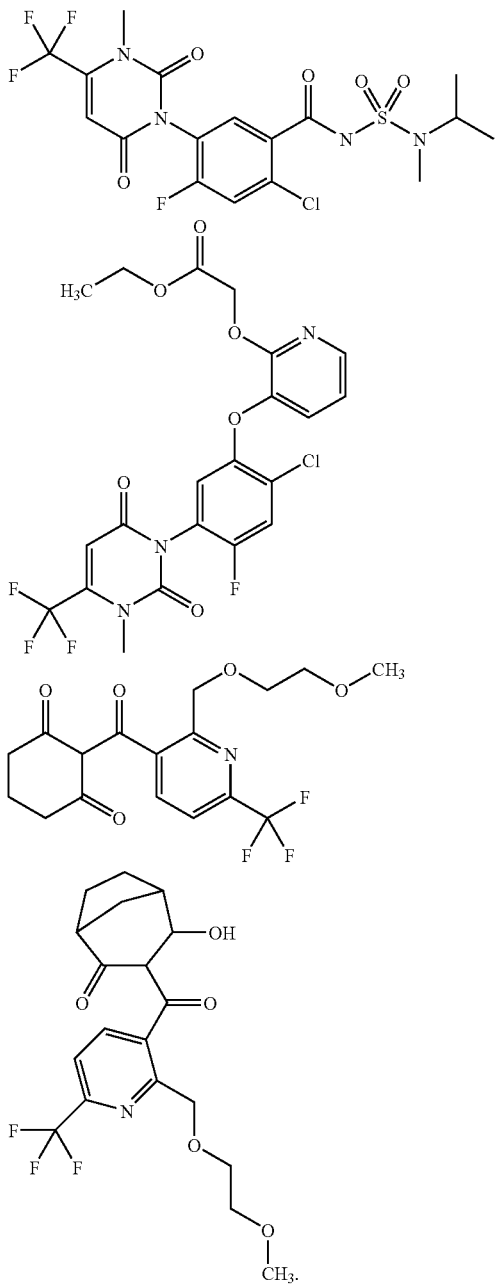

A mixture with other known active compounds, such as fungicides, insecticides, acaricides, nematicides, bird repellents, plant nutrients and soil conditioners, is also possible.

The active compounds/active compound combinations can be used as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds/active compound combinations according to the invention can be applied both before and after plant emergence. They can also be incorporated into the soil prior to sowing.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The substances/active compound combinations according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or Pseudoperonospora cubensis;
Plasmopara species, such as, for example, Plasmopara viticola;
Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea
(conidia form: Drechslera, syn: Helminthosporium);
Cochliobolus species, such as, for example, Cochliobolus sativus
(conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;

*Leptosphaeria* species, such as, for example, *Leptosphaeria nodorum*;
*Cercospora* species, such as, for example, *Cercospora canescens*;
*Alternaria* species, such as, for example, *Alternaria brassicae*; and
*Pseudocercosporella* species, such as, for example, *Pseudocercosporella herpotrichoides*.

The active compounds/active compound combinations according to the invention also have very good fortifying action in plants. Accordingly, they can be used for mobilizing the defenses of the plant against attack by unwanted microorganisms.

In the present context, plant-fortifying (resistance-inducing) substances are to be understood as meaning those substances which are capable of stimulating the defense system of plants such that, when the treated plants are subsequently inoculated with unwanted microorganisms, they show substantial resistance against these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds/active compound combinations are well tolerated by plants at the concentrations required for controlling plant diseases permits the treatment of above-ground parts of plants, of propagation stock and seeds, and of the soil.

The active compounds/active compound combinations according to the invention are also suitable for increasing the yield of crops. In addition, they show reduced toxicity and are well tolerated by plants.

At certain concentrations and application rates, the active compounds/active compound combinations according to the invention can, if appropriate, also be used as herbicides, for influencing plant growth and for controlling animal pests. If appropriate, they can also be used as intermediates and precursors for the synthesis of further active compounds.

In the protection of materials, the substances according to the invention can be employed for protecting industrial materials against infection with, and destruction by, unwanted microorganisms. Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds/active compound combinations can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds/active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, aftapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds/active compound combinations according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the compounds mentioned above.

A mixture with other known active compounds, such as herbicides, or with fertilizers and growth regulators, is also possible.

In addition, the compounds of the formula (I)/active compound combinations according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds/active compound combinations can be used as such, in the form of their formulations or the use forms prepared therefrom, such as ready-to-use solutions, suspensions, wettable powders, pastes, soluble powders, dusting agents and granules. Application is carried out in a customary manner, for example by pouring, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds/active compounds combinations according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The preparation and the use of the active compounds/active compound combinations according to the invention are illustrated by the examples below.

EXAMPLES

Example I-a-1

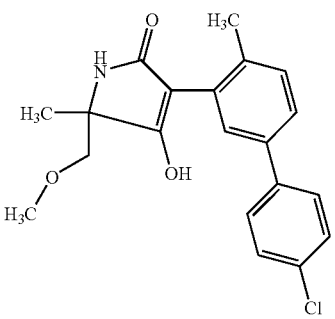

2.3 g (20 mmol) of potassium tert-butoxide are introduced under an argon atmosphere in 7 ml of N,N-dimethylacetamide (DMA) and this initial charge is admixed dropwise at 80° C. with 3.6 g (9 mmol) of the compound of Example II-1 in 7 ml of DMA and stirred at 80° C. for 1 hour. After end of reaction (thin-layer-chromatographic control (TLC control)) the reaction mixture is added to 80 ml of ice-water and at 0 to 10° C. is brought to a pH of 2 using 1N hydrochloric acid, and the precipitate is filtered off with suction, washed and dried.

Yield: 3.18 g (94% of theory), m.p. 211° C.

Example I-a-2

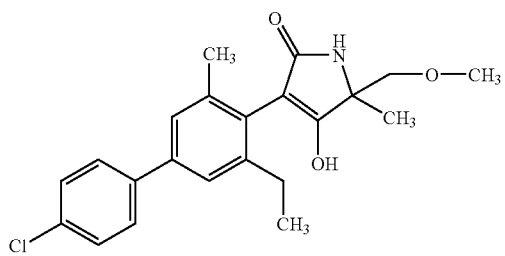

0.7 g of 3-(4-bromo-2-ethyl-6-methylphenyl)-5-methoxymethyl-5-methylpyrrolidine-2,4-dione and 0.71 g of 4-chlorophenylboronic acid are introduced in 5 ml of dimethoxyethane and this initial charge is admixed with 0.01 g of tetrakistriphenylphosphinepalladium and 15 ml of 7.5% strength $Na_2CO_3$ solution and stirred under reflux and under inert gas for 6 h. The mixture is added to water, adjusted to a pH of 1 using 1N HCl, stirred at room temperature for 10 minutes and filtered with suction on a frit.

Yield: 0.5 g (65% of theory), m.p. 206-209° C.

$^1$H-NMR (300 MHz, $d_6$-DMSO): δ=1.30 (d, 3H,

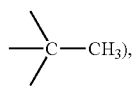

2.17 (d, 3H, aryl-$CH_3$) ppm.

In analogy to Examples (I-a-1) and (I-a-2) and in accordance with the general preparation details the following compounds are obtained of the formula (I-a)

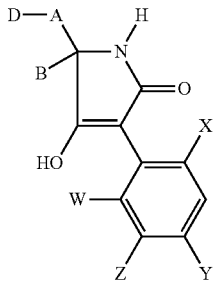

(I-a)

| Ex. No. | W | X | Y | Z | A | B | D | m.p. ° C. |
|---|---|---|---|---|---|---|---|---|
| I-a-3 | C₂H₅ | C₂H₅ | 4-Cl—Ph | H | —CH₂— | CH₃ | OCH₃ | 217-218 |
| I-a-4 | CH₃ | C₂H₅ | 4-CH₃—Ph | H | —CH₂— | CH₃ | OCH₃ | *1.28 (d, 3 H, 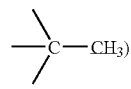 2.14 (d, 3 H, Ar—CH₃) |
| I-a-5 | CH₃ | CH₃ | 4-CH₃—Ph | H | —CH₂— | CH₃ | OCH₃ | 321-323 |
| I-a-6 | H | Cl | H | 4-Cl—Ph | —CH₂— | CH₃ | OCH₃ | 189 |
| I-a-7 | CH₃ | CH₃ | H | 4-Cl—Ph | —CH₂— | CH₃ | OCH₃ | 200 |
| I-a-8 | CH₃ | CH₃ | H | 4-F—Ph | —CH₂— | CH₃ | OCH₃ | 182 |
| I-a-9 | H | CH₃ | H | 4-CH₃—Ph | —CH₂— | CH₃ | OCH₃ | 66 |
| I-a-10 | CH₃ | CH₃ | H | 3,4-Cl₂—Ph | —CH₂— | CH₃ | OCH₃ | 112 |
| I-a-11 | H | CH₃ | H | 3-F, 4-Cl—Ph | —CH₂— | CH₃ | OCH₃ | decomp. |
| I-a-12 | H | CH₃ | H | 4-F—Ph | —CH₂— | CH₃ | OCH₃ | *1.31 (s, 3 H, CH₃), 2.20 (s, 3H, Ar—CH₃), 3.22 (s, 3 H, OCH₃) |
| I-a-13 | H | CH₃ | H | 4-C₂H₅—Ph | —CH₂— | CH₃ | OCH₃ | 105 |
| I-a-14 | H | CH₃ | H | 3,4-F₂—Ph | —CH₂— | CH₃ | OCH₃ | 85 |
| I-a-15 | H | CH₃ | H | 4-Cl—Ph | — | CH₃ | (tetrahydrofuran-2-yl) | 226 isomer mixture |
| I-a-16 | H | Cl | H | 4-Cl—Ph | — | CH₃ | (tetrahydrofuran-2-yl) | 216 isomer mixture |
| I-a-17 | H | CH₃ | H | 4-F—Ph | — | CH₃ | (tetrahydrofuran-2-yl) | 191 isomer mixture |
| I-a-18 | CH₃ | CH₃ | H | 4-F—Ph | — | CH₃ | (tetrahydrofuran-2-yl) | 243 isomer mixture |
| I-a-19 | CH₃ | CH₃ | H | 4-Cl—Ph | — | CH₃ | (tetrahydrofuran-2-yl) | 245 isomer mixture |
| I-a-20 | H | Cl | H | 4-F—Ph | —CH₂— | CH₃ | OCH₃ | 201 |
| I-a-21 | H | CH₃ | H | 4-Cl—Ph | —(CH₂)₂— | CH₃ | OCH₃ | 222 |
| I-a-22 | CH₃ | CH₃ | H | 4-F—Ph | —(CH₂)₂— | CH₃ | OCH₃ | 184 |
| I-a-23 | H | CH₃ | H | 4-F—Ph | —(CH₂)₂— | CH₃ | OCH₃ | 184 |
| I-a-24 | CH₃ | CH₃ | H | 4-Cl—Ph | —(CH₂)₂— | CH₃ | OCH₃ | 186 |

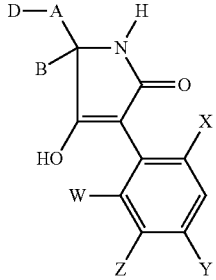

(I-a)

| Ex. No. | W | X | Y | Z | A | B | D | m.p. °C. |
|---|---|---|---|---|---|---|---|---|
| I-a-25 | CH₃ | CH₃ | H | 4-Cl—Ph | —CH₂— | CH₃ | (tetrahydrofuran-2-yl, isomer mixture) | 215 |
| I-a-26 | H | Cl | H | 4-F—Ph | —(CH₂)₂— | CH₃ | OCH₃ | 191 |
| I-a-27 | H | Cl | H | 4-Cl—Ph | —(CH₂)₂— | CH₃ | OCH₃ | 194 |

*$^1$H-NMR (400 MHz, d$_6$-DMSO): shifts δ in ppm

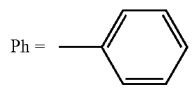

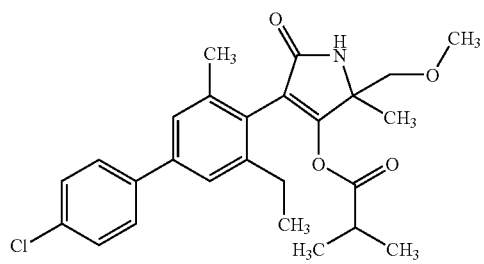

Example I-b-1

0.154 g (0.4 mmol) of the compound of Ex. I-a-2 are introduced in 8 ml of ethyl acetate and then this initial charge is admixed with 0.07 ml of triethylamine and 1.5 mg of DMAP and heated to 50° C. Subsequently 2 ml of a solution of 0.05 ml of isobutyryl chloride in ethyl acetate are added dropwise in 5 portions over the course of 30 min. The mixture is stirred under reflux for 6 h and then stirred at room temperature overnight. Saturated NaCl solution is added and the organic phase is separated off. After drying with sodium sulphate it is purified by column chromatography (ethyl acetate/n-heptane 1:4 to 4:1).

Yield: 0.127 g (70% of theory).

*$^1$H-NMR (400 MHz, CDCl₃): δ=1.00 (dd, 6H, CH(CH₃)₂), 2.30 (s, 3H, Ar—CH₃), 3.41 (d, 3H, OCH₃) ppm.

In analogy to Example (I-b-1) and in accordance with the general preparation details the following compounds are obtained of the formula (I-b)

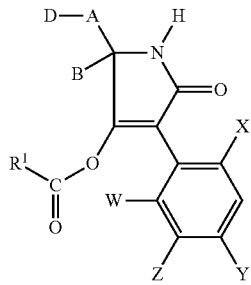

(I-b)

| Ex. No. | W | X | Y | Z | A | B | D | R¹ | m.p. °C. |
|---|---|---|---|---|---|---|---|---|---|
| I-b-2 | C₂H₅ | C₂H₅ | 4-Cl—Ph | H | —CH₂— | CH₃ | OCH₃ | i-C₃H₇ | **1.00 (dd, 6 H, CH(CH₃)₂), 2.59 (m, 5 H, ArCH₂, CH(CH₃)₂), 3.41 (s, 3 H, OCH₃) |

-continued

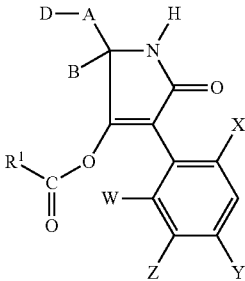

(I-b)

| Ex. No. | W | X | Y | Z | A | B | D | R¹ | m.p. ° C. |
|---|---|---|---|---|---|---|---|---|---|
| I-b-3 | $CH_3$ | $CH_3$ | 4-$CH_3$—Ph | H | —$CH_2$— | $CH_3$ | $OCH_3$ | $H_3CO$—$CH_2$— | *2.28 (d, 6 H, Ar$CH_3$), 3.37 (s, 3 H, O$CH_3$), 4.00 (q, 2 H, O—$CH_2$) |
| I-b-4 | $CH_3$ | $CH_3$ | 4-$CH_3$—Ph | H | —$CH_2$— | $CH_3$ | $OCH_3$ | i-$C_3H_7$ | **1.01 (d, 6 H, CH($CH_3$)$_2$), 2.29 (d, 6 H, Ar$CH_3$), 3.39 (s, 3 H, O$CH_3$) |
| I-b-5 | $CH_3$ | $C_2H_5$ | 4-$CH_3$—Ph | H | —$CH_2$— | $CH_3$ | $OCH_3$ | i-$C_3H_7$ | **0.96 (ddd, 6 H, CH($CH_3$)$_2$), 2.29 (d, 3 H, Ar—$CH_3$), 3.41 (s, 3 H, O—$CH_3$) |
| I-b-6 | H | $CH_3$ | H | 4-F—Ph | —$CH_2$— | $CH_3$ | $OCH_3$ | i-$C_3H_7$ | 152 |
| I-b-7 | H | $CH_3$ | H | 4-Cl—Ph | —$CH_2$— | $CH_3$ | $OCH_3$ | cyclopropyl | 75 |
| I-b-8 | H | $CH_3$ | H | 4-Cl—Ph | — | $CH_3$ | tetrahydrofuran-2-yl | i-$C_3H_7$ | 91 isomer mixture |
| I-b-9 | H | $CH_3$ | H | 3,4-$F_2$—Ph | —$CH_2$— | $CH_3$ | $OCH_3$ | i-$C_3H_7$ | 103 |
| I-b-10 | H | $CH_3$ | H | 3-F, 4-Cl—Ph | —$CH_2$— | $CH_3$ | $OCH_3$ | i-$C_3H_7$ | 157 |
| I-b-11 | H | $CH_3$ | H | 4-$CH_3$—Ph | —$CH_2$— | $CH_3$ | $OCH_3$ | i-$C_3H_7$ | 59 |
| I-b-12 | H | Cl | H | 4-F—Ph | —$CH_2$— | $CH_3$ | $OCH_3$ | i-$C_3H_7$ | 166 |
| I-b-13 | H | $CH_3$ | H | 4-Cl—Ph | —$CH_2$— | $CH_3$ | $OCH_3$ | i-$C_3H_7$ | ***0.94 ("t", 6 H, CH($CH_3$)$_2$), 3.31 (s, 3 H, O$CH_3$), 3.45 (ABq, 2 H, $CH_2$O$CH_3$) |
| I-b-14 | $CH_3$ | $CH_3$ | H | 4-F—Ph | —$CH_2$— | $CH_3$ | $OCH_3$ | i-$C_3H_7$ | 76 |
| I-b-15 | $CH_3$ | $CH_3$ | H | 4-Cl—Ph | — | $CH_3$ | tetrahydrofuran-2-yl | i-$C_3H_7$ | ***0.90-0.97 (m, 6 H, CH($CH_3$)$_2$), 2.15-2.20 (4 s, 3 H, Ar—$CH_3$), 7.21-7.24 (AA', 2 H, Ar—H) 7.45-7.47 (BB', 2 H, Ar—H) |
| I-b-16 | H | $CH_3$ | H | 4-F—Ph | — | $CH_3$ | tetrahydrofuran-2-yl | i-$C_3H_7$ | ***2.59 (zm, 1 H, $CH$($CH_3$)$_2$), 3.94-3.98 (m, 1 H, $CH$O), 7.57-7.62 (m, 2 H, Ar—H) |
| I-b-17 | H | Cl | H | 4-Cl—Ph | — | $CH_3$ | tetrahydrofuran-2-yl | i-$C_3H_7$ | ***1.37, 1.40, 1.45 (3 s, 3 H, $CH_3$) 2.66 (zm, 1 H, $CH$($CH_3$)$_2$), 3.95-3.98 (m, 1 H, O—$CH$) |
| I-b-18 | H | $CH_3$ | H | 4-Cl—Ph | —$CH_2$— | $CH_3$ | $OCH_3$ | 4-Cl—Ph | ***1.42 (s, 3 H, $CH_3$) 2.24 (s, 3 H, Ar—$CH_3$) 3.51-3.59 (ABq, 2 H, O$CH_2$) 7.58 (AA'd, 2 H, Ar—H) 7.93 (BB'd, 2 H, Ar—H) |
| I-b-19 | H | Cl | H | 4-Cl—Ph | —$CH_2$— | $CH_3$ | $OCH_3$ | $CH_3$ | decomp. |
| I-b-20 | H | Cl | H | 4-Cl—Ph | —$CH_2$— | $CH_3$ | $OCH_3$ | i-$C_3H_7$ | 167 |
| I-b-21 | $CH_3$ | $CH_3$ | H | 4-F—Ph | — | $CH_3$ | tetrahydrofuran-2-yl | i-$C_3H_7$ | ***1.99, 2.02 (2 s, 3 H, Ar—$CH_3$) 2.17, 2.19 (2 s, 3 H, Ar—$CH_3$), 3.94-3.98 (m, 1 H, $CH$O) |
| I-b-22 | H | $CH_3$ | H | 4-Cl—Ph | —$(CH_2)_2$— | $CH_3$ | $OCH_3$ | i-$C_3H_7$ | ***1.37 (s, 3 H, $CH_3$) 2.62 (m, 1 H,$CH$($CH_3$)$_2$, 3.23 (s, 3 H, O$CH_3$) |

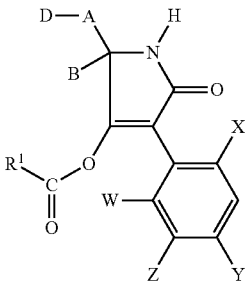

(I-b)

| Ex. No. | W | X | Y | Z | A | B | D | R¹ | m.p. °C. |
|---|---|---|---|---|---|---|---|---|---|
| I-b-23 | $CH_3$ | $CH_3$ | H | 4-Cl—Ph | —$(CH_2)_2$— | $CH_3$ | $OCH_3$ | $i$-$C_3H_7$ | ***0.93-0.96 (8 s, 6 H, CH($\underline{CH_3})_2$, 1.38, 1.40 (2 s, 3 H, $\underline{CH_3}$), 2.15, 2.19 (2 s, 3 H, Ar—$\underline{CH_3}$) 3.19, 3.23 (2 s, 3 H, O$\underline{CH_3}$) |

*$^1$H-NMR (300 MHz, CDCl$_3$): shifts δ in ppm
**$^1$H-NMR (400 MHz, CDCl$_3$): shifts δ in ppm
***$^1$H-NMR (400 MHz, d$_6$-DMSO): shifts δ in ppm Example I-c-1

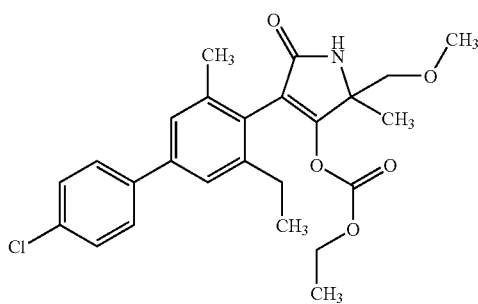

0.15 g of the compound of Example I-a-2 and 0.06 ml of triethylamine are introduced in 8 ml of dichloromethane and this initial charge is stirred at room temperature for 5 minutes, admixed with 0.046 g of ethyl chloroformate and stirred at room temperature overnight. After end of reaction (TLC control), 5 ml of Na$_2$CO$_3$ solution are added and the mixture is stirred at room temperature for 10 minutes, separated via an extraction cartridge and concentrated on a rotary evaporator. Purification is accomplished by column chromatography using ethyl acetate/n-heptane (1:4 to 4:1).

Yield: 0.172 g (97% of theory).

*$^1$H-NMR (300 MHz, CDCl$_3$): δ=2.24 (s, 3H, Ar—$\underline{CH_3}$), 3.3 (d, 3H, O$\underline{CH_3}$), 3.96 (q, 2H, O—$\underline{CH_2}$—CH$_3$).

In analogy to Example (I-c-1) and in accordance with the general preparation details the following compounds are obtained of the formula (I-c)

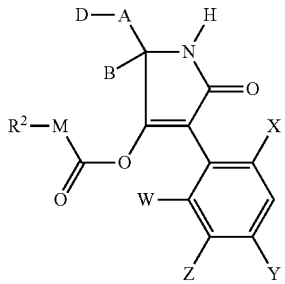

(I-c)

| Ex. No. | W | X | Y | Z | A | B | D | M | R² | m. p. °C. |
|---|---|---|---|---|---|---|---|---|---|---|
| I-c-2 | $C_2H_5$ | $C_2H_5$ | 4-Cl—Ph | H | —$CH_2$— | $CH_3$ | $OCH_3$ | O | $C_2H_5$ | *2.63 (m, 4 H, Ar-$\underline{CH_2}$, 3.38 (s, 3 H, O$\underline{CH_3}$, 4.05 (q, 2 H, O$\underline{CH_2}$—CH$_3$) |
| I-c-3 | $CH_3$ | $CH_3$ | 4-$CH_3$—Ph | H | —$CH_2$— | $CH_3$ | $OCH_3$ | O | $C_2H_5$ | **2.38 (s, 3 H, Ar—$\underline{H}$), 3.41 (s, 3 H, O$\underline{CH_3}$) |
| I-c-4 | $CH_3$ | $C_2H_5$ | 4-$CH_3$—Ph | H | —$CH_2$— | $CH_3$ | $OCH_3$ | O | $C_2H_5$ | **2.59 (m, 2 H, Ar—$\underline{CH_3}$), 3.41 (d, 3 H, O$\underline{CH_3}$) 4.03 (q, 2 H, O$\underline{CH_2}$CH$_3$) |

-continued

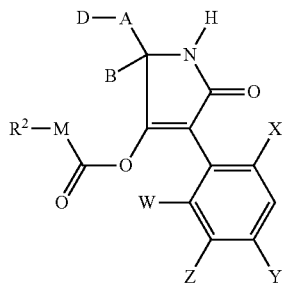

(I-c)

| Ex. No. | W | X | Y | Z | A | B | D | M | R² | m. p. ° C. |
|---|---|---|---|---|---|---|---|---|---|---|
| I-c-5 | H | CH₃ | H | 4-Cl—Ph | —CH₂— | CH₃ | OCH₃ | O | C₂H₅ | wax |
| I-c-6 | H | Cl | H | 4-Cl—Ph | —CH₂— | CH₃ | OCH₃ | O | C₂H₅ | 154 |
| I-c-7 | CH₃ | CH₃ | H | 4-Cl—Ph | —CH₂— | CH₃ | OCH₃ | O | C₂H₅ | wax |
| I-c-8 | H | CH₃ | H | 4-F—Ph | —CH₂— | CH₃ | OCH₃ | O | CH₃ | ***1.37 (s, 3 H, C$\underline{H}_3$), 2.21 (s, 3 H, ArC$\underline{H}_3$), 3.32 (s, 3 H, OC$\underline{H}_3$) 3.60 (s, 3 H, CO₂C$\underline{H}_3$), |
| I-c-9 | CH₃ | CH₃ | H | 3,4-Cl₂—Ph | —CH₂— | CH₃ | OCH₃ | O | CH₃ | 68 |
| I-c-10 | H | Cl | H | 4-F—Ph | —CH₂— | CH₃ | OCH₃ | O | C₂H₅ | 61 |
| I-c-11 | H | Cl | H | 4-F—Ph | —CH₂— | CH₃ | OCH₃ | O | CH₃ | 132 |
| I-c-12 | H | CH₃ | H | 4-F—Ph | — | CH₃ | tetrahydrofuran-2-yl | O | CH₃ | **1.37, 1.40, 1.47 (3 s, 3 H, C$\underline{H}_3$), 1.81-1.99 (m, 4 H, (C$\underline{H}_2$)₂) |
| I-c-13 | H | Cl | H | 4-Cl—Ph | — | CH₃ | tetrahydrofuran-2-yl | O | CH₃ | **3.62 (2 s, 3 H, CO₂C$\underline{H}_3$), 7.63-7.7 (m, 3 H, Ar—$\underline{H}$) 3.56, 3.57 (2 s, 3 H, CO₂C$\underline{H}_3$) |
| I-c-14 | H | CH₃ | H | 4-CH₃—Ph | —CH₂— | CH₃ | OCH₃ | O | CH₃ | 127 |
| I-c-15 | H | CH₃ | H | 4-Cl—Ph | —CH₂— | CH₃ | OCH₃ | O | Ph-CH₂ | 164 |
| I-c-16 | H | CH₃ | H | 4-Cl—Ph | —CH₂— | CH₃ | OCH₃ | O | CH₃ | 146 |
| I-c-17 | H | CH₃ | H | 4-Cl—Ph | —(CH₂)₂— | CH₃ | OCH₃ | O | C₂H₅ | ***0.94 (t, 3 H, CH₂C$\underline{H}_3$), 1.96 (t, 2 H, C$\underline{H}_2$CH₂—O) 3.96 (q, 2 H, O—C$\underline{H}_2$CH₃) |
| I-c-18 | H | CH₃ | H | 4-F—Ph | —(CH₂)₂— | CH₃ | OCH₃ | O | CH₃ | ***1.41 (s, 3 H, C$\underline{H}_3$), 1.96 (t, 2 H, C$\underline{H}_2$—CH₂—O) 3.22 (s, 3 H, OC$\underline{H}_3$) 3.56 (s, 3 H, CO₂C$\underline{H}_3$) |
| I-c-19 | CH₃ | CH₃ | H | 4-F—Ph | —(CH₂)₂— | CH₃ | OCH₃ | O | CH₃ | ***1.41, 1.43 (2 s, 3 H, C$\underline{H}_3$), 2.14, 2.18 (2 s, 3 H, Ar—C$\underline{H}_3$) 3.43 (m, 2 H, O—C$\underline{H}_2$) 3.56 (s, 3 H, CO₂C$\underline{H}_3$) |
| I-c-20 | H | CH₃ | H | 4-Cl—Ph | —(CH₂)₂— | CH₃ | OCH₃ | O | CH₃ | ***1.96 (t, 2 H, C$\underline{H}_2$—CH₂—O), 2.23 (s, 3 H, Ar—C$\underline{H}_3$) 3.41 (2 m, 2 H, O—C$\underline{H}_2$) 3.56 (s, 3 H, CO₂C$\underline{H}_3$) |
| I-c-21 | CH₃ | CH₃ | H | 4-Cl—Ph | —(CH₂)₂— | CH₃ | OCH₃ | O | CH₃ | ***1.41, 1.43 (2 s, 3 H, C$\underline{H}_3$), 2.14, 2.18 (2 s, 3 H, ArC$\underline{H}_3$) 1.97, 2.02 (2 s, 3 H, Ar—C$\underline{H}_3$) 3.56 (s, 3 H, CO₂C$\underline{H}_3$) |

*¹H-NMR (300 MHz, CDCl₃): shifts δ in ppm
**¹H-NMR (400 MHz, CDCl₃): shifts δ in ppm
***¹H-NMR (400 MHz, d₆-DMSO): shifts δ in ppm

Example II-1

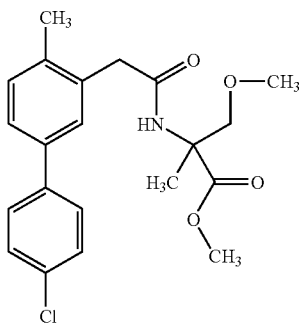

Under argon, 3.03 g of methyl 2-amino-2-methoxymethylpropionate×HCl (16.5 mmol) are introduced in 75 ml of anhydrous tetrahydrofuran. At 20° C. this initial charge is admixed dropwise with 4.6 ml (33 mmol) of triethylamine. It is stirred for 5 minutes and admixed at 20° C. with 3.9 g of 3-(4-chlorophenyl)-6-methylphenylacetic acid (15 mmol). After 15 minutes 3.45 ml of triethylamine (25 mmol) are added dropwise, followed immediately by 0.93 ml of phosphorus oxychloride (10 mmol); the solution ought to boil moderately. It is stirred under reflux for 30 minutes. After end of reaction (TLC control) purification is accomplished by column chromatography on silica gel (dichloromethane:ethyl acetate=10:1).

Yield: 3.6 g (60% of theory), m.p. 107° C.

In analogy to Example (II-1) and in accordance with the general preparation details the following compounds are obtained of the formula (II)

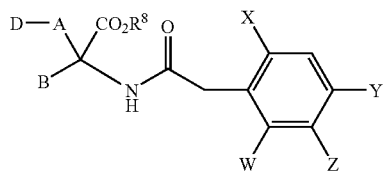

| Ex. No. | W | X | Y | Z | A | B | D | $R^8$ | m. p. ° C. |
|---|---|---|---|---|---|---|---|---|---|
| II-2 | $CH_3$ | $CH_3$ | H | 4-Cl—Ph | —$CH_2$— | $CH_3$ | $OCH_3$ | $CH_3$ | *1.44 (s, 3 H, C$\underline{H}_3$), 2.14, 2.33 (2 s, each 3 H, Ar—C$\underline{H}_3$), 3.25 (s, 3 H, $CH_2$—O—C$\underline{H}_3$), 3.6 (s, 3 H, $CO_2$C$\underline{H}_3$) |
| II-3 | H | Cl | H | 4-Cl—Ph | —$CH_2$— | $CH_3$ | $OCH_3$ | $CH_3$ | *1.46 (s, 3 H, C$\underline{H}_3$), 3.26 (s, 3 H, $CH_2$—O—C$\underline{H}_3$), 3.61 (s, 3 H, $CO_2$C$\underline{H}_3$), 3.69 (s, 2 H, C$\underline{H}_2$CO) |
| II-4 | H | $CH_3$ | H | 4-Cl—Ph | — | $CH_3$ | (tetrahydrofuran-2-yl) | $CH_3$ | 113 isomer mixture |
| II-5 | H | $CH_3$ | H | 3,4-$F_2$—Ph | —$CH_2$— | $CH_3$ | $OCH_3$ | $CH_3$ | 111 |
| II-6 | H | $CH_3$ | H | 4-$CH_3$—Ph | —$CH_2$— | $CH_3$ | $OCH_3$ | $CH_3$ | 133 |
| II-7 | $CH_3$ | $CH_3$ | H | 3,4-$Cl_2$—Ph | —$CH_2$— | $CH_3$ | $OCH_3$ | $CH_3$ | **1.39 (s, 3 H, C$\underline{H}_3$), 2.11, 2.28 (s, 6 H, Ar—C$\underline{H}_3$), 3.27 (s, 3 H, OC$\underline{H}_3$), 3.55 (s, 3 H, $CO_2$C$\underline{H}_3$) |
| II-8 | $CH_3$ | $CH_3$ | H | 4-F—Ph | —$CH_2$— | $CH_3$ | $OCH_3$ | $CH_3$ | **2.09, 2.27 (2 s, 6 H, Ar—C$\underline{H}_3$), 3.26 (s, 3 H, OC$\underline{H}_3$), 7.18-7.28 (m, 4 H, 4-F-Ar—$\underline{H}$) |
| II-9 | H | $CH_3$ | H | 3-F, 4-Cl—Ph | —$CH_2$— | $CH_3$ | $OCH_3$ | $CH_3$ | 125 |
| II-10 | H | $CH_3$ | H | 4-F—Ph | —$CH_2$— | $CH_3$ | $OCH_3$ | $CH_3$ | 114 |
| II-11 | H | Cl | H | 4-$C_2H_5$—Ph | —$CH_2$— | $CH_3$ | $OCH_3$ | $CH_3$ | 97 |
| II-12 | $CH_3$ | $CH_3$ | H | 3-F, 4-Cl—Ph | —$CH_2$— | $CH_3$ | $OCH_3$ | $CH_3$ | **1.39 (s, 3 H, C$\underline{H}_3$), 3.55 (s, 3 H, $CO_2CH_3$), 7.59 ("t", 1, Ar—$\underline{H}$) |
| II-13 | H | $CH_3$ | H | 4-F—Ph | — | $CH_3$ | (tetrahydrofuran-2-yl) | $CH_3$ | ***1.44, 1.47 (2 s, 3 H, C$\underline{H}_3$), 2.32 (2 s, 3 H, Ar—C$\underline{H}_3$), 3.93-3.98 (m, 1 H, O—C$\underline{H}$) |
| II-14 | $CH_3$ | $CH_3$ | H | 4-F—Ph | — | $CH_3$ | (tetrahydrofuran-2-yl) | $CH_3$ | ***1.45-1.47 (4 s, 3 H, C$\underline{H}_3$), 2.14, 2.15 (2 s, 3 H, Ar—C$\underline{H}_3$), 2.33, 2.34 (3 s, 3 H, Ar—C$\underline{H}_3$), |

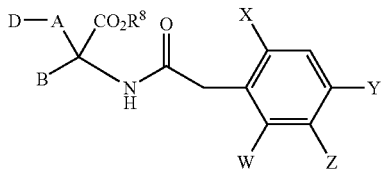

(II)

| Ex. No. | W | X | Y | Z | A | B | D | R$^8$ | m. p. ° C. |
|---|---|---|---|---|---|---|---|---|---|
| II-15 | CH$_3$ | CH$_3$ | H | 4-Cl—Ph | — | CH$_3$ | (tetrahydrofuran-2-yl) | CH$_3$ | ***1.44, 1.45 (2 s, 3 H, C$\underline{H}_3$), |
| II-16 | H | Cl | H | 4-Cl—Ph | — | CH$_3$ | (tetrahydrofuran-2-yl) | CH$_3$ | ***1.45-4.48 (2 s, 3 H, C$\underline{H}_3$), 7.44-7.49 (m, 4 H, Ar—$\underline{H}$), 7.58-7.63 (m, 3 H, Ar—$\underline{H}$), |
| II-17 | H | Cl | H | 4-F—Ph | —CH$_2$— | CH$_3$ | OCH$_3$ | CH$_3$ | 130 |
| II-18 | CH$_3$ | CH$_3$ | H | 4-Cl—Ph | —(CH$_2$)$_2$— | CH$_3$ | OCH$_3$ | CH$_3$ | **1.40 (s, 3 H, C$\underline{H}_3$), 2.11, 2.29 (2 s, 6 H, Ar—C$\underline{H}_3$), 3.34 (t, 2 H, O—C$\underline{H}_2$), 3.54 (s, 3 H, CO$_2$C$\underline{H}_3$) |
| II-19 | H | CH$_3$ | H | 4-Cl—Ph | —(CH$_2$)$_2$— | CH$_3$ | OCH$_3$ | CH$_3$ | **2.28 (s, 3 H, C$\underline{H}_3$), 3.29-3.34 (m, 2 H, C$\underline{H}_2$), 3.53 (s, 5 H, C$\underline{H}_2$CO, CO$_2$C$\underline{H}_3$) |
| II-20 | CH$_3$ | CH$_3$ | H | 4-F—Ph | —(CH$_2$)$_2$— | CH$_3$ | OCH$_3$ | CH$_3$ | **2.10, 2.28 (2 s, 6 H, Ar—C$\underline{H}_3$), 3.34 (t, 2 H, O—C$\underline{H}_2$), 3.59 (s, 2 H, COC$\underline{H}_2$), 7.19-7.28 (m, 4 H, F—Ar—$\underline{H}$) |
| II-21 | H | CH$_3$ | H | 4-F—Ph | —(CH$_2$)$_2$— | CH$_3$ | OCH$_3$ | CH$_3$ | **1.35 (s, 3 H, C$\underline{H}_3$), 2.28 (s, 3 H, Ar—C$\underline{H}_3$), 3.32 (2 m, 2 H, OC$\underline{H}_2$), 7.62-7.65 (m, 2 H, Ar—$\underline{H}$) |
| II-22 | CH$_3$ | CH$_3$ | H | 4-Cl—Ph | —CH$_2$— | CH$_3$ | (tetrahydrofuran-2-yl) | CH$_3$ | **1.44, 1.47 (2 s, 3 H, C$\underline{H}_3$), 2.15, 2.16 (2 s, 3 H, Ar—C$\underline{H}_3$), 2.33, 2.34 (2 s, 3 H, Ar—C$\underline{H}_3$), 3.60, 3.61 (2 s, 3 H, CO$_2$C$\underline{H}_3$) |
| II-23 | H | Cl | H | 4-F—Ph | —(CH$_2$)$_2$— | CH$_3$ | OCH$_3$ | CH$_3$ | **1.49 (s, 3 H, C$\underline{H}_3$), 3.10 (s, 3 H, OC$\underline{H}_3$), 7.19 (2 m, 2 H, Ar—$\underline{H}$) |
| II-24 | H | Cl | H | 4-Cl—Ph | —(CH$_2$)$_2$— | CH$_3$ | OCH$_3$ | CH$_3$ | **1.49 (s, 3 H, C$\underline{H}_3$), 3.10 (s, 3 H, C$\underline{H}_3$), 3.60 (s, 3 H, CO—C$\underline{H}_3$), 3.67 (s, 2 H, CO—C$\underline{H}_2$) |

\*$^1$H-NMR (300 MHz, CDCl$_3$): shifts δ in ppm
\*\*$^1$H-NMR (400 MHz, d$_6$-DMSO): shifts δ in ppm
\*\*\*$^1$H-NMR (400 Mhz, CD$_3$—CN): shifts δ in ppm

Example XIII-1

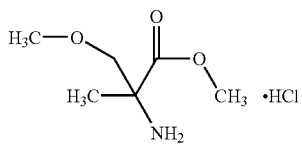

Under argon, 189.3 g of the compound of Example XVI-1 are introduced in 4.4 l of methanol at 0° C. to 5° C. and this initial charge is admixed slowly dropwise with 230 ml of thionyl chloride. It is stirred at 0° C. for 30 min then at 40° C. for approximately 10 h and is left at room temperature overnight. It is cooled to 5° C., the precipitate is filtered off with suction and the solvent is removed on a rotary evaporator.

Yield: 197.4 g (96% of theory).
$^1$H-NMR (400 MHz, d$_6$-DMSO): δ=1.45 (s, 3H, CH$_3$), 3.31 (s, 1H, OC$\underline{H}_3$), 3.69 (s, 2H, O—C$\underline{H}_2$), 3.76 (s, 3H, $\overline{COO}$ CH$_3$) ppm.

In analogy to Example XIII-1 the new amino acid esters of the formula (XIII-2) to (XIII-3) are obtained in the form of their salts

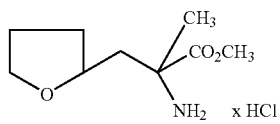

(XIII-2)

$^1$H-NMR (400 MHz, d$_6$-DMSO): δ=1.43, 1.5 (2s, 3H, C$\underline{H}_3$), 3.75 (s, 3H, CO$_2$C$\underline{H}_3$), 4.12 (m, 1H, OC$\underline{H}$) ppm and (XIII-3)

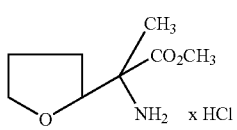

$^1$H-NMR (400 MHz, d$_6$-DMSO): δ=1.52, 1.55 (2s, 3H, C$\underline{H_3}$), 3.71, 3.75 (2s, 3H, CO$_2$C$\underline{H_3}$), 3.85, 4.03 (m, 1H, OC$\underline{H}$) ppm.

Example XVI-1

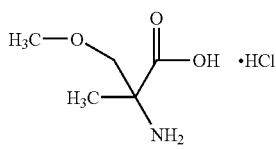

Under argon, 176.5 g of 5-methoxymethyl-5-methylhydantoin are suspended in 1700 ml of 30% strength KOH and the suspension is stirred under reflux overnight.

Concentrate to approximately 25% of the volume on a rotary evaporator; acidify at 0-10° C. using concentrated HCl, concentrate on a rotary evaporator, and dry. The white powder is reacted further directly for the preparation of Example XIII-1.

In analogy to Example XVI-1 the new amino acids of the formula (XVI-2) to (XVI-3) are obtained

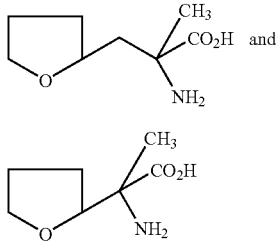

5-Methoxymethyl-5-methylhydantoin (XX-1)

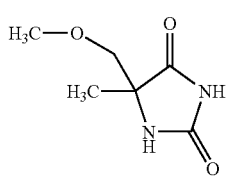

Under argon inert gas, ammonium carbonate (134.5 g) and sodium cyanide (16.17 g) are introduced in 560 ml of water. Beginning at room temperature, the methoxyacetone (26.4 g) is added dropwise and the reaction mixture is stirred at 55° C. to 60° C. over four hours and then stirred at 0° C. to 5° C. for two hours.

The solid is filtered off with suction and dried.

Yield: 21.55 g (45% of theory).

In analogy to Example (XX-1) the new hydantoins (XX-2) to (XX-3) are obtained

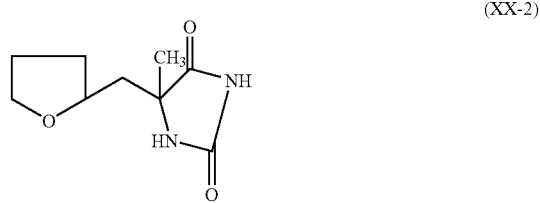

$^1$H-NMR (400 MHz, d$_6$-DMSO): δ=1.25, 1.40 (2s, 3H, C$\underline{H_3}$), 3.73 (m, 2H, OC$\underline{H_2}$), 3.97 (m, 1H, C$\underline{H}$O) ppm and

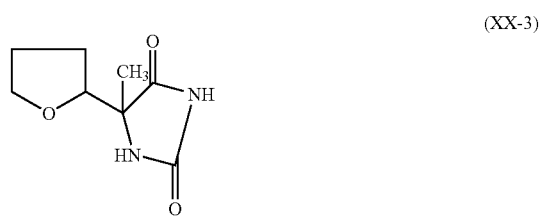

$^1$H-NMR (400 MHz, d$_6$-DMSO): δ=1.20, 1.22 (2s, 3H, C$\underline{H_3}$), 3.50-3.86 (m, 3H, O—C$\underline{H_2}$, O—C$\underline{H}$) ppm.

USE EXAMPLES

Example No. 1

Myzus Test (MYZUPE Spray Treatment)

| Solvent: | 78 parts by weight of acetone |
|---|---|
| | 1.5 parts by weight of dimethylformamide |
| Emulsifier: | 0.5 part by weight of alkylaryl polyglycol ether |

A suitable preparation of active compound is prepared by mixing 1 part by weight of active compound with the stated amounts of solvent and emulsifier and diluting the concentrate with emulsifier-containing water to the desired concentration.

Leaf discs of Chinese cabbage (*Brassica pekinensis*) infested by all stages of the green peach aphid (*Myzus persicae*) are sprayed with a preparation of active compound at the desired concentration.

After the desired time the effect in % is determined. 100% means that all of the aphids have been killed; 0% means that no aphids have been killed.

In this test the following compounds, for example, of the Preparation Examples, applied at a rate of 500 g/ha, show an activity of ≧80%: I-a-1, I-a-6, I-a-8, I-a-9, I-a-10, I-a-11, I-a-12, I-a-14, I-a-15, I-a-16, I-a-17, I-a-18, I-a-19, I-a-20, I-a-21, I-a-22, I-a-23, I-a-24, I-a-25, I-a-26, I-a-27, I-b-6, I-b-7, I-b-8, I-b-9, I-b-10, I-b-12, I-b-13, I-b-14, I-b-15, I-b-

16, I-b-17, I-b-18, I-b-22, I-b-23, I-c-5, I-c-6, I-c-7, I-c-8, I-c-9, I-c-10, I-c-11, I-c-12, I-c-13, I-c-17, I-c-18, I-c-19, I-c-20, I-c-21.

Example No. 2

Phaedon Test (PHAECO Spray Treatment)

| Solvent: | 78 parts by weight of acetone |
| --- | --- |
|  | 1.5 parts by weight of dimethylformamide |
| Emulsifier: | 0.5 part by weight of alkylaryl polyglycol ether |

A suitable preparation of active compound is prepared by mixing 1 part by weight of active compound with the stated amounts of solvent and emulsifier and diluting the concentrate with emulsifier-containing water to the desired concentration.

Leaf discs of Chinese cabbage (*Brassica pekinensis*) are sprayed with a preparation of active compound at the desired concentration and after they have dried are populated with larvae of the mustard beetle (*Phaedon cochleariae*).

After the desired time the effect in % is determined. 100% means that all of the beetle larvae have been killed; 0% means that no beetle larvae have been killed.

In this test the following compounds, for example, of the Preparation Examples, applied at a rate of 500 g/ha, show an activity of ≧80%: I-a-1, I-a-2, I-a-6, I-a-7, I-a-8, I-a-9, I-a-10, I-a-11, I-a-12, I-a-13, I-a-14, I-a-15, I-a-20, I-a-21, I-a-22, I-a-23, I-a-26, I-a-27, I-b-7, I-b-8, I-b-9, I-b-12, I-b-13, I-b-14, I-b-18, I-b-23, I-c-5, I-c-6, I-c-7, I-c-8, I-c-9, I-c-10, I-c-11, I-c-12, I-c-13.

Example No. 3

*Tetranychus* Test, OP-Resistant (TETRUR Spray Treatment)

| Solvent: | 7 parts by weight of dimethylformamide |
| --- | --- |
| Emulsifier: | 2 parts by weight of alkylaryl polyglycol ether |

A suitable preparation of active compound is prepared by mixing 1 part by weight of active compound with the stated amounts of solvent and emulsifier and diluting the concentrate with emulsifier-containing water to the desired concentration.

Bean plants (*Phaseolus vulgaris*) heavily infested by all stages of the greenhouse red spider mite (*Tetranychus urticae*) are immersed in a preparation of active compound at the desired concentration.

After the desired time the effect in % is determined. 100% means that all of the spider mites have been killed; 0% means that no spider mites have been killed.

In this test the following compounds, for example, of the Preparation Examples, applied at a rate of 100 g/ha, show an activity of ≧80%: I-a-1, I-a-2, I-a-7, I-a-14, I-a-15, I-a-16, I-a-18, I-a-19, I-a-21, I-a-22, I-a-23, I-a-24, I-a-25, I-a-27, I-b-6, I-b-7, I-b-8, I-b-9, I-b-10, I-b-16, I-b-17, I-b-18, I-b-22, I-b-23, I-c-1, I-c-5, I-c-6, I-c-8, I-c-9, I-c-11, I-c-12, I-c-13, I-c-17, I-c-18, I-c-19, I-c-20, I-c-21.

Example No. 4

*Spodoptera frugiperda* Test (SPODFR Spray Treatment)

| Solvent: | 78 parts by weight of acetone |
| --- | --- |
|  | 1.5 parts by weight of dimethylformamide |
| Emulsifier: | 0.5 part by weight of alkylaryl polyglycol ether |

A suitable preparation of active compound is prepared by mixing 1 part by weight of active compound with the stated amounts of solvent and emulsifier and diluting the concentrate with emulsifier-containing water to the desired concentration.

Leaf discs of maize (*Zea mays*) are sprayed with a preparation of active compound at the desired concentration and after they have dried are populated with caterpillars of the army worm (*Spodoptera frugiperda*).

After the desired time the effect in % is determined. 100% means that all of the caterpillars have been killed; 0% means that no caterpillars have been killed.

In this test the following compounds, for example, of the Preparation Examples, applied at a rate of 500 g/ha, show an activity of ≧80%: I-a-1, I-a-6, I-a-7, I-a-8, I-a-9, I-a-10, I-a-11, I-a-12, I-a-14, I-a-15, I-a-16, I-a-17, I-a-18, I-a-19, I-a-20, I-a-21, I-a-26, I-a-27, I-b-6, I-b-7, I-b-8, I-b-9, I-b-10, I-b-12, I-b-13, I-b-14, I-b-15, I-b-16, I-b-17, I-b-18, I-b-22, I-b-23, I-c-5, I-c-6, I-c-7, I-c-10, I-c-1, I-c-12, I-c-13, I-c-17, I-c-20, I-c-21.

Example No. 5

*Meloidogyne* Test (MELGIN Spray Treatment)

| Solvent: | 80 parts by weight of acetone |
| --- | --- |

A suitable preparation of active compound is prepared by mixing 1 part by weight of active compound with the stated amount of solvent and diluting the concentrate with water to the desired concentration.

Containers are filled with sand, a solution of active compound, *Meloidogyne incognita* egg/larvae suspension and lettuce seeds. The lettuce seeds germinate and the plants develop. On the roots, galls develop.

After the desired time, the nematicidal effect is determined in % from the formation of galls. 100% means that no galls were found; 0% means that the number of galls on the treated plants corresponds to that of the untreated control.

In this test the following compounds, for example, of the Preparation Examples show an activity of ≧80% when applied at a rate of 20 ppm: I-a-8, I-a-11, I-a-22, I-a-23.

Example No. 6

*Lucilia cuprina* Test (LUCICU)

| Solvent: | dimethyl sulphoxide |
|---|---|

A suitable preparation of active compound is prepared by mixing 1 part by weight of active compound with the stated amount of water and diluting the concentrate with water to the desired concentration.

Containers with horse meat which has been treated with the preparation of active compound at the desired concentration are populated with *Lucilia cuprina* larvae.

After the desired time the destruction in % is determined. 100% means that all of the larvae have been killed; 0% means that no larvae have been killed.

In this test the following compounds, for example, of the Preparation Examples exhibit an activity of ≧80% when applied at a rate of 100 ppm: I-a-1, I-a-6, I-a-7, I-c-5, I-c-6, I-c-7.

Example No. 7

*Boophilus microplus* Test (BOOPMI Injection)

| Solvent: | dimethyl sulphoxide |
|---|---|

A suitable preparation of active compound is prepared by mixing 1 part by weight of active compound with the stated amount of solvent and diluting the concentrate with solvent to the desired concentration.

The solution of active compound is injected into the abdomen (*Boophilus microplus*) and the animals are transferred into dishes and stored in a climatized room.

After the desired time the effect in % is determined. In this case 100% means that none of the ticks has laid fertile eggs.

In this test the following compounds, for example, of the Preparation Examples show an activity of ≧80% when applied at a rate of 20 μg/animal: I-a-1, I-a-6, I-a-7, I-c-5, I-c-6, I-c-7.

Example No. 8

1. Pre-Emergence Herbicidal Effect

Seeds of monocotyledonous and dicotyledonous weed plants and crop plants are placed in sandy loam soil in wood fibre pots and are covered with earth. The test compounds, formulated in the form of wettable powders (WP), are then applied, in the form of an aqueous suspension, at a water application rate of 600 l/ha (converted) and with addition of 0.2% wetting agent, in different dosages, to the surface of the covering earth.

After the treatment the pots are placed in a greenhouse and held under good growth conditions for the test plants. The visual assessment of the emergence damage on the trial plants is carried out after a trial period of 3 weeks by comparison with untreated controls (herbicidal effect in percent: 100% effect=plants have died, 0% effect=like control plants).

In addition to the aforementioned compounds, the following compounds at 320 g/ha a.i. show a pre-emergence effect of ≧80% against *Lolium multiflorum* and *Setaria viridis*: I-a-2, I-a-3, I-a-4, I-a-5, I-a-6, I-a-16, I-a-19, I-b-1, I-b-2, I-b-3, I-b-5, I-b-6, I-b-7, I-b-8, I-b-22, I-c-2, I-c-3, I-c-4, I-c-5, I-c-6, I-c-7, I-c-21.

2. Post-Emergence Herbicidal Effect

Seeds of monocotyledonous and dicotyledonous weed plants and crop plants are placed in sandy loam soil in wood fibre pots and are covered with earth and cultivated in a greenhouse under good growth conditions. 2-3 weeks after sowing, the trial plants are treated at the one-leaf stage. The test compounds, formulated as wettable powders (WP), are sprayed onto the green parts of the plants, at various dosages, with a water application rate of 600 l/ha (converted) and with addition of 0.2% wetting agent. After the trial plants have stood in the greenhouse for about 3 weeks under optimum growth conditions, the effect of the products is rated visually in comparison to untreated controls (herbicidal effect in percent: 100% effect=plants have died, 0% effect=like control plants).

As well as the aforementioned compounds, the following compounds show a post-emergence effect of ≧80% at 320 g/ha a.i. against *Echinocloa crus-galli*, *Lolium multiflorum* and *Setaria viridis*: I-a-1, I-a-2, I-a-3, I-a-4, I-a-5, I-b-1, I-b-2, I-b-3, I-c-2.

As well as the aforementioned compounds, the following compounds show a post-emergence effect of ≧80% at 80 g/ha against *Echinocloa crus-galli* and *Setaria viridis*: I-a-6, I-a-7, I-a-19, I-a-24, I-b-7, I-b-22, I-c-5, I-c-20.

Example No. 9

1. Post-Emergence Herbicidal Effect

Seeds of monocotyledonous and dicotyledonous weed plants and crop plants are placed in sandy loam soil in wood fibre pots or in plastic pots and are covered with earth and cultivated in a greenhouse and also, during the vegetation period, outdoors, outside of the greenhouse, under good growth conditions. 2 to 3 weeks after sowing, the trial plants are treated at the one- to three-leaf stage. The test compounds, formulated as wettable powders (WP) or liquids (EC), are sprayed onto the plants and the soil surface in various dosages, with a water application rate of 300 l/ha (converted) and with addition of wetting agent (0.2% to 0.3%). 3 to 4 weeks after the trial plants have been treated, the effect of the products is rated visually in comparison to untreated controls (herbicidal effect in percent: 100% effect=plants have died, 0% effect=like control plants).

Use of Safeners:

If the testing is also to look at whether safeners can improve the tolerance of the crop plants for test substances, the following options are used for the application of the safener:

seeds of the crop plants are dressed with the safener substance prior to sowing (the amount of safener is stated as a percentage, based on the seed weight)

crop plants are sprayed with the safener, with a defined application rate per hectare, prior to application of the test substances (typically 1 day before the test substances are applied)

the safener is applied together with the test substance in the form of a tank mix (the amount of safener is reported in g/ha or as a proportion relative to the herbicide).

2. Pre-Emergence Herbicidal Effect

Seeds of monocotyledonous and dicotyledonous weed plants and crop plants are placed in sandy loam soil in wood fibre pots or in plastic pots and are covered with earth. The test compounds, formulated as wettable powders (WP) or liquids (EC), are sprayed onto the soil surface in various dosages, with a water application rate of 300 l/ha (converted). The pots are then placed in a greenhouse under good growth conditions, and also, during the vegetation period, are placed outdoors, outside of the greenhouse, so that the plants are able to germinate and develop. 3 to 4 weeks after the trial plants have been treated, the effect of the products is rated visually in comparison to untreated controls (herbicidal effect in percent: 100% effect=plants have died, 0% effect=like control plants).
Use of Safeners:
If the testing is also to look at whether safeners can improve the tolerance of the crop plants for test substances, the following options are used for the application of the safener:
  seeds of the crop plants are dressed with the safener substance prior to sowing (the amount of safener is stated as a percentage, based on the seed weight)
  pots containing the crop plants are sprayed with the safener, with a defined application rate per hectare, prior to application of the test substances
  the safener is applied together with the test substance in the form of a tank mix (the amount of safener is reported in g/ha or as a proportion relative to the herbicide).
By comparing the effect of test substances on crop plants which have been treated with safener and without safener it is possible to assess the effect of the safener substance.

Greenhouse Container Trials with Cereals

Mefenpyr 1 Day Prior to Herbicide Application

Post-Emergence

|  | | 10 days after application | |
| --- | --- | --- | --- |
|  | Application rate g a.i./ha | Spring barley observed (%) | Spring wheat observed (%) |
| Ex. I-b-5 | 100 | 65 | 15 |
|  | 50 | 50 | 10 |
| Ex. I-b-5 + mefenpyr | 100 + 100 | 50 | 8 |
|  | 50 + 100 | 20 | 5 |

|  | Application rate g a.i./ha | 28 days after application Spring barley observed (%) |
| --- | --- | --- |
| Ex. I-b-5 | 100 | 30 |
|  | 25 | 10 |
| Ex. I-b-5 + mefenpyr | 100 + 100 | 15 |
|  | 50 + 100 | 5 |

Greenhouse Container Trials with Maize

Ex. II-e-5 1 Day Prior to Herbicide Application

Pre-Emergence

|  | Application rate g a.i./ha | 28 days after application Maize - Arsenal observed (%) |
| --- | --- | --- |
| Ex. I-c-1 | 50 | 55 |
| Ex. I-c-1 + Ex. II-e-5 | 100 + 100 | 20 |

|  | Application rate g a.i./ha | 28 days after application Maize - Arsenal observed (%) |
| --- | --- | --- |
| Ex. I-b-2 | 50 | 50 |
|  | 25 | 40 |
| Ex. I-b-2 + Ex. II-e-5 | 50 + 200 | 25 |
|  | 25 + 200 | 20 |

Example 10

Boosting of Penetration into the Plant by Ammonium Salts or Phosphonium Salts, and Synergistic Boosting of Penetration into the Plant by Ammonium/Phosphonium Salts in Combination with Penetration Promoters This test measures the penetration of active compounds through enzymatically isolated cuticles of apple leaves.
The leaves used were cut in the fully developed state from apple trees of the Golden Delicious variety. The cuticles were isolated as follows:
  first of all, leaf discs labelled on the underside with dye and formed by punching were filled by means of vacuum infiltration with a pectinase solution (0.2% to 2% strength) buffered to a pH of between 3 and 4,
  the sodium azide was then added and
  the leaf discs thus treated were left to stand until the original leaf structure broke down and the non-cellular cuticle underwent detachment.
After that, only those cuticles from the top leaf sides that were free from stomata and hairs were used. They were washed a number of times in alternation with water and with a buffer solution, pH 7. The clean cuticles obtained were, finally, applied to Teflon plaques, smoothed with a gentle jet of air, and dried.
In the next step the cuticular membranes obtained in this way were placed in stainless steel diffusion cells (transport chambers) for the purpose of membrane transport investigations. For these investigations the cuticles were placed centrally using tweezers on the edges of the diffusion cells, which were coated with silicone grease, and sealed with a ring, which was likewise greased. The arrangement had been chosen so that the morphological outer side of the cuticles was directed outwards, in other words facing the air, while the original inner side was facing the inside of the diffusion cell.
The diffusion cells were filled with a 30% strength ethylene glycol/water solution. Penetration was determined by applying 10 µl of the spray liquor of the composition below to the outer side of each of the cuticles. The spray liquor is prepared using local mains water of medium hardness.

After the spray liquors had been applied, the water was evaporated and then the chambers were inverted and placed in thermostated troughs, in which the temperature and humidity over the cuticles was adjustable by means of a gentle stream of air onto the cuticles, with the spray coating (20° C., 60% rh). At regular intervals, samples were taken using an autosampler, and the amount of active compound was determined using HPLC.

The results of the experiment are apparent from the table below. The numbers stated represent average values from 5 to 6 measurements. It can clearly be seen that ammonium sulphate, even on its own, significantly improves the penetration, and that together with RME there is a superadditive (synergistic) effect.

| Active compound | | Penetration after 24 h/% | | | |
|---|---|---|---|---|---|
| | EC | EC + AS (1 g/l) | EC + RME (1 g/l) | EC + RME (1 g/l) + AS (1 g/l) | EC + RME (1 g/l) + ADHP (1 g/l) |
| Example I-a-7 0.2 g/l in water/acetone 6:4 | 1.7 | 7.1 | 7.1 | 29.6 | 22.3 |

RME = Rapeseed oil methyl ester (formulated for use as 500 EW, concentration figure in g active compound/l)
AS = ammonium sulphate
ADHP = ammonium dihydrogen phosphate
EC = emulsifiable concentrate Example 11

Activity Boost Through Ammonium/Phosphonium Salts in Combination with Penetration Promoters

*Myzus persicae* Test

| Solvent: | 7 parts by weight of dimethylformamide |
|---|---|
| Emulsifier: | 2 parts by weight of alkylaryl polyglycol ether |

A suitable preparation of active compound is prepared by mixing 1 part by weight of active compound with the stated amounts of solvent and emulsifier and diluting the concentrate with water to the desired concentration. For application with ammonium salts or phosphonium salts and penetration promoters (rapeseed oil methyl ester 500 EW) these are in each case added in a concentration of 1000 ppm to the spray liquor.

Bell pepper plants (*Capsicum annuum*) heavily infested by the green peach aphid (*Myzus persicae*) are sprayed to runoff with the preparation of active compound at the desired concentration.

After the desired time the destruction in % is determined. 100% means that all of the animals have been killed; 0% means that no animals have been killed.

TABLE

| Active compound | Concentration (ppm) | Destruction (%) after 6 d | +AS 1000 ppm | +RME 1000 pm | +AS +RME 1000 ppm each |
|---|---|---|---|---|---|
| I-a-1 | 20 | 0 | 65 | 98 | 99 |
| | 4 | 0 | 0 | 35 | 75 |

TABLE-continued

| Active compound | Concentration (ppm) | Destruction (%) after 6 d | +AS 1000 ppm | +RME 1000 pm | +AS +RME 1000 ppm each |
|---|---|---|---|---|---|
| I-a-12 | 100 | 85 | 98 | 99 | 99 |
| | 20 | 10 | 0 | 45 | 99 |

Example 12

*Aphis gossypii* Test

| Solvent: | 7 parts by weight of dimethylformamide |
|---|---|
| Emulsifier: | 2 parts by weight of alkylaryl polyglycol ether |

A suitable preparation of active compound is prepared by mixing 1 part by weight of active compound with the stated amounts of solvent and emulsifier and diluting the concentrate with emulsifier-containing water to the desired concentration. For application with ammonium salts or phosphonium salts and penetration promoters (rapeseed oil methyl ester 500 EW) these are in each case added in a concentration of 1000 ppm a.i. to the spray liquor.

Cotton plants (*Gossypium hirsutum*) heavily infested by the cotton aphid (*Aphis gossypii*) are sprayed to runoff with the preparation of active compound at the desired concentration.

After the desired time the destruction in % is determined. 100% means that all of the aphids have been killed; 0% means that no aphids have been killed.

TABLE

| Active compound | Concentration (ppm) | Destruction (%) after 6 d | +AS 1000 ppm | +RME 1000 pm | +AS +RME 1000 ppm each |
|---|---|---|---|---|---|
| I-a-1 | 100 | 60 | 90 | 90 | 90 |
| | 20 | 5 | 20 | 5 | 85 |
| I-a-7 | 20 | 5 | 10 | 70 | 90 |

Example No. 13

Critical Concentration Test/Soil Insects—Treatment of Transgenic Plants

| Test insect: | *Diabrotica balteata* - larvae in the soil |
|---|---|
| Solvent: | 7 parts by weight of acetone |
| Emulsifier: | 1 part by weight of alkylaryl polyglycol ether |

A suitable preparation of active compound is prepared by mixing 1 part by weight of active compound with the stated amount of solvent, adding the stated amount of emulsifier and diluting the concentrate with water to the desired concentration.

The preparation of active compound is poured onto the soil. The concentration of the active compound in the preparation is almost irrelevant here, the only critical factor being the amount by weight of active compound per unit volume of soil, which is stated in ppm (mg/l). The soil is placed in 0.25 l pots which are left to stand at 20° C.

Immediately after sample preparation, 5 pregerminated maize corns of the cultivar YIELD GUARD (trade mark of Monsanto Comp., USA) are placed in each pot. After 2 days the corresponding test insects are placed into the treated soil. After a further 7 days the efficacy of the active compound is determined by counting of the maize plants that have emerged (1 plant=20% effect).

Example No. 14

*Heliothis virescens* Test—Treatment of Transgenic Plants

| Solvent: | 7 parts by weight of acetone |
| Emulsifier: | 1 part by weight of alkylaryl polyglycol ether |

A suitable preparation of active compound is prepared by mixing 1 part by weight of active compound with the stated amount of solvent and the stated amount of emulsifier and diluting the concentrate with water to the desired concentration.

Soybean shoots (*Glycine max*) of the cultivar Roundup Ready (trade mark of Monsanto Comp., USA) are treated by being immersed into the preparation of active compound at the desired concentration and are populated with the tobacco budworm *Heliothis virescens* while the leaves are still moist.

After the desired time, the destruction of the insects is determined.

The invention claimed is:
1. A compound of the formula (I),

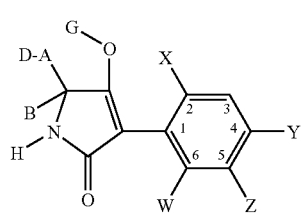

in which
W represents hydrogen, alkyl, alkenyl, alkynyl, halogen, alkoxy, alkenyloxy, haloalkyl, haloalkoxy or cyano,
X represents halogen, alkyl, alkenyl, alkynyl, alkoxy, alkenyloxy, alkylthio, alkylsulphinyl, alkylsulphonyl, haloalkyl, haloalkoxy, haloalkenyloxy, nitro or cyano,
Y and Z independently of one another represent hydrogen, alkyl, alkenyl, alkynyl, alkoxy, halogen, haloalkyl, haloalkoxy, cyano, nitro, optionally substituted aryl or optionally substituted heteroaryl, with the proviso that one of the radicals, Y or Z, represents optionally substituted aryl or optionally substituted heteroaryl,
A represents a $C_1$-$C_6$-alkanediyl radical,
B represents hydrogen, alkyl or alkoxyalkyl,
D represents in each case optionally substituted alkoxy, alkenyloxy, alkynyloxy, alkoxyalkoxy, phenoxy, heteroaryloxy, phenylalkoxy, or heteroarylalkoxy, or represents optionally substituted, saturated or unsaturated cycloalkyl interrupted by one or optionally two oxygen atoms, or A represents a bond,
B represents hydrogen or alkyl,
D represents optionally substituted, saturated or unsaturated $C_5$-$C_6$-cycloalkyl interrupted by oxygen,
G represents hydrogen (a),

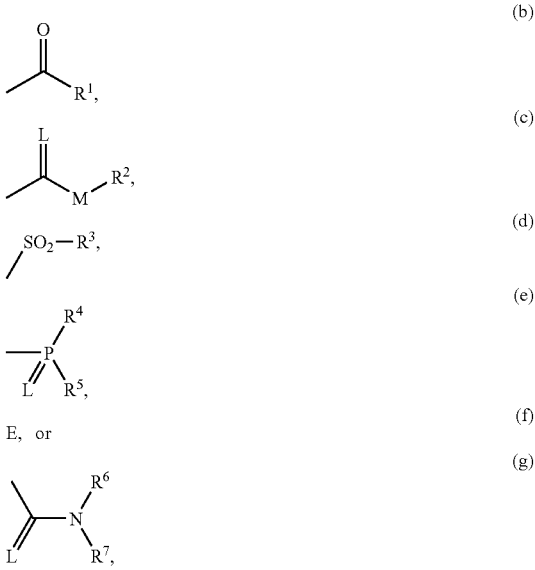

in which
E represents a metal ion or an ammonium ion,
L represents oxygen or sulphur,
M represents oxygen or sulphur,
$R^1$ represents in each case optionally halogen- or cyano-substituted alkyl, alkenyl, alkoxyalkyl, alkylthioalkyl or polyalkoxyalkyl, represents in each case optionally halogen-, alkyl- or alkoxy-substituted cycloalkyl or heterocyclyl, or represents in each case optionally substituted phenyl, phenylalkyl, heteroaryl, phenoxyalkyl or heteroaryloxyalkyl,
$R^2$ represents in each case optionally halogen- or cyano-substituted alkyl, alkenyl, alkoxyalkyl or polyalkoxyalkyl, or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio, or represent in each case optionally substituted phenyl, benzyl, phenoxy or phenylthio,
$R^6$ and $R^7$ independently of one another represent hydrogen, in each case optionally halogen- or cyano-substituted alkyl, cycloalkyl, alkenyl, alkoxy, or alkoxyalkyl, or represent in each case optionally substituted phenyl or benzyl, or $R^6$ and $R^7$ together with the nitrogen atom to which they are attached, form a ring system which optionally contains oxygen or sulphur and is optionally substituted.

2. The compound according to claim 1, in which

W represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkyl, $C_1$-$C_4$-haloalkoxy or cyano, X represents halogen, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro or cyano, Y and Z independently of one another represent hydrogen, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, cyano, $C_2$-$C_6$-alkenyl, $C_2$-$C_6$-alkynyl or an aryl or a heteroaryl radical selected from the group consisting of

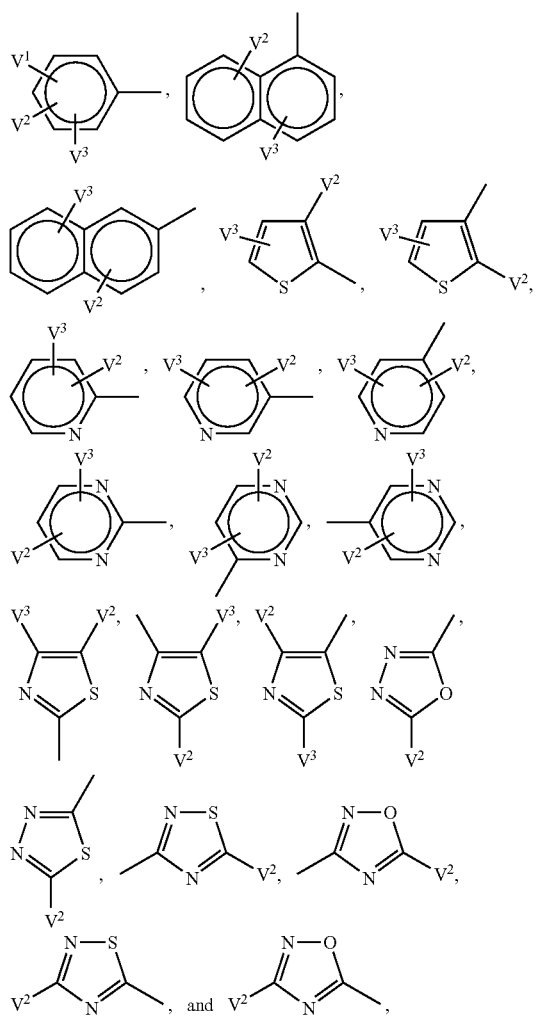

$V^1$ represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, or cyano, or phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally substituted with one or more substituents selected from the group consisting of halogen, $C_1$-$C_6$-alkyl, $C_1$-$C_6$-alkoxy, $C_1$-$C_4$-haloalkyl, $C_1$-$C_4$-haloalkoxy, nitro and cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, with the proviso that one of the radicals, Y or Z, represents one of the aryl or heteroaryl radicals defined above, A represents a $C_1$-$C_6$-alkanediyl radical, B represents hydrogen, $C_1$-$C_6$-alkyl or $C_1$-$C_4$-alkoxy-$C_1$-$C_4$-alkyl, D represents $C_1$-$C_6$-alkoxy, $C_3$-$C_6$-alkenyloxy, $C_3$-$C_6$-alkynyloxy, or $C_1$-$C_4$-alkoxy-$C_2$-$C_4$-alkoxy, each of which is optionally substituted with one or more substituents selected from the group consisting of halogen and cyano, or represents phenoxy, pyridyloxy, pyrimidyloxy, pyrazolyloxy, thiazolyloxy, thienyloxy, phenyl-$C_1$-$C_4$-alkoxy, pyridyl-$C_1$-$C_4$-alkoxy, pyrimidyl-$C_1$-$C_4$-alkoxy, pyrazolyl-$C_1$-$C_4$-alkoxy, or thienyl-$C_1$-$C_4$-alkoxy, each of which is optionally substituted with one, two or three substituents selected from the group consisting of halogen, $C_1$-$C_6$-alkyl, $C_1$-$C_6$-alkoxy, $C_1$-$C_4$-haloalkyl, $C_1$-$C_4$-haloalkoxy, cyano and nitro, or represents saturated or unsaturated $C_3$-$C_8$-cycloalkyl interrupted by one or, optionally, two oxygen atoms, optionally substituted with one, two or three substituents selected from the group consisting of halogen, $C_1$-$C_4$-alkyl, $C_1$-$C_4$-alkoxy and $C_1$-$C_4$-haloalkyl, or A represents a bond, B represents hydrogen or $C_1$-$C_4$-alkyl, D represents, saturated or unsaturated $C_3$-$C_8$-cycloalkyl interrupted by one or, optionally, two oxygen atoms optionally substituted with one, two or three substituents selected from the group consisting of $C_1$-$C_2$-alkyl and $C_1$-$C_2$-alkoxy, G represents hydrogen (a),

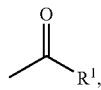 (b)

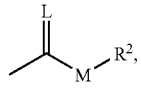 (c)

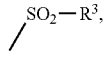 (d)

 (e)

E, or (f)

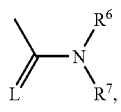 (g)

in which

E represents a metal ion or an ammonium ion,

L represents oxygen or sulphur and

M represents oxygen or sulphur,

R¹ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl, represents optionally halogen-, $C_1$-$C_6$-alkyl- or $C_1$-$C_6$-alkoxy-substituted $C_3$-$C_8$-cycloalkyl, in which optionally one or two methylene groups not directly adjacent are replaced by oxygen, sulphur, or combinations thereof,
represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkyl sulphonyl-substituted phenyl,
represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl,
represents optionally halogen- or $C_1$-$C_6$-alkyl-substituted 5- or 6-membered heteroaryl having one or two heteroatoms selected from the group consisting of oxygen, sulphur and nitrogen,
represents optionally halogen- or $C_1$-$C_6$-alkyl-substituted phenoxy-$C_1$-$C_6$-alkyl, or
represents optionally halogen-, amino- or $C_1$-$C_6$-alkyl-substituted 5- or 6-membered heteroaryloxy-$C_1$-$C_6$-alkyl having one or two heteroatoms selected from the group consisting of oxygen, sulphur and nitrogen, R² represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl,
represents optionally halogen-, $C_1$-$C_6$-alkyl- or $C_1$-$C_6$-alkoxy-substituted $C_3$-$C_8$-cycloalkyl, or
represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, R³ represents optionally halogen-substituted $C_1$-$C_8$-alkyl, or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, R⁴ and R⁵ independently of one another represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio, or
represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, R⁶ and R⁷ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl,
represent in each case optionally halogen-, $C_1$-$C_8$-alkyl-, $C_1$-$C_8$-haloalkyl- or $C_1$-$C_8$-alkoxy-substituted phenyl or benzyl, or R⁶ and R⁷ together represent an optionally $C_1$-$C_6$-alkyl-substituted $C_3$-$C_6$-alkylene radical in which optionally a methylene group is replaced by oxygen or sulphur.

3. The compound according to claim 1, in which
W represents hydrogen, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy,
X represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-haloalkyl, $C_1$-$C_4$-haloalkoxy or cyano,
Y and Z independently of one another represent hydrogen, fluorine, chlorine, bromine, $C_1$-$C_4$-alkyl, $C_2$-$C_4$-alkenyl, $C_2$-$C_4$-alkynyl, $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or an aryl or a heteroaryl radical selected from the group consisting of

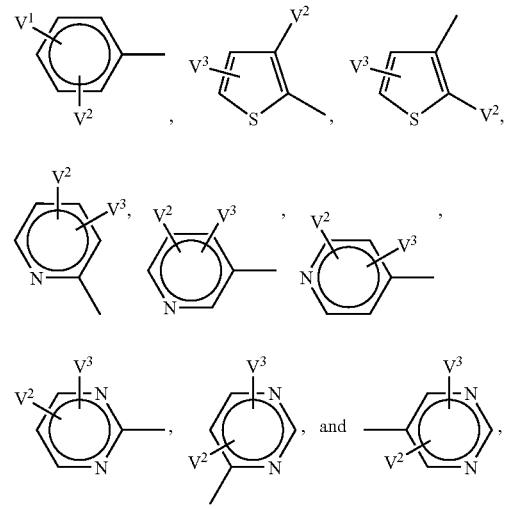

V¹ represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, or cyano, or phenyl optionally substituted with one or two substituents selected from the group consisting of fluorine, chlorine bromine, $C_1$-$C_4$-alkyl, $C_1$-$C_4$-alkoxy, $C_1$-$C_2$-haloalkyl, $C_1$-$C_2$-haloalkoxy, nitro and cyano, V² and V³ independently of one another represent hydrogen, fluorine, chlorine, bromine, $C_1$-$C_4$-alky $C_1$-$C_4$-alkoxy, $C_1$-$C_2$-haloalkyl or $C_1$-$C_2$-haloalkoxy, with the proviso that one of the radicals, Y or Z, represents one of the aryl or heteroaryl radicals defined above, A represents a $C_1$-$C_4$-alkanediyl radical, B represents hydrogen, $C_1$-$C_4$-alkyl or $C_1$-$C_4$-alkoxy-$C_1$-$C_2$-alkyl, D represents $C_1$-$C_4$-alkoxy, $C_3$-$C_6$-alkenyloxy, $C_3$-$C_6$-alkynyloxy, $C_1$-$C_3$-alkoxy-$C_2$-$C_3$-alkoxy, each of which is optionally substituted with one, two, three, four or five substituents selected from the group consisting of fluorine, chlorine and cyano, represents phenoxy optionally substituted with one or two substituents selected from the group consisting of fluorine, chlorine, bromine, $C_1$-$C_4$-alkyl, $C_1$-$C_4$-alkoxy, trifluoromethyl and trifluoromethoxy, or represents saturated $C_4$-$C_7$-cycloalkyl interrupted by one or, optionally, two oxygen atoms and optionally substituted with one or two substituents selected from the group consisting of fluorine, chlorine, methyl, ethyl, methoxy and trifluoromethyl, or A represents a bond, B represents hydrogen or $C_1$-$C_2$-alkyl, D represents saturated $C_5$-$C_6$-cycloalkyl interrupted by one or, optionally, two oxygen atoms, and optionally substituted with one or two substituents selected from the group consisting of methyl and ethyl, G represents hydrogen (a),

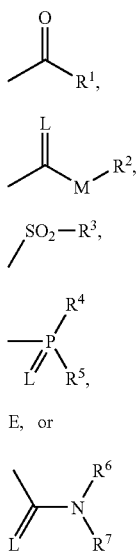

in which
E represents a metal ion or an ammonium ion,
L represents oxygen or sulphur and
M represents oxygen or sulphur,
$R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally substituted with one, two or three substituents selected from the group consisting of fluorine and chlorine, or represents $C_3$-$C_7$-cycloalkyl in which optionally one or two methylene groups not directly adjacent are replaced by oxygen, sulphur, or combinations thereof, and wherein said $C_3$-$C_7$-cycloalkyl is optionally substituted with one or two substituents selected from the group consisting of fluorine, chlorine, $C_1$-$C_5$-alkyl and $C_1$-$C_5$-alkoxy,
represents phenyl optionally substituted with one, two or three substituents selected from the group consisting of fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio and $C_1$-$C_4$-alkylsulphonyl,
represents phenyl-$C_1$-$C_4$-alkyl optionally substituted with one or two substituents selected from the group consisting of fluorine, chlorine, bromine, $C_1$-$C_4$-alkyl, $C_1$-$C_4$-alkoxy, $C_1$-$C_3$-haloalkyl, and $C_1$-$C_3$-haloalkoxy,
represents pyrazolyl, thiazolyl, pyridyl, pyrimidyl, furanyl or thienyl, each of which is optionally substituted with one or two substituents selected from the group consisting of fluorine, chlorine, bromine and $C_1$-$C_4$-alkyl, represents phenoxy-$C_1$-$C_5$-alkyl optionally substituted with one or two substituents selected from the group consisting of fluorine, chlorine, bromine and $C_1$-$C_4$-alkyl, or
represents pyridyloxy-$C_1$-$C_5$-alkyl, pyrimidyloxy-$C_1$-$C_5$-alkyl or thiazolyloxy-$C_1$-$C_5$-alkyl, each of which is optionally substituted with one or two substituents selected from the group consisting of fluorine, chlorine, bromine, amino and $C_1$-$C_4$-alkyl,
$R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally substituted with one, two or three substituents selected from the group consisting of fluorine and chlorine,
represents $C_3$-$C_7$-cycloalkyl optionally substituted with one or two substituents selected from the group consisting of fluorine, chlorine, bromine, $C_1$-$C_4$-alkyl and $C_1$-$C_4$-alkoxy, or
represents phenyl or benzyl, each of which is optionally substituted with one, two or three substituents selected from the group consisting of fluorine, chlorine, bromine, cyano, nitro, $C_1$-$C_4$-alkyl, $C_1$-$C_3$-alkoxy, $C_1$-$C_3$-haloalkyl and $C_1$-$C_3$-haloalkoxy,
$R^3$ represents $C_1$-$C_6$-alkyl optionally substituted with one, two or three substituents selected from the group consisting of fluorine and chlorine, or phenyl or benzyl, each of which is optionally substituted with one or two substituents selected from the group consisting of fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano and nitro,
$R^4$ and $R^5$ independently of one another represent $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio, each of which is optionally substituted with one, two or three substituents selected from the group consisting of fluorine and chlorine, or
represents phenyl, phenoxy or phenylthio, each of which is optionally substituted with one or two substituents selected from the group consisting of fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl and $C_1$-$C_3$-haloalkyl,
$R^6$ and $R^7$ independently of one another represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally substituted with one, two or three substituents selected from the group consisting of fluorine and chlorine, or represent phenyl or benzyl, each of which is optionally substituted with one, two or three substituents selected from the group consisting of fluorine, chlorine, bromine, $C_1$-$C_5$-haloalkyl, $C_1$-$C_5$-alkyl and $C_1$-$C_5$-alkoxy, or $R^6$ and $R^7$ together represent an optionally $C_1$-$C_4$-alkyl-substituted $C_3$-$C_6$-alkylene radical in which optionally a methylene group is replaced by oxygen or sulphur.

4. The compound according to claim 1, in which
W represents hydrogen, chlorine, bromine, methyl, ethyl, methoxy, ethoxy or trifluoromethyl,
X represents chlorine, bromine, methyl, ethyl, propyl, methoxy, ethoxy, trifluoromethyl, difluoromethoxy, trifluoromethoxy or cyano,
Y and Z independently of one another represent hydrogen, fluorine, chlorine, bromine, methyl, ethyl, methoxy, trifluoromethyl, trifluoromethoxy, cyano or a phenyl radical

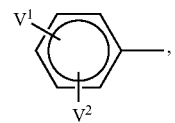

$V^1$ represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ represents hydrogen, fluorine, chlorine, methyl, ethyl, n-propyl, isopropyl, methoxy, ethoxy or trifluoromethyl, with the proviso that one of the radicals, Y or Z, represents an optionally substituted phenyl radical, A represents —$CH_2$—, —$CH_2$—$CH_2$—, —$CH_2$—$CH_2$—$CH_2$—, —$CH_2$—$CHCH_3$—, —$CHCH_3$—$CH_2$—, —$CH_2$—$C(CH_3)_2$—, or —$C(CH_3)_2$—$CH_2$—, B represents hydrogen, methyl or ethyl, D represents methoxy, ethoxy, propoxy, isopropoxy, butoxy, isobutoxy, allyloxy, methallyloxy, isoprenyloxy, propargyloxy, butenyloxy, methoxyethoxy, or ethoxyethoxy, represents phenoxy optionally monosubstituted by fluorine, chlorine, bromine, methyl, methoxy, trifluoromethyl or trifluoromethoxy, or represents in each case optionally mono- to di-methyl-substituted tetrahydrofuranyl, tetrahydropyranyl, dioxolanyl or dioxanyl, or A represents a bond, B represents hydrogen, methyl or ethyl, D represents tetrahydrofuranyl, tetrahydropyranyl, dioxolanyl or dioxanyl, G represents hydrogen (a),

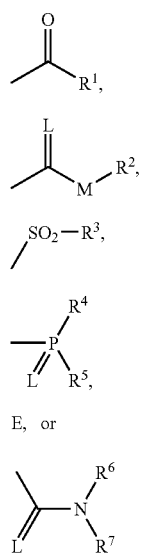

in which

E represents a metal ion or an ammonium ion,

L represents oxygen or sulphur,

M represents oxygen or sulphur, $R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally substituted with one, two or three substituents selected from the group consisting of fluorine and chlorine, or represents $C_3$-$C_6$-cycloalkyl optionally monosubstituted by fluorine, chlorine, methyl, ethyl or methoxy, represents phenyl optionally substituted with one or two substituents selected from the group consisting of fluorine, chlorine, bromine, cyano, nitro, methyl, ethyl, n-propyl, isopropyl, methoxy, ethoxy, trifluoromethoxy and trifluoromethyl, or represents furanyl, thienyl or pyridyl, each of which is optionally monosubstituted by chlorine, bromine or methyl, $R^2$ represents $C_1$-$C_{10}$-alkyl, $C_2$-$C_{10}$-alkenyl or $C_1$-$C_4$-alkoxy-$C_2$-$C_4$-alkyl, each of which is optionally substituted with one, two or three substituents selected from the group consisting of fluorine and chlorine, represents cyclopentyl or cyclohexyl, or represents phenyl or benzyl, each of which is optionally substituted with one or two substituents selected from the group consisting of fluorine, chlorine, cyano, nitro, methyl, ethyl, methoxy, trifluoromethyl and trifluoromethoxy, $R^3$ represents methyl, ethyl, propyl or isopropyl, each of which is optionally substituted with one, two or three substituents selected from the group consisting of fluorine and chlorine, or phenyl optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkyl-thio, or represent phenyl, phenoxy or phenylthio, in each case optionally monosubstituted by fluorine, chlorine, bromine, nitro, cyano, methyl, methoxy, trifluoromethyl or trifluoromethoxy, $R^6$ and $R^7$ independently of one another represent hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, or phenyl optionally substituted with one or two substituents selected from the group consisting of fluorine, chlorine, bromine, methyl, methoxy and trifluoromethyl, or $R^6$ and $R^7$ together represent a $C_5$-$C_6$-alkylene radical in which optionally a methylene group is replaced by oxygen or sulphur.

5. The compound according to claim 1, in which

W represents hydrogen, methyl or ethyl,

X represents chlorine, methyl or ethyl,

Y and Z independently of one another represent hydrogen or a phenyl radical selected from the group consisting of

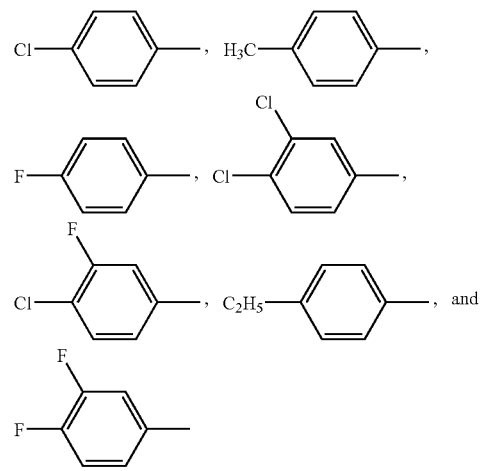

with the proviso that one of the radicals, Y or Z, represents an optionally substituted phenyl radical, A represents —$CH_2$— or —$CH_2$—$CH_2$—, B represents methyl, D represents methoxy or tetrahydrofuranyl, or A represents a bond, B represents methyl or ethyl, D represents tetrahydrofuranyl, G represents hydrogen (a),

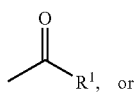
(b)

or

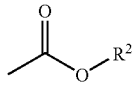
(c)

in which $R^1$ represents $C_1$-$C_{10}$-alkyl, $C_1$-$C_4$-alkoxy-$C_1$-$C_2$-alkyl, or cyclopropyl, or represents phenyl optionally monosubstituted by chlorine, $R^2$ represents $C_1$-$C_{10}$-alkyl or benzyl.

6. A process for preparing a compound of the formula (I) according to claim 1, comprising (A) condensing intramolecularly a compound of the formula (II)

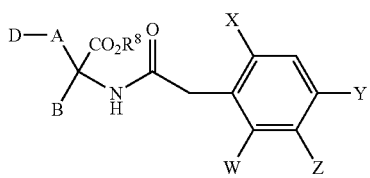
(II)

in which

A, B, D, W, X, Y and Z are as defined in claim 1, and $R^8$ represents alkyl, in the presence of a diluent and in the presence of a base to obtain a compound of the formula (I-a)

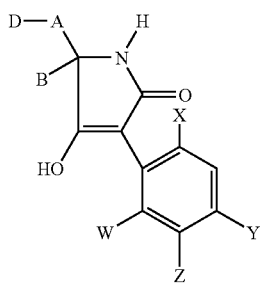
(I-a)

wherein A, B, D, W, X, Y and Z are as defined in claim 1;

(B) reacting a compound of formula (I-a)

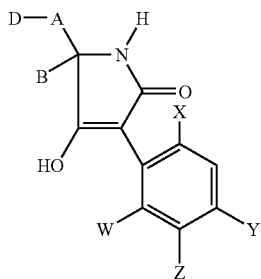
(I-a)

wherein A, B, D, W, X, Y and Z are as defined in claim 1,

α) with a compound of the formula (III)

(III)

in which $R^1$ is as defined in claim 1, and

Hal represents halogen or

β) with a carboxylic anhydride of the formula (IV)

$R^1$—CO—O—CO—$R^1$ (IV)

in which $R^1$ is as defined in claim 1, optionally in the presence of a diluent and optionally in the presence of an acid-binding agent, to obtain a compound of formula (I-b)

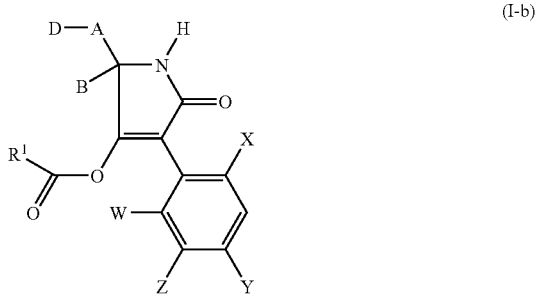
(I-b)

wherein $R^1$, A, B, D, W, X, Y and Z are as defined in claim 1;

(C) reacting a compound of formula (I-a)

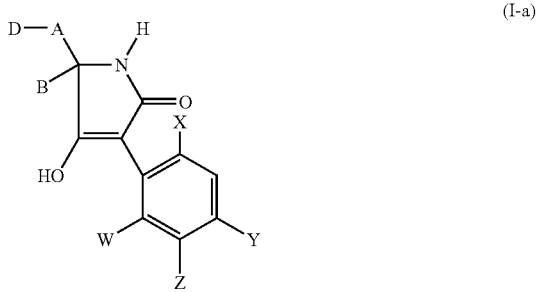
(I-a)

wherein A, B, D, W, X, Y and Z are as defined in claim 1, with a chloroformic ester or a chloroformic thioester of the formula (V)

$R^2$-M-CO—$C_1$ (V)

in which $R^2$ and M are as defined in claim 1, optionally in the presence of a diluent and optionally in the presence of an acid-binding agent, to obtain a compound of formula (I-c)

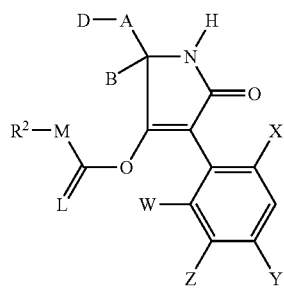
(I-c)

wherein R², A, B, , M, X, Y and Z are as defined in claim 1 and L is oxygen;

(D) reacting a compound of formula (I-a)

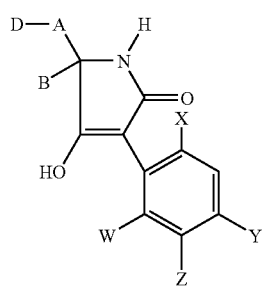
(I-a)

wherein A, B, D, W, X, Y and Z are as defined in claim 1,
with a chloromonothioformic ester or a chlorodithioformic ester of the formula (VI)

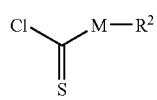
(VI)

in which
M and R² are as defined in claim 1,
optionally in the presence of a diluent and optionally in the presence of an acid-binding agent,
to obtain a compound of formula (I-c)

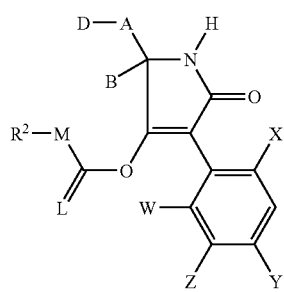
(I-c)

wherein R², A, B, D, W, M, X, Y and Z are as defined in claim 1 and L is sulphur;

(E) reacting a compound of formula (I-a)

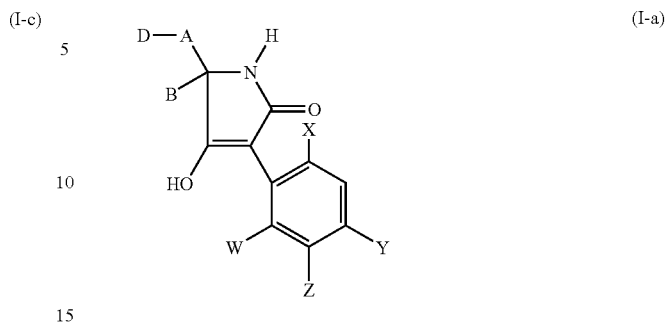
(I-a)

wherein A, B, D, W, X, Y and Z are as defined in claim 1,
with a sulphonyl chloride of the formula (VII)

(VII)

in which
R³ is as defined in claim 1,
optionally in the presence of a diluent and optionally in the presence of an acid-binding agent,
to obtain a compound of formula (I-d)

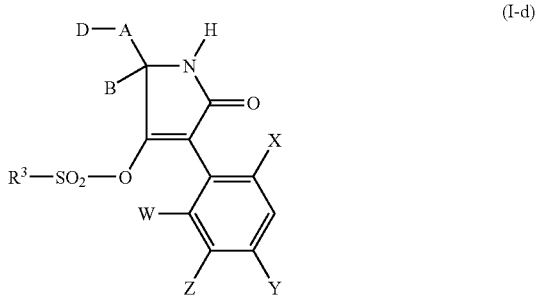
(I-d)

wherein R³, A, B, D, W, X, Y and Z are as defined in claim 1;

(F) reacting a compound of formula (I-a)

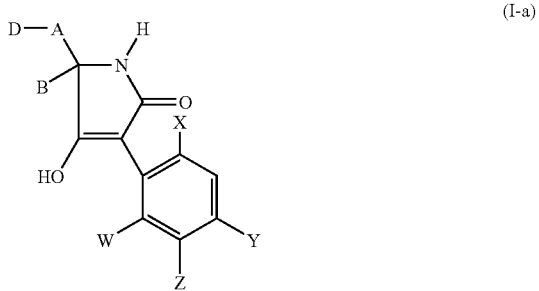
(I-a)

wherein A, B, D, W, X, Y and Z are as defined in claim 1,
with a phosphorus compound of the formula (VIII)

(VIII)

in which
L, R⁴ and R⁵ are as defined in claim 1 and
Hal represents halogen, optionally in the presence of a diluent and optionally in the presence of an acid-binding agent, to obtain a compound of formula (I-e)

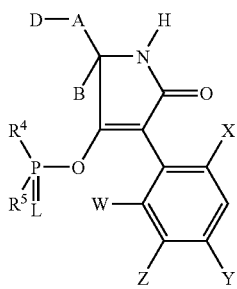
(I-e)

wherein L, $R^4$, $R^5$, A, B, D, W, X, Y and Z are as defined in claim 1;

(G) reacting a compound of formula (I-a)

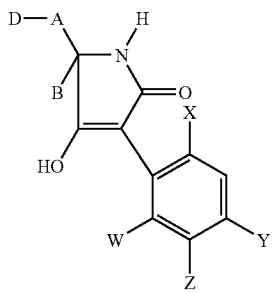
(I-a)

wherein A, B, D, W, X, Y and Z are as defined in claim 1, with a metal compound or an amine of the formulae (IX) or (X)

Me(OR$^{10}$)$_t$ (IX)

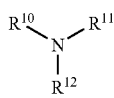
(X)

in which

Me represents a monovalent or divalent metal, t represents the number 1 or 2 and $R^{10}$, $R^{11}$, and $R^{12}$ independently of one another represent hydrogen or alkyl, optionally in the presence of a diluent, to obtain a compound of formula (I-f)

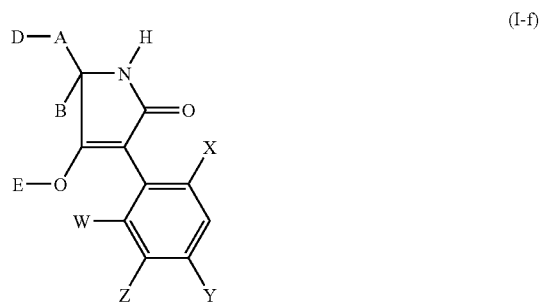
(I-f)

wherein E, A, B, D, W, X, Y and Z are as defined in claim 1;

(H) reacting a compound of formula (I-a)

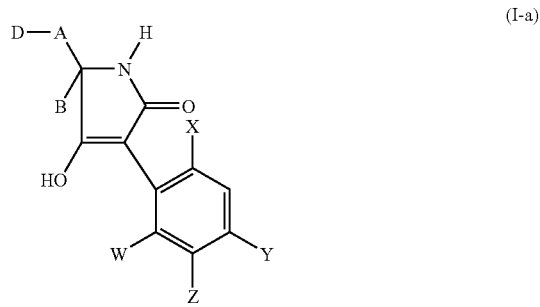
(I-a)

wherein A, B, D, W, X, Y and Z are as defined in claim 1,

α) with an isocyanate or an isothiocyanate of the formula (XI)

$R^6$—N=C=L (XI)

in which $R^6$ and L are as defined in claim 1, optionally in the presence of a diluent and optionally in the presence of a catalyst, or β) with a carbamoyl chloride or a thiocarbamoyl chloride of the formula (XII)

(XII)

in which

L, $R^6$ and $R^7$ are as defined in claim 1, optionally in the presence of a diluent and optionally in the presence of an acid-binding agent, to obtain a compound of formula (I-g)

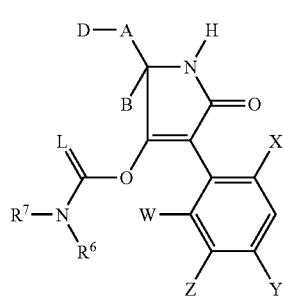
(I-g)

wherein L, R⁶, R⁷, A, B, D, W, X, Y and Z are as defined in claim 1; or (I) coupling a compound of formula (I-a'), (I-b'), (I-c'), (I-d'), (I-e'), (I-f'), or (I-g')

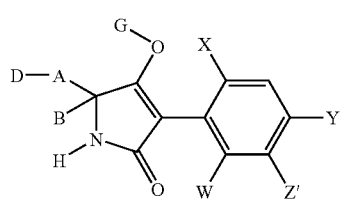
(I-a' to I-g')

wherein A, B, D, G, W, X and Y are as defined in claim 1, and
Z' represents bromine or iodine,
or
coupling a compound of formula (I-a''), (I-b''), (I-c''), (I-d''), (I-e''), (I-f''), or (I-g'')

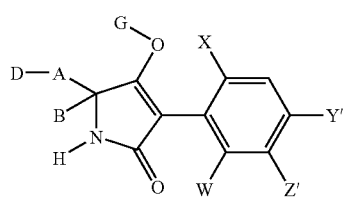
(I-a'' to I-g'')

wherein A, B, D, G, W, X and Z are as defined in claim 1, and
Y' represents bromine or iodine,
with a compound of the formulae (XIXα) or (XIXβ)

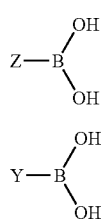
(XIXα)

(XIXβ)

wherein Z and Y are as defined in claim 1,
or an ester thereof, in the presence of a solvent, in the presence of a catalyst and in the presence of a base, to obtain a compound of the formulae (I-a) to (I-g):

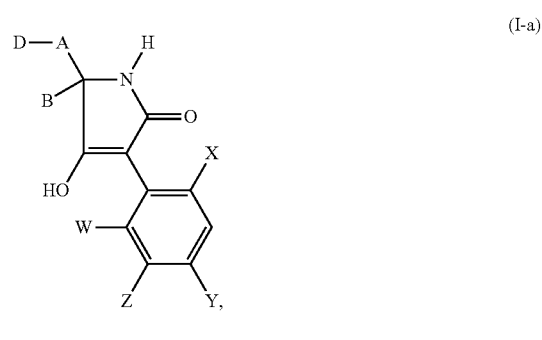
(I-a)

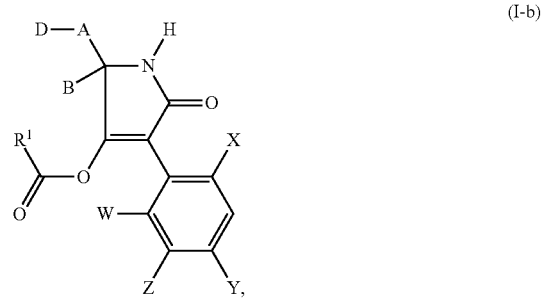
(I-b)

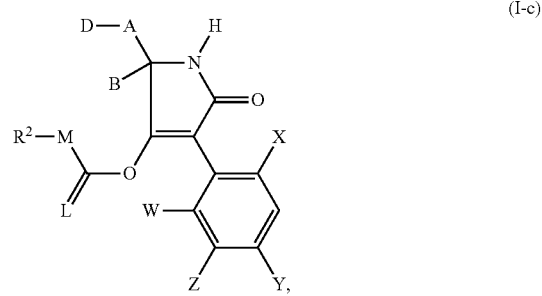
(I-c)

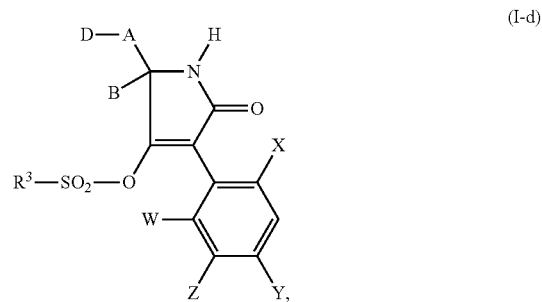
(I-d)

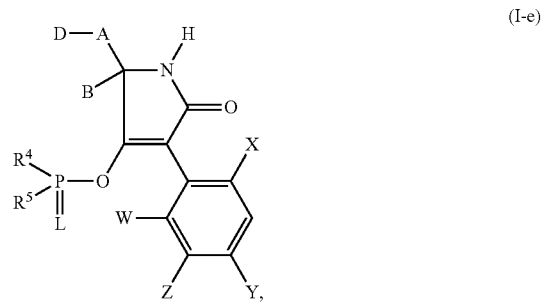
(I-e)

-continued

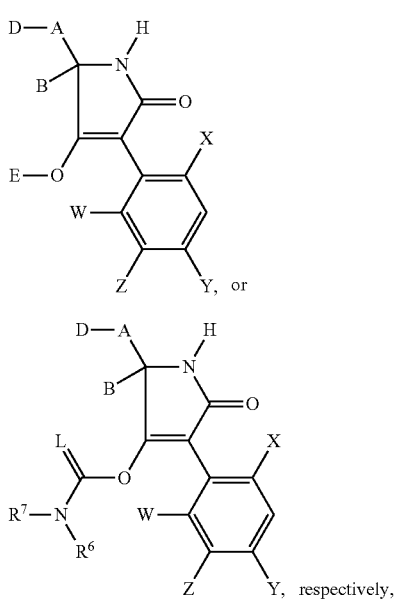

wherein
A, B, D, E, L, M, W, X, Y, Z, $R^1$, $R^2$, $R^3$, $R^4$, $R^5$, $R^6$ and $R^7$ are as defined in claim 1.

7. A pesticide or a herbicide, comprising at least one compound of the formula (I) according to claim 1.

8. A method of controlling animal pests or unwanted vegetation, comprising contacting a compound of the formula (I) according to claim 1 with pests or unwanted vegetation, or their habitat.

9. A process for producing a pesticide or a herbicide, comprising mixing a compound of the formula (I) according to claim 1 with one or more extenders, surface-active substances, or combinations thereof.

10. A method of controlling unwanted plant growth, comprising contacting unwanted vegetation or their habitat with a composition comprising an effective amount of an active-compound combination comprising,
(a') at least one compound according to claim 1 and
(b') at least one crop plant tolerance promoter compound selected from the group consisting of:
4-dichloroacetyl-1-oxa-4-azaspiro[4.5]decane (AD-67, MON-4660), 1-dichloroacetyl-hexahydro-3,3,8a-trimethylpyrrolo[1,2-a]pyrimidin-6(2H)one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)-phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenyl-amino)ethyl)-N-(2-propenyl)acetamide (DKA-24), 2,2-dichloro-N, N-di-2-propenyl-acetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl-1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)-butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloro-quinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoyl-sulphamoyl)-phenyl]-3-methylurea (also known as N-(2-methoxybenzoyl)-4-[(methylaminocarbonyl)-amino]-benzene-sulphonamide), 1-[4-(N-2-methoxybenzoylsulphamoyl)-phenyl]-3,3-dimethylurea, 1-[4-(N-4,5-dimethylbenzoyl-sulphamoyl)-phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzene-sulphonamide, a compound of the general formula (IIa)

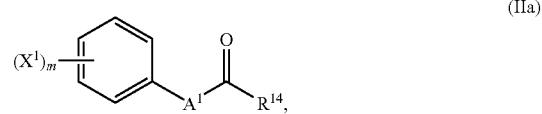

a compound of the general formula (IIb)

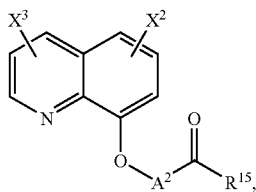

and
a compound of the formula (IIc)

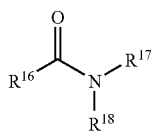

where
m represents a number 0, 1, 2, 3, 4 or 5,
$A^1$ represents one of the following divalent heterocyclic groups

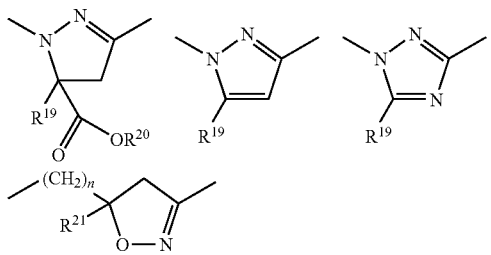

n represents a number 0, 1, 2, 3, 4 or 5,
$A^2$ represents alkanediyl having 1 or 2 carbon atoms optionally substituted with one or more substituents selected from the group consisting of $C_1$-$C_4$-alkyl, $C_1$-$C_4$-alkoxy-carbonyl, and $C_1$-$C_4$-alkenyloxy-carbonyl,
$R^{14}$ represents hydroxy, mercapto, amino, $C_1$-$C_6$-alkoxy, $C_1$-$C_6$-alkylthio, $C_1$-$C_6$-alkylamino or di($C_1$-$C_4$-alkyl)amino,
$R^{15}$ represents hydroxy, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)amino,
$R^{16}$ represents $C_1$-$C_4$-alkyl optionally substituted with one or more substituents selected from the group consisting of fluorine, chlorine, and bromine,
$R^{17}$ represents hydrogen, $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, thienyl, thiazolyl, or piperidinyl; phenyl optionally substituted with one or more substituents selected from the group consisting of fluorine, chlorine, and bromine; or $C_1$-$C_4$-alkyl-substituted phenyl,
$R^{18}$ represents hydrogen; $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, thienyl, thiazolyl, or piperidinyl; phenyl optionally substituted with one or more substituents selected from the group consisting of fluorine, chlorine and bromine; or $C_1$-$C_4$-alkyl-substituted phenyl, or
$R^{17}$ and $R^{18}$ together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle,
$R^{19}$ represents hydrogen, cyano, or halogen, or represents $C_1$-$C_4$-alkyl, $C_3$-$C_6$-cycloalkyl, or phenyl, each of which is optionally substituted with one or more substituents selected from the group consisting of fluorine, chlorine and bromine,
$R^{20}$ represents hydrogen, or in each case optionally hydroxy-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl,
$R^{21}$ represents hydrogen, cyano, or halogen, or represents $C_1$-$C_4$-alkyl, $C_3$-$C_6$-cycloalkyl or phenyl, each of which is optionally substituted with one or more substituents selected from the group consisting of fluorine, chlorine and bromine,
$X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy,
$X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
$X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
or a compound selected from the group consisting of a compound of the general formula (IId)

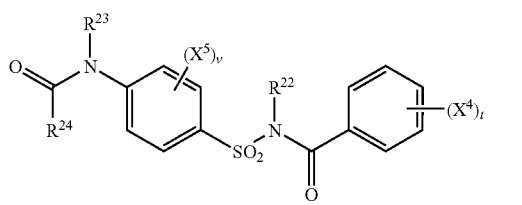

and a compound of the general formula (IIe)

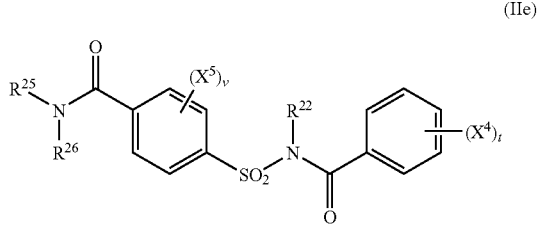

where
t represents a number 0, 1, 2, 3, 4 or 5,
v represents a number 0, 1, 2, 3, 4 or 5,
$R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkyl-amino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or $R^{26}$ together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy.

11. A method of controlling unwanted plant growth, comprising contacting unwanted vegetation or their habitat, separately in close temporal succession, with a compound of the formula (I) according to claim 1 and a crop plant tolerance promoter compound selected from the group consisting of 4-dichloroacetyl-1-oxa-4-azaspiro[4.5]decane (AD-67, MON-4660), 1-dichloroacetyl-hexahydro-3,3,8a-trimethylpyrrolo[1,2-a]pyrimidin-6(2H)one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl, 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenyl-acetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), 1-(ethoxycarbonyl) ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl-1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5] decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-tri-methyloxazolidine (R-29148), 4-(4-chloro-o-tolyl)butyric acid, 4-(4-chlorophenoxy)-butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxy-acetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)-phenyl]-3-methylurea (also known as N-(2-methoxybenzoyl)-4-[(methylaminocarbonyl)-amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl) benzenesulphonamide, a compound of the general formula (IIa)

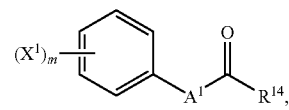

(IIa)

a compound of the general formula (IIb)

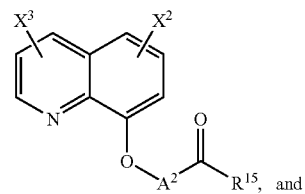

(IIb)

and a compound of the formula (IIc)

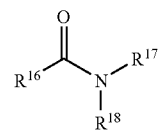

(IIc)

where
m represents a number 0, 1, 2, 3, 4 or 5,
$A^1$ represents one of the following divalent heterocyclic groups

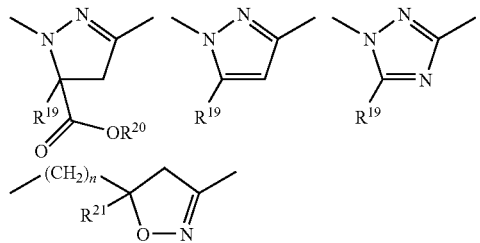

n represents a number 0, 1, 2, 3, 4 or 5,
$A^2$ represents alkanediyl having 1 or 2 carbon atoms optionally substituted with one or more substituents selected from the group consisting of $C_1$-$C_4$-alkyl, $C_1$-$C_4$-alkoxy-carbonyl, and $C_1$-$C_4$-alkenyloxy-carbonyl,
$R^{14}$ represents hydroxy, mercapto, amino, $C_1$-$C_6$-alkoxy, $C_1$-$C_6$-alkylthio, $C_1$-$C_6$-alkylamino or di($C_1$-$C_4$-alkyl) amino,
$R^{15}$ represents hydroxy, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl) amino,
$R^{16}$ represents $C_1$-$C_4$-alkyl optionally substituted with one or more substituents selected from the group consisting of fluorine, chlorine, and bromine,
$R^{17}$ represents hydrogen; $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, or piperidinyl; phenyl optionally substituted with one or more substituents selected from the group consisting of fluorine, chlorine and bromine; or $C_1$-$C_4$-alkyl-substituted phenyl,
$R^{18}$ represents hydrogen; $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, or piperidinyl; phenyl optionally substituted with one or more substituents selected from the group consisting of fluorine, chlorine and bromine; or $C_1$-$C_4$-alkyl-substituted phenyl, or
$R^{17}$ and $R^{18}$ together represent $C_3$-$C_6$-alkanediyl or $C_2$-$C_5$-oxaalkanediyl, each of which is optionally substituted with $C_1$-$C_4$-alkyl, phenyl, furyl, a fused benzene ring or by two substituents which, together with the C atom to which they are attached, form a 5- or 6-membered carbocycle,
$R^{19}$ represents hydrogen, cyano, or halogen, or represents $C_1$-$C_4$-alkyl, $C_3$-$C_6$-cycloalkyl, or phenyl, each of which is optionally substituted with one or more substituents selected from the group consisting of fluorine, chlorine and bromine,
$R^{20}$ represents hydrogen, or in each case optionally hydroxy-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl,
$R^{21}$ represents hydrogen, cyano, or halogen, or represents $C_1$-$C_4$-alkyl, $C_3$-$C_6$-cycloalkyl or phenyl, each of which is optionally substituted with one or more substituents selected from the group consisting of fluorine, chlorine and bromine,
$X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy,
$X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
$X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
or a compound selected from the group consisting of a compound of the general formula (IId)

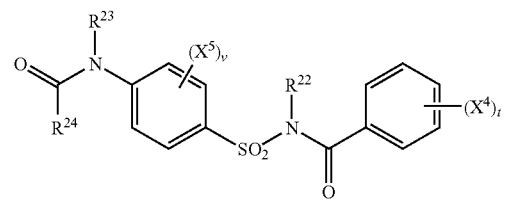

(IId)

and a compound of the general formula (IIe)

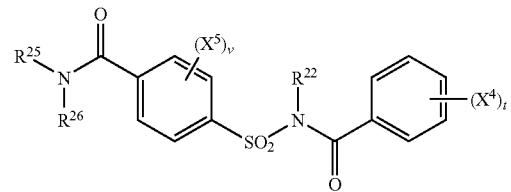

(IIe)

where
t represents a number 0, 1, 2, 3, 4 or 5,
v represents a number 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkyl-amino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or $R^{26}$ together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, on the plants or their surroundings.

12. A composition, comprising
at one compound of the formula (I) according to claim 1 and
at least one salt of the formula (III')

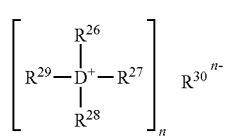
(III')

in which
D represents nitrogen or phosphorus,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the optional substituents being selected from the group consisting of halogen, nitro and cyano,
n represents 1, 2, 3 or 4,
$R^{30}$ represents an organic or inorganic anion.

13. The composition according to claim 12, further comprising at least one penetration promoter.

14. A method of increasing the action of a pesticide or a herbicide, comprising preparing a ready-to-use (spray liquor) composition comprising an active compound of the formula (I) according to claim 1 and a salt of the formula (III')

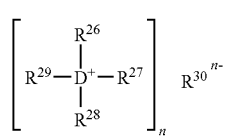
(III')

in which
D represents nitrogen or phosphorus,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selected form the group consisting of halogen, nitro and cyano,
n represents 1, 2, 3 or 4,
$R^{30}$ represents an organic or inorganic anion.

15. A method according to claim 14, comprising preparing the spray liquor using a penetration promoter.

16. A composition, comprising an effective amount of an active-compound combination comprising,
(a') at least one compound according to claim 1 and
(b') at least one crop plant tolerance promoter compound selected from the group consisting of:

4-dichloroacetyl-1-oxa-4-azaspiro[4.5]decane (AD-67, MON-4660), 1-dichloroacetyl-hexahydro-3,3,8a-trimethylpyrrolo[1,2-a]pyrimidin-6(2H)one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)-phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenyl-amino)ethyl)-N-(2-propenyl)acetamide (DKA-24), 2,2-dichloro-N,N-di-2-propenyl-acetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (tenchlorazole-ethyl), phenylmethyl 2-chloro-4-trifluoromethylthiazole-5-carboxylate (flurazole), 4-chloro-N-(1,3-dioxolan-2-ylmethoxy)-a-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl-1-(2,4-dichlorophenyl)-4,5-dihydro-5-methyl-1H-pyrazole -3,5-dicarboxylate (mefenpyr-diethyl), 2-dichloromethyl-2-methyl-1,3-dioxolane (MG-191), 2-propenyl-1-oxa-4-azaspiro[4.5]decane -4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)-butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate,
ethyl 1-(2,4-dichlorophenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloro-quinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoyl-sulphamoyl)-phenyl]-3-methylurea (also known as N-(2-methoxybenzoyl)-4-[(methylaminocarbonyl)-amino]-benzene-sulphonamide), 1-[4-(N-2-methoxybenzoylsulphamoyl)-phenyl]-3,3-dimethylurea, 1-[4-(N-4,5-dimethylbenzoyl-sulphamoyl)-phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzene-sulphonamide, a compound of the general formula (IIa)

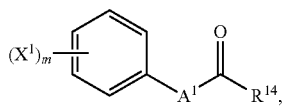

(IIa)

a compound of the general formula (IIb)

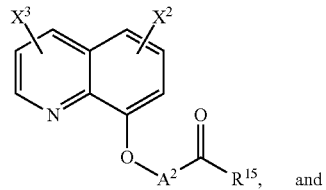

(IIb)

a compound of the formula (IIc)

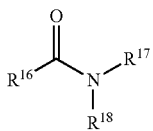

(IIc)

where m represents a number 0, 1, 2, 3, 4 or 5, $A^1$ represents one of the following divalent heterocyclic groups

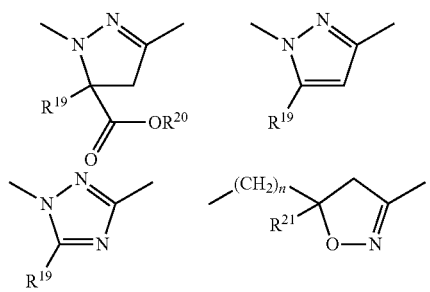

n represents a number 0, 1, 2, 3, 4 or 5, $A^2$ represents alkanediyl having 1 or 2 carbon atoms optionally substituted with one or more substituents selected from the group consisting of $C_1$-$C_4$-alkyl, $C_1$-$C_4$-alkoxy-carbonyl, and $C_1$-$C_4$-alkenyloxy-carbonyl, $R^{14}$ represents hydroxy, mercapto, amino, $C_1$-$C_6$-alkoxy, $C_1$-$C_6$-alkylamino or di($C_1$-$C_4$-alkyl)amino, $R^{15}$ represents hydroxy, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)amino, $R^{16}$ represents $C_1$-$C_4$-alkyl optionally substituted with one or more substituents selected from the group consisting of fluorine, chlorine, and bromine, $R^{17}$ represents hydrogen, $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, or piperidinyl; phenyl optionally substituted with one or more substituents selected from the group consisting of fluorine, chlorine, and bromine; or $C_1$-$C_4$-alkyl-substituted phenyl, $R^{18}$ represents hydrogen; $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, thienyl, thiazolyl, or piperidinyl; phenyl optionally substituted with one or more substituents selected from the group consisting of fluorine, chlorine and bromine; or $C_1$-$C_4$-alkyl-substituted phenyl, or $R^{17}$ and $R^{18}$ together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, or halogen, or represents $C_1$-$C_4$-alkyl, $C_3$-$C_6$-cycloalkyl, or phenyl, each of which is optionally substituted with one or more substituents selected from the group consisting of fluorine, chlorine and bromine, $R^{20}$ represents hydrogen, or in each case optionally hydroxy-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{21}$ represents hydrogen, cyano, or halogen, or represents $C_1$-$C_4$-alkyl, $C_3$-$C_6$-cycloalkyl or phenyl, each of which is optionally substituted with one or more substituents selected from the group consisting of fluorine, chlorine and bromine, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, or a compound selected from the group consisting of a compound of the general formula (IId)

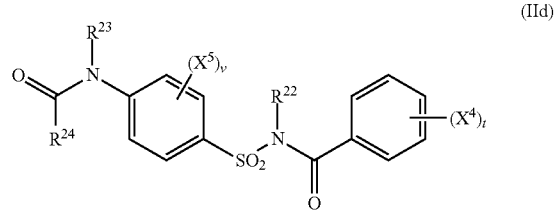

(IId)

and a compound of the general formula (IIe)

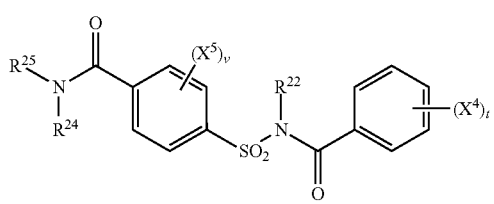
(IIe)

where
t represents a number 0, 1, 2, 3, 4 or 5,
v represents a number 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkyl-amino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or $R^{26}$ together with $R^{25}$ represents in each case optionally $C_1$-$C_4$-alkyl-substituted $C_2$-$C_6$-alkanediyl or $C_2$-$C_5$-oxaalkanediyl,
$X^4$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, and
$X^5$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy;
and at least one salt of the formula (III')

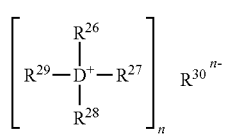
(III')

in which
D represents nitrogen or phosphorus,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the optional substituents being selected from the group consisting of halogen, nitro and cyano,
n represents 1, 2, 3 or 4,
$R^{30}$ represents an organic or inorganic anion.

17. A method of increasing the action of a pesticide or a herbicide, comprising preparing a ready-to-use (spray liquor) composition comprising an effective amount of an active-compound combination comprising,
(a') at least one compound according to claim 1 and
(b') at least one crop plant tolerance promoter compound selected from the group consisting of:
4-dichloroacetyl-1-oxa-4-azaspiro[4.5]decane (AD-67, MON-4660), 1-dichloroacetyl-hexahydro-3,3,8a-trimethylpyrrolo[1,2-a]pyrimidin-6(2H)one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)-phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenyl-amino)ethyl)-N-(2-propenyl)acetamide (DKA-24), 2,2-dichloro-N, N-di-2-propenyl-acetamide (dichlormid), 4,6-dichloro-2-phenylpyrimidine (fenclorim), ethyl 1-(2, 4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl-1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)-butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate,
ethyl 1-(2,4-dichlorophenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloro-quinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoyl-sulphamoyl)-phenyl]-3-methylurea (also known as N-(2-methoxybenzoyl)-4-[(methylaminocarbonyl)-amino]-benzene-sulphonamide), 1-[4-(N-2-methoxybenzoylsulphamoyl)-phenyl]-3,3-dimethylurea, 1-[4-(N-4,5-dimethylbenzoylsulphamoyl)-phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzene-sulphonamide, a compound of the general formula (IIa)

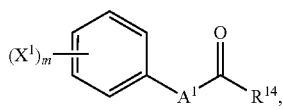

(IIa)

a compound of the general formula (IIb)

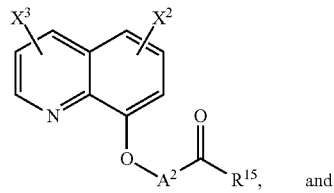

(IIb)

and a compound of the formula (IIc)

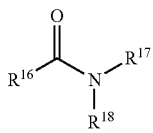

(IIc)

where
m represents a number 0, 1, 2, 3, 4 or 5,
A¹ represents one of the following divalent heterocyclic groups

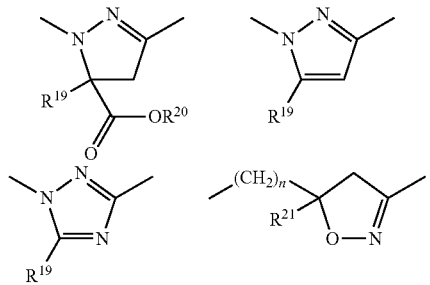

n represents a number 0, 1, 2, 3, 4 or 5, $A^2$ represents alkanediyl having 1 or 2 carbon atoms optionally substituted with one or more substituents selected from the group consisting of $C_1$-$C_4$-alkyl, $C_1$-$C_4$-alkoxy-carbonyl, and $C_1$-$C_4$-alkenyloxy-carbonyl, $R^{14}$ represents hydroxy, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxy, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)amino, $R^{16}$ represents $C_1$-$C_4$-alkyl optionally substituted with one or more substituents selected from the group consisting of fluorine, chlorine, and bromine, $R^{17}$ represents hydrogen, $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, or piperidinyl; phenyl optionally substituted with one or more substituents selected from the group consisting of fluorine, chlorine, and bromine; or $C_1$-$C_4$-alkyl-substituted phenyl, $R^{18}$ represents hydrogen; $C_1$-$C_6$-alkyl, $C_2$-$C_6$-alkenyl or $C_2$-$C_6$-alkynyl, each of which is optionally substituted with one or more substituents selected from the group consisting of fluorine, chlorine and bromine; $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, or piperidinyl; phenyl optionally substituted with one or more substituents selected from the group consisting of fluorine, chlorine and bromine; or $C_1$-$C_4$-alkyl-substituted phenyl, or $R^{17}$ and $R^{18}$ together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, or halogen, or represents $C_1$-$C_4$-alkyl, $C_3$-$C_6$-cycloalkyl, or phenyl, each of which is optionally substituted with one or more substituents selected from the group consisting of fluorine, chlorine and bromine, $R^{20}$ represents hydrogen, or in each case optionally hydroxy-, cyano-, halogen- or $C_1$-$C_4$-alkoxy-substituted $C_3$-$C_6$-cycloalkyl or tri-($C_1$-$C_4$-alkyl)-silyl, $R^{21}$ represents hydrogen, cyano, or halogen, or represents $C_1$-$C_4$-alkyl, $C_3$-$C_6$-cycloalkyl or phenyl, each of which is optionally substituted with one or more substituents selected from the group consisting of fluorine, chlorine and bromine, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, or a compound selected from the group consisting of a compound of the general formula (IId)

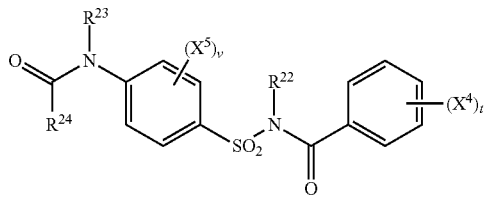

(IId)

and a compound of the general formula (IIe)

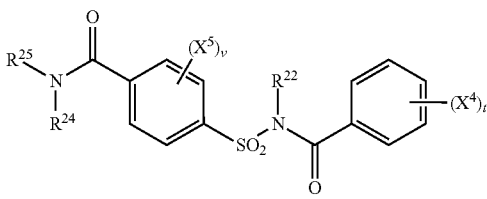

(IIe)

where
t represents a number 0, 1, 2, 3, 4 or 5,
v represents a number 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkyl-amino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or $R^{26}$ together with $R^{25}$ represents in each case optionally $C_1$-$C_4$-alkyl-substituted $C_2$-$C_6$-alkanediyl or $C_2$-$C_5$-oxaalkanediyl,
$X^4$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, and
$X^5$ represents nitro, cyano, carboxy, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$ haloalkoxy;
and a salt of the formula (III')

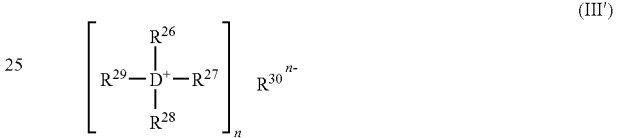

(III')

in which
D represents nitrogen or phosphorus,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selected form the group consisting of halogen, nitro and cyano,
n represents 1, 2, 3 or 4,
$R^{30}$ represents an organic or inorganic anion.

* * * * *